(12) United States Patent
Wangh et al.

(10) Patent No.: US 10,738,347 B2
(45) Date of Patent: Aug. 11, 2020

(54) MULTIPLEX TARGET DETECTION ASSAY

(71) Applicant: Brandeis University, Waltham, MA (US)

(72) Inventors: Lawrence J. Wangh, Auburndale, MA (US); Kenneth E. Pierce, Natick, MA (US); John E. Rice, Quincy, MA (US)

(73) Assignee: Brandeis University, Waltham, MA (US)

( * ) Notice: Subject to any disclaimer, the term of this patent is extended or adjusted under 35 U.S.C. 154(b) by 567 days.

(21) Appl. No.: 14/546,795

(22) Filed: Nov. 18, 2014

(65) Prior Publication Data

US 2015/0148252 A1     May 28, 2015

Related U.S. Application Data

(60) Provisional application No. 61/906,267, filed on Nov. 19, 2013.

(51) Int. Cl.
| | | |
|---|---|---|
| *C12Q 1/68* | (2018.01) | |
| *C12Q 1/6818* | (2018.01) | |
| *C12Q 1/689* | (2018.01) | |

(52) U.S. Cl.
CPC .......... *C12Q 1/6818* (2013.01); *C12Q 1/689* (2013.01)

(58) Field of Classification Search
USPC ......... 435/6.1, 6.11, 91.1, 183; 436/94, 501; 536/23.1, 24.3, 24.33
See application file for complete search history.

(56) References Cited

U.S. PATENT DOCUMENTS

| | | |
|---|---|---|
| 6,812,339 B1 | 11/2004 | Venter et al. |
| 2003/0204075 A9 | 10/2003 | Wang |
| 2007/0016974 A1 | 1/2007 | Byrum et al. |
| 2007/0083945 A1 | 4/2007 | Byrum et al. |
| 2011/0105531 A1 | 5/2011 | Massire et al. |
| 2012/0282611 A1 | 11/2012 | Wangh et al. |

FOREIGN PATENT DOCUMENTS

| | | |
|---|---|---|
| WO | WO-2009/149359 A2 | 12/2009 |
| WO | WO-2011/050173 A1 | 4/2011 |
| WO | WO-2011/102394 A1 | 8/2011 |
| WO | WO-2011/140237 A2 | 11/2011 |
| WO | WO-2012/064978 A2 | 5/2012 |
| WO | WO-2012/075230 A1 | 6/2012 |
| WO | WO-2012/162613 A2 | 11/2012 |

OTHER PUBLICATIONS

Huang et al., Multiplex Fluorescence Melting Curve Analysis for Mutation Detection with Dual-Labeled, Self-Quenched Probes. PLoS One, 6, e19206, 2011.*
International Search Report for Applicaton No. PCT/US14/66189, dated Apr. 16, 2015.
Extended European Search Report issued by the European Patent Office in corresponding Application No. EP 14864352.1, dated Oct. 24, 2017.
Supplementary Partial European Search Report issued by the European Patent Office in corresponding European Application No. 14864352.1, dated Jul. 18, 2017.

\* cited by examiner

*Primary Examiner* — Frank W Lu
(74) *Attorney, Agent, or Firm* — Foley Hoag LLP

(57) ABSTRACT

Provided herein are reagents and kits for detection of multiple target sequences in a single-tube, single-color assay, and methods of use thereof. In particular, multiplex assays are provided for the detection of *Mycobacterium tuberculosis* complex target sequences (e.g., katG, rpoB, inhA promotor, pncA, etc.).

10 Claims, 76 Drawing Sheets

Specification includes a Sequence Listing.

FIG. 12
rpoB Probe 1 OFF (SEQ ID NO: 11)
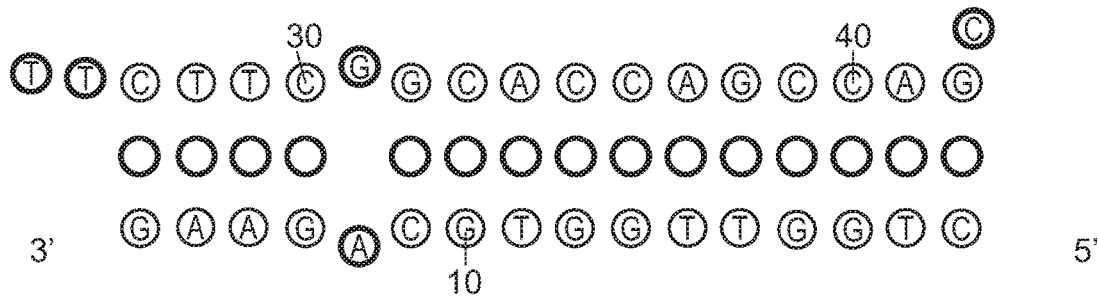
rpoB reference with rpoB Probe1 OFF
ΔG° (55 °C) = -15.17 kcal/mole
ΔH° = -272.63 kcal/mole
ΔS° = -784.58 cal/mole K
Tm = 46.56 °C
[monovalent] = 0.0500 mol/L
[Mg$^{2+}$] = 0.0030 mol/L
rpoB Probe 1a OFF (SEQ ID NO:100)
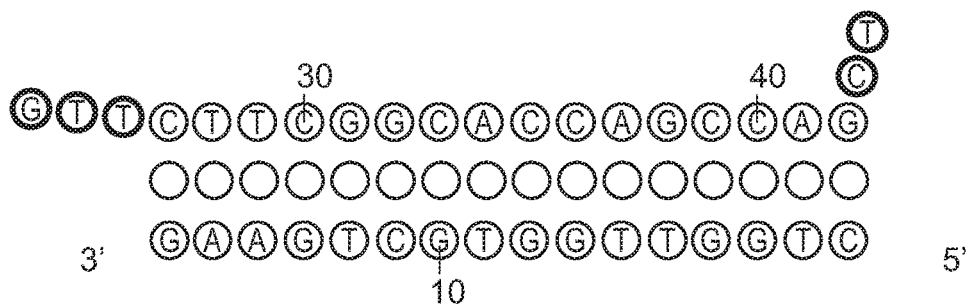
rpoB reference with rpoB Probe1a OFF
ΔG° (55 °C) = -16.03 kcal/mole
ΔH° = -274.83 kcal/mole
ΔS° = -788.67 cal/mole K
Tm = 49.31 °C
[monovalent] = 0.0500 mol/L
[Mg$^{2+}$] = 0.0030 mol/L

Probe 025_040 ON CO560 (SEQ ID NO: 21)

probe 025 040 ON

ΔG° (50 °C) = -51.15 kcal/mole
ΔH° = -990.17 kcal/mole
ΔS° = -2905.81 cal/mole K
Tm = 59.61 °C
[monovalent] = 0.0500 mol/L
$[Mg^{2+}]$ = 0.0020 mol/L Probe 041_054 OFF (SEQ ID NO: 22)

probe 041 054 OFF

$\Delta G°$ (50 °C) = -50.54 kcal/mole
$\Delta H°$ = -1027.17 kcal/mole
$\Delta S°$ = -3022.22 cal/mole K
Tm = 61.63 °C
[monovalent] = 0.0500 mol/L
$[Mg^{2+}]$ = 0.0020 mol/L Probe 055_074 ON CO560 (SEQ ID NO: 23)

probe 055_074 ON $\Delta G°$ (50 °C) = −49.98 kcal/mole
$\Delta H°$ = −973.12 kcal/mole
$\Delta S°$ = −2856.69 cal/mole K
Tm = 66.09 °C
[monovalent] = 0.0500 mol/L
[$Mg^{2+}$] = 0.0020 mol/L probe 101_118 ON $\Delta G° (50 °C) = -47.88$ kcal/mole
$\Delta H° = -947.89$ kcal/mole
$\Delta S° = -2785.09$ cal/mole K
$Tm = 62.43 °C$
[monovalent] = 0.0500 mol/L
[$Mg^{2+}$] = 0.0020 mol/L Probe 119_132 OFF (SEQ ID NO: 26)

probe 119 132 ON

ΔG° (50 °C) = -43.83 kcal/mole
ΔH° = -895.33 kcal/mole
ΔS° = -2635.01 cal/mole K
Tm = 54.59 °C
[monovalent] = 0.0500 mol/L
[$Mg^{2+}$] = 0.0020 mol/L Probe 133_146 ON CO560 (SEQ ID NO: 27)

probe 133 146 ON

$\Delta G° (50 °C) = -46.16$ kcal/mole
$\Delta H° = -929.24$ kcal/mole
$\Delta S° = -2732.72$ cal/mole K
Tm = 52.08 °C
[monovalent] = 0.0500 mol/L
$[Mg^{2+}] = 0.0020$ mol/L Probe 147_156 OFF (SEQ ID NO: 28)

probe 147 156 OFF $\Delta G°$ (50 °C) = -44.44 kcal/mole
$\Delta H°$ = -897.07 kcal/mole
$\Delta S°$ = -2638.51 cal/mole K
Tm = 45.70 °C
[monovalent] = 0.0500 mol/L
$[Mg^{2+}]$ = 0.0020 mol/L Probe 157_175 ON CO560 (SEQ ID NO: 29)

probe 157_175   ON $\Delta G°$ (70 °C) = -11.05 kcal/mole
$\Delta H°$ = -464.55 kcal/mole
$\Delta S°$ = -1321.59 cal/mole K
Tm = 59.15 °C
[monovalent] = 0.0500 mol/L
$[Mg^{2+}]$ = 0.0020 mol/L Probe 176_188 OFF (SEQ ID NO: 30)

probe 176 188 OFF

ΔG° (70 °C) = -45.44 kcal/mole
ΔH° = -956.25 kcal/mole
ΔS° = -2818.53 cal/mole K
Tm = 53.24 °C
[monovalent] = 0.0500 mol/L
[$Mg^{2+}$] = 0.0020 mol/L Probe 189_204 ON (SEQ ID NO: 31)

probe 189 204 ON

ΔG° (70 °C) = -7.29 kcal/mole
ΔH° = -413.36 kcal/mole
ΔS° = -1183.35 cal/mole K
Tm = 50.05 °C
[monovalent] = 0.0500 mol/L
[$Mg^{2+}$] = 0.0020 mol/L Probe 205_215 OFF (SEQ ID NO: 32)

probe 205 215 OFF

$\Delta G° (50 °C) = -43.44$ kcal/mole
$\Delta H° = -914.79$ kcal/mole
$\Delta S° = -2696.43$ cal/mole K
Tm = 43.64 °C
[monovalent] = 0.0500 mol/L
$[Mg^{2+}]$ = 0.0020 mol/L Probe 216_229 ON CO560 (SEQ ID NO: 33)

probe 216 229 ON

$\Delta G° (50 °C) = -44.31$ kcal/mole
$\Delta H° = -921.80$ kcal/mole
$\Delta S° = -2715.41$ cal/mole K
$Tm = 48.71 °C$
[monovalent] = 0.0500 mol/L
$[Mg^{2+}] = 0.0020$ mol/L Probe 230_241 OFF (SEQ ID NO: 34)

probe 230 241 OFF

$\Delta G°$ (50 °C) = -42.83 kcal/mole
$\Delta H°$ = -985.54 kcal/mole
$\Delta S°$ = -2917.25 cal/mole K
Tm = 40.43 °C
[monovalent] = 0.0500 mol/L
[$Mg^{2+}$] = 0.0020 mol/L Probe 242_262 ON CO560 (SEQ ID NO: 35)

probe 242 262 ON

ΔG° (50 °C) = -50.16 kcal/mole
ΔH° = -1027.54 kcal/mole
ΔS° = -3024.53 cal/mole K
Tm = 61.19 °C
[monovalent] = 0.0500 mol/L
[$Mg^{2+}$] = 0.0020 mol/L Probe 263_276 OFF (SEQ ID NO: 36)

probe 263 276 OFF

ΔG° (50 °C) = -48.90 kcal/mole
ΔH° = -1011.07 kcal/mole
ΔS° = -2977.49 cal/mole K
Tm = 58.95 °C
[monovalent] = 0.0500 mol/L
[$Mg^{2+}$] = 0.0020 mol/L Probe 277_293 ON QSR670 (SEQ ID NO: 37)

probe 277 293 ON

ΔG° (50 °C) = -50.19 kcal/mole
ΔH° = -1022.44 kcal/mole
ΔS° = -3008.66 cal/mole K
Tm = 62.83 °C
[monovalent] = 0.0500 mol/L
$[Mg^{2+}]$ = 0.0020 mol/L Probe 294_307 OFF (SEQ ID NO: 38)

probe 294 307 OFF

$\Delta G°$ (50 °C) = -44.39 kcal/mole
$\Delta H°$ = -989.11 kcal/mole
$\Delta S°$ = -2923.48 cal/mole K
Tm = 48.25 °C
[monovalent] = 0.0500 mol/L
[$Mg^{2+}$] = 0.0020 mol/L Probe 308_331 ON (TL) QSR670 (SEQ ID NO: 39)

probe 308 331 ON

$\Delta G° (70\ °C) = -12.20$ kcal/mole
$\Delta H° = -456.34$ kcal/mole
$\Delta S° = -1294.30$ cal/mole K
$T_m = 63.41\ °C$
[monovalent] = 0.0500 mol/L
$[Mg^{2+}] = 0.0020$ mol/L Probe 332_353 OFF (SEQ ID NO: 40)

probe 332 353 OFF

ΔG° (70 °C) = -14.50 kcal/mole
ΔH° = -463.19 kcal/mole
ΔS° = -1307.57 cal/mole K
Tm = 68.23 °C
[monovalent] = 0.0500 mol/L
[$Mg^{2+}$] = 0.0020 mol/L Probe 354_372 ON (TL) QSR670 (SEQ ID NO: 41)

probe 354 372 ON

$\Delta G°$ (50 °C) = -47.13 kcal/mole
$\Delta H°$ = -976.54 kcal/mole
$\Delta S°$ = -2876.12 cal/mole K
Tm = 56.99 °C
[monovalent] = 0.0500 mol/L
[$Mg^{2+}$] = 0.0020 mol/L Probe 373_388 ON QSR670 (SEQ ID NO: 42)

probe 373 388 ON

ΔG° (50 °C) = -48.66 kcal/mole
ΔH° = -997.24 kcal/mole
ΔS° = -2935.42 cal/mole K
Tm = 59.59 °C
[monovalent] = 0.0500 mol/L
[$Mg^{2+}$] = 0.0020 mol/L Probe 389_405 OFF (SEQ ID NO: 43)

probe 389 405 OFF

$\Delta G° (70 °C) = -9.60$ kcal/mole
$\Delta H° = -376.20$ kcal/mole
$\Delta S° = -1068.34$ cal/mole K
Tm = 56.68 °C
[monovalent] = 0.0500 mol/L
$[Mg^{2+}] = 0.0020$ mol/L Probe 406_427 ON -(TB SEQ) (SEQ ID NO: 44)

probe 406 427 ON TB SEQ

$\Delta G°$ (70 °C) = -16.02 kcal/mole
$\Delta H°$ = -407.01 kcal/mole
$\Delta S°$ = -1139.43 cal/mole K
Tm = 71.85 °C
[monovalent] = 0.0500 mol/L
[$Mg^{2+}$] = 0.0020 mol/L Probe 406_427 ON -(BOVIS SEQ)  (SEQ ID NO: 44)

probe 406 427 ON Bovis

ΔG° (70 °C) = -18.81 kcal/mole
ΔH° = -420.11 kcal/mole
ΔS° = -1169.47 cal/mole K
Tm = 77.70 °C
[monovalent] = 0.0500 mol/L
[Mg$^{2+}$] = 0.0020 mol/L Probe 428_448 OFF (SEQ ID NO: 45)

probe 428 448 OFF $\Delta G°$ (55 °C) = -39.90 kcal/mole
$\Delta H°$ = -838.07 kcal/mole
$\Delta S°$ = -2432.34 cal/mole K
Tm = 64.50 °C
[monovalent] = 0.0500 mol/L
$[Mg^{2+}]$ = 0.0020 mol/L Probe 449_478 ON QSR670 (SEQ ID NO: 46)

probe 449 478 ON

$\Delta G° (55 °C) = -39.73$ kcal/mole
$\Delta H° = -824.94$ kcal/mole
$\Delta S° = -2392.84$ cal/mole K
Tm = 63.92 °C
[monovalent] = 0.0500 mol/L
$[Mg^{2+}]$ = 0.0020 mol/L Probe 479_501 OFF (SEQ ID NO: 47)

pncA probe 479 501 OFF

$\Delta G°$ (55 °C) = -37.23 kcal/mole
$\Delta H°$ = -761.96 kcal/mole
$\Delta S°$ = -2208.51 cal/mole K
Tm = 67.69 °C
[monovalent] = 0.0500 mol/L
$[Mg^{2+}]$ = 0.0020 mol/L

FIG. 13 (Continued)
Probe 502_521 (TL) ON QSR670 (SEQ ID NO: 48)
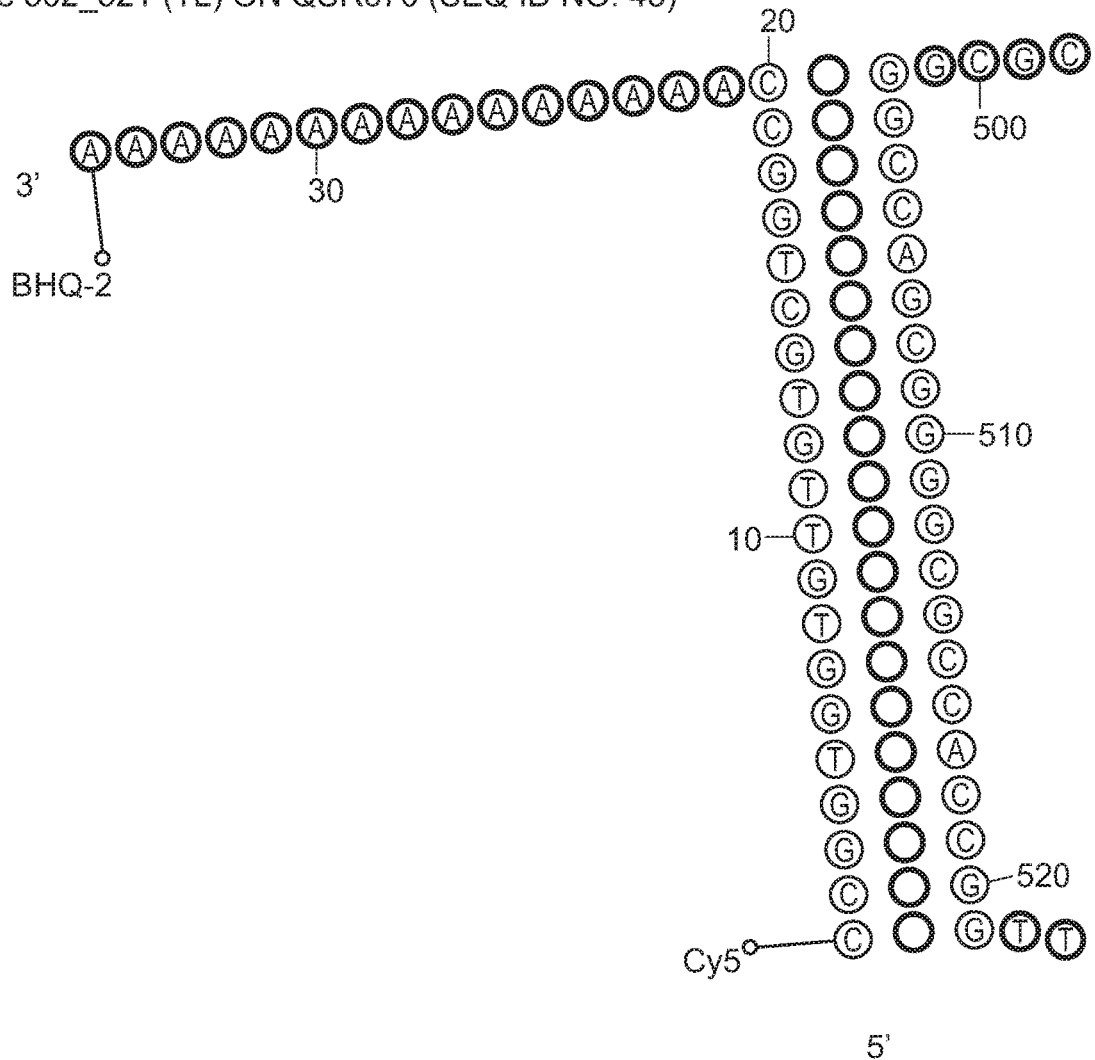
probe 502 521 ON
ΔG° (70 °C) = -11.38 kcal/mole
ΔH° = -403.34 kcal/mole
ΔS° = -1142.23 cal/mole K
Tm = 62.89 °C
[monovalent] = 0.0500 mol/L
[Mg$^{2+}$] = 0.0020 mol/L
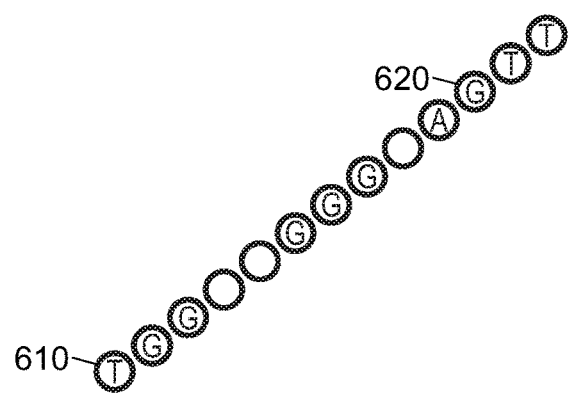

Probe 522_546 OFF (SEQ ID NO: 49)

probe 522 546 OFF

$\Delta G°$ (55 °C) = -37.28 kcal/mole
$\Delta H°$ = -784.82 kcal/mole
$\Delta S°$ = -2278.05 cal/mole K
Tm = 63.89 °C
[monovalent] = 0.0500 mol/L
$[Mg^{2+}]$ = 0.0020 mol/L Probe 547_569 ON QSR670 (SEQ ID NO: 50)

probe 547 569 ON

ΔG° (55 °C) = -41.10 kcal/mole
ΔH° = -842.12 kcal/mole
ΔS° = -2441.02 cal/mole K
Tm = 65.23 °C
[monovalent] = 0.0500 mol/L
[$Mg^{2+}$] = 0.0020 mol/L Probe 570_585 OFF (SEQ ID NO: 51)

probe 570 585 OFF

ΔG° (70 °C) = -12.99 kcal/mole
ΔH° = -412.61 kcal/mole
ΔS° = -1164.55 cal/mole K
Tm = 66.07 °C
[monovalent] = 0.0500 mol/L
[Mg$^{2+}$] = 0.0020 mol/L FIG. 14
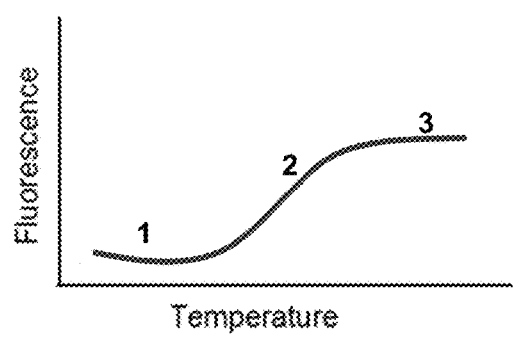
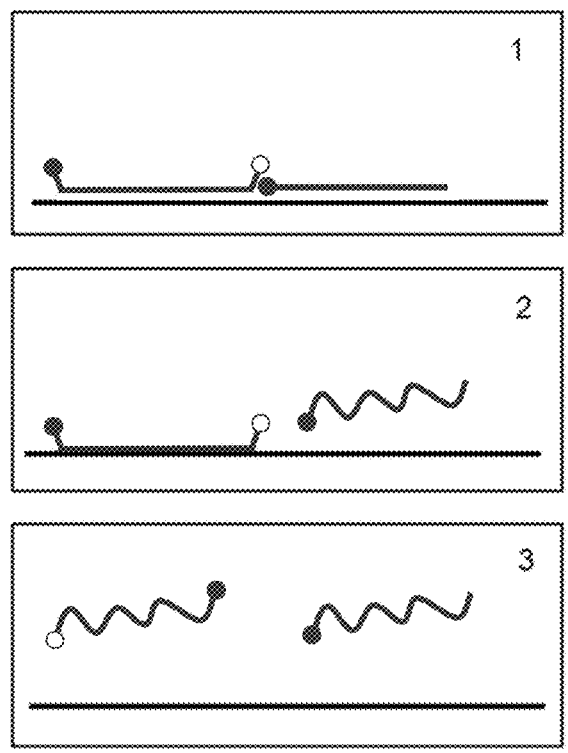

Distinguishing *M. tuberculosis* from *M. Bovis*

A

A

A

B

A

B

C

A

B

C

A

B

MULTIPLEX TARGET DETECTION ASSAY

This application claims the benefit of priority to Provisional Application No. 61/906,267, filed Nov. 19, 2013, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Nov. 9, 2017, is named BUG-06201_SL.txt and is 34,979 bytes in size.

FIELD

Provided herein are reagents and kits for analysis of nucleic acid target sequences in a single-tube, multi-probe assay, and methods of use thereof. In particular embodiments, multiplex assays are provided for the detection of *Mycobacterium tuberculosis* complex target sequences (e.g., katG, rpoB, inhA promotor, pncA, etc.).

BACKGROUND

Homogeneous detection of nucleic acid sequences is well known. Detection may include a dye, for example SYBR Green that fluoresces in the presence of double-stranded amplification reaction product or a fluorescently labeled oligonucleotide hybridization probe. For hybridization probes, "homogeneous detection" means detection that does not require separation of bound (hybridized to target) probes from unbound probes. Among probes suitable for homogeneous detection are dual-labeled probes (e.g., single stranded probes comprising a labeling moiety (e.g., fluorophore and/or quencher) at both the 5' and 3' ends), comprised of single-stranded oligonucleotides with a covalently bound fluorophore on one end and covalently bound quencher on the other end (e.g., quenched probe or self-quenching probed) whose absorption spectrum substantially overlaps the fluorophore's emission spectrum for FRET quenching when the probe is not bound to a target (5' exonuclease probes described in, for example, Livak et al. (1995) PCR Methods Appl. 4:357-362; herein incorporated by reference in its entirety), hairpin probes labeled on one end with a fluorophore and on the other end with a quencher (molecular beacon probes described in, for example, Tyagi et al. (1996) Nature Biotechnology 14:303-308; herein incorporated by reference in its entirety). At an appropriate temperature a hairpin probe has a stem/loop structure when not bound to a target and in this structure the fluorophore and the quencher interact so closely that they engage in contact-quenching rather than FRET quenching. Double-stranded probes can also be used in homogeneous reactions. These probes have a covalently linked fluorophore on one strand and a covalently linked quencher on the complementary end of the other strand (yin-yang probes described in, for example, Li et al. (2002) Nucl. Acids Res. 30, No. 2 e5; herein incorporated by reference in its entirety), in addition linear probes having a fluorophore that absorbs emission from a fluorophore and re-emits at a longer wavelength (probes described in, for example, United States published patent application US2002/0110450; herein incorporated by reference in its entirety), and pairs of linear probes, one labeled with a donor fluorophore and one labeled with an acceptor fluorophore that hybridize near to one another on a target strand such that their labels interact by FRET (FRET probe pairs described in, for example, U.S. Pat. No. 6,140,054; herein incorporated by reference in its entirety). Detection methods include methods for detecting probes bound to single-stranded nucleic acid sequences (including variant target sequences), double-stranded targets including heteroduplexes comprised of imperfect complementary strands, or both.

Nucleic acid target sequences suitable for probing can be obtained directly in some instances by isolation and purification of nucleic acid in a sample. In other instances nucleic acid amplification is required. Amplification methods for use with homogeneous detection include the polymerase chain reaction (PCR), including symmetric PCR, asymmetric PCR and LATE-PCR, any of which can be combined with reverse transcription for amplifying RNA sequences, NASBA, SDA, and rolling circle amplification. Amplification-detection methods may rely on fluorescence due to probe hybridization, or they may rely on digestion of hybridized probes during amplification, for example, the 5' nuclease amplification-detection method. If a sample contains or is amplified to contain, double-stranded target, for example, the amplification product of a symmetric PCR reaction, but single-stranded target is desired, separation of plus and minus strands can be accomplished by known methods, for example, by labeling one primer with biotin and separating the biotin-containing product strands from the other strands by capture onto an avidin-containing surface, which is then washed.

Certain fluorescent probes useful for homogeneous detection contain a fluorophore-labeled strand that emits a detectable signal when it hybridizes to its target sequence in a sample. For example, a molecular beacon probe is single-stranded and emits a detectable fluorescent signal upon hybridization. A ResonSense® probe is also single stranded and signals only when hybridized provided that the sample contains a dye, generally a SYBR dye, which stimulates hybridized probes by FRET when the dye is stimulated. Yin-yang probes are quenched double-stranded probes that include a fluorophore-labeled strand that emits a detectable signal it hybridizes to its target. FRET probe pairs, on the other hand, are probe pairs that emit a detectable fluorescent signal when both probes of the pair hybridize to their target sequences. Some amplification assays, notably the 5' nuclease assay, include signal generation caused by probe cutting to generate fluorescent probe fragments rather than simply probe hybridization.

Certain probes that generate a signal upon hybridization can be constructed so as to be "allele-specific," that is, to hybridize only to perfectly complementary target sequences, or to be mismatch-tolerant, that is, to hybridize to target sequences that either are perfectly complementary to the probe sequence or, hybridize at a somewhat lower temperature to target sequences that are generally complementary but contain one or more mismatches. Allele-specific molecular beacon probes have relatively short probe sequences, generally single-stranded loops not more than 25 nucleotides long with hairpin stems 4-6 nucleotides long, and are useful to detect, for example, single-nucleotide polymorphisms. Marras et al. (1999) Genetic Analysis Biomolecular Engineering 14: 151-156 (herein incorporated by reference in its entirety), discloses a real-time symmetric PCR assay that includes in the reaction mixture four molecular beacons having 16-nucleotide long probe sequences and 5-nucleotide stems, wherein each probe is a different color, that is, includes a fluorophore that is detectably distinguishable by its emission wavelength, and a probe sequence differing from the others by a single nucleotide. The sample is analyzed after each PCR cycle to detect which color arises and thereby to identify which of four possible target sequences perfectly complementary to one of the probes is present in a sample. Mismatch-tolerant molecular beacon probes have longer probe sequences, generally single-stranded loops of up to 50 or even 60 nucleotides with hairpin stems maintained at 4-7 nucleotides. Tyagi et al. European Patent No. 1230387 (herein incorporated by reference in its entirety) discloses a symmetric PCR amplification and homogeneous detection assay using a set of four differently colored mismatch-tolerant molecular beacon probes having different probe sequences 40-45 nucleotides long and stems 5-7 nucleotides long, to hybridize competitively to, and thereby interrogate, a 42-nucleotide long hypervariable sequence of mycobacterial 16S rRNA genes to determine which of eight mycobacterial species is present in a sample. The sample is analyzed by determining a ratio of fluorophore intensities at one or more temperatures to identify the species that is present. El-Hajj et al (2009) J. Clin. Microbiology 47:1190-1198 (herein incorporated by reference in its entirety), discloses a LATE-PCR amplification and homogeneous detection assay similarly using four differently colored mismatch-tolerant molecular beacon probes having different probe sequences 36-39 nucleotides long and stems 5 nucleotides long to hybridize competitively to, and thereby interrogate, a 39-nucleotide long hypervariable sequence of mycobacterial 16S rRNA genes to determine which of twenty-seven mycobacterial species is present in a sample. Each of the four probes is a "consensus probe," that is, it has a single-stranded loop complementary to multiple species but perfectly complementary to none of them. Genomic DNA from some 27 different species were separately amplified, the Tm of each probe was determined by post-amplification melt analysis, and data was tabulated. To analyze a sample containing an unknown species, the sample was amplified and analyzed as above. The Tm's of all four probes were compared to the tabulated results to identify the species present in the sample.

Multiple probes, both mismatch-tolerant and allele-specific, have been used to interrogate multiple target sequences. El-Hajj et al. (2001) J. Clin. Microbiology 39:4131-4137 (herein incorporated by reference in its entirety), discloses performing a single, multiplex, real-time, symmetric PCR assay containing five differently colored, allele-specific molecular beacons, three complementary to one amplicon strand and two complementary to the other amplicon strand, which together span an 81-nucleotide long region of the rpoB gene core region of *M. tuberculosis* in overlapping fashion. Probe fluorescence intensities were obtained, and failure of any one of the probes to hybridize and signal was taken as an indication of drug resistance. Wittwer et al. U.S. Pat. No. 6,140,054 (herein incorporated by reference in its entirety) discloses a multiplex symmetric PCR assay for detecting single and double base-pair mismatches in two sequences (C282Y and H63D sites) of the human HFE gene using a primer pair for each site, a FRET probe pair for each site, and rapid thermal cycling. Each probe pair includes a mismatch-tolerant fluorescein donor probe 20-30 nucleotides in length, positioned to hybridize to target sites of possible variations, and a Cy5 acceptor probe 35-45 nucleotides long, called the "anchor" probe, because it remains hybridized as its companion fluorescein probe melts off the target sequence at a melting temperature dependent on its degree of complementarity.

Usable single-tube assays that provide detailed characterization of multiple target sequences using a single-color reporter would reduce the cost and complexity analysis.

SUMMARY

Provided herein are reagents and kits for analysis of nucleic acid target sequences in a single-tube, multi-probe assay, and methods of use thereof. In particular embodiments, multiplex assays are provided for the detection of *Mycobacterium tuberculosis* complex target sequences (e.g., katG, rpoB, inhA promotor, pncA, etc.).

In particular embodiments, a single-tube, single-color, multiplex (e.g., tetraplex) assay is provided for the detection of *Mycobacterium tuberculosis* complex target sequences (e.g., katG, rpoB, inhA promotor, etc.), for example, together with a $1^{st}$ (amplifiable) internal control target sequence. The multiple (e.g., four) single-stranded products of such a multiplex (e.g., tetraplex) are detected using sets of probes labeled with a fluorophore in one color. Reaction components can also include a second (non-amplifiable) control, also labeled in the same color (or labeled in a different color). The use of such reagents and methods with other detection and characterization assays (e.g., detection of the Mycobacterial pncA gene with an additional color) is provided herein.

In other embodiments, provided herein are multiplex, multicolor, assays for the detection and/or characterization of, for example, the Mycobacterial pncA gene. In some embodiments, these multicolor assays utilize multiple probes, labeled with a single color, that bind to two or more different targets (e.g., e.g., different target amplicons) over distinct temperature ranges. Further, is some such embodiments, a single target is bound by probes labeled with multiple different color labels.

In some embodiments, provided herein is a homogeneous assay method for analyzing multiple single-stranded nucleic acid target sequences in a sample, comprising: (a) providing: (i) a sample containing multiple nucleic acid target sequences in single-stranded form, and (ii) for each nucleic acid target sequence at least one detectably distinguishable set of two interacting hybridization probes, each of which hybridizes to the at least one target, said interacting hybridization probes comprising: (A) a quencher probe labeled with a non-fluorescent quencher, and (B) a signaling probe that upon hybridization to the at least one target sequence in the sample in the absence of the quencher probe emits a signal above background, wherein, if both probes are hybridized to the at least one target sequence, the non-fluorescent quencher of the quencher probe quenches the signal from the signaling probe via contact-quenching; and (b) analyzing hybridization of the signaling and quenching probes to the at least one target sequence as a function of temperature, the analysis including an effect on each signaling probe due to its associated quencher probe, making it possible to detect temperature-dependent increases, decreases, or both or neither, changes in the signal emanating from the fluorophore of the signaling probe in the absence of contact quenching (See, e.g., U.S. Pat. Pub. No. 2012/0282611; herein incorporated by reference in its entirety).

In some embodiments, the present invention provides methods for analyzing multiple single-stranded nucleic acid target sequences in a sample, comprising: (a) contacting a sample comprising single-stranded nucleic acid target sequences (e.g., two or more) with detection reagents, said detection regents comprising a sets of probe-pairs for each of the target sequences, each of said probe-pair comprising: (i) a quencher probe labeled with a non-fluorescent quencher, and (ii) a signaling probe labeled with a fluorophore, wherein background signal is emitted from the signaling probe when the signaling probe is not bound to the target sequence, wherein above background signal is emitted from the signaling probe when the signaling probe is bound to the target sequence but the quencher probe is not bound to the target sequence, wherein the signal from the signaling probe is quenched by the non-fluorescent quencher when both the signaling probe and the quencher probe are bound to the target sequence; wherein the signaling probes of each of the probe sets are labeled with the same fluorophore; and (b) analyzing the signal from the signaling probes as a function of temperature. In certain embodiments, the analyzing comprises determining an effect on each signaling probe due to its associated quencher probe, making it possible to detect temperature-dependent increases, decreases, or both or neither, changes in the signal emanating from the fluorophore of the signaling probe in the absence of contact quenching (See, e.g., U.S. Pat. Pub. No. 2012/0282611; herein incorporated by reference in its entirety).

In some embodiments, the single-stranded nucleic acid target sequences are produced by amplification from a sample nucleic acid (e.g., from a biological, clinical, or environmental sample) using amplification reagents. In some embodiments, the sample nucleic acid comprises M. tuberculosis complex (e.g., M. tuberculosis, M. bovis, etc.) genomic nucleic acid. In some embodiments, the sample nucleic acid is obtained from a biological, clinical, or environmental sample containing M. tuberculosis complex bacteria (e.g., M. tuberculosis, M. bovis, etc.). In some embodiments, the sample nucleic acid comprises one or more (e.g., all) of the katG, rpoB, inhA promotor, and/or pncA genes. In some embodiments, the sample nucleic acid comprises one or more of the katG, rpoB, inhA promotor, pncA, mabA, embB, rpsL, rss, gyrA, gyrB, eis, tlyA 16s rDNA genes.

In some embodiments, the present invention provides a kit or reagent mix for analyzing single-stranded nucleic acid target sequences comprising: (a) amplification reagents comprising primer pairs specific for each of the target sequences, said primer pairs comprising an excess primer and a limiting primer; and (b) detection reagents comprising sets of probe-pairs for each of the target sequences, each of said probe-pair comprising: (i) a quencher probe labeled with a non-fluorescent quencher, and (ii) a signaling probe labeled with a fluorophore, wherein background signal is emitted from the signaling probe when the signaling probe is not bound to the target sequence, wherein above background signal is emitted from the signaling probe when the signaling probe is bound to the target sequence but the quencher probe is not bound to the target sequence, wherein the signal from the signaling probe is quenched by the non-fluorescent quencher when both the signaling probe and the quencher probe are bound to adjacent sequences in the target sequence, wherein the signaling probes of each of the probe sets are labeled with the same fluorophore, and wherein the target-specific primers have melting temperatures with the target sequences above the melting temperatures of the signaling probe and quenching probe for the respective target sequence.

In some embodiments, the target sequences are Mycobacterium tuberculosis complex (e.g., Mycobacterium tuberculosis, Mycobacterium bovis, etc.) nucleic acid sequences. In some embodiments, a target sequence comprise all or a portion of a katG, rpoB, inhA promotor, or pncA gene. In some embodiments, a target sequence comprise all or a portion of the katG, rpoB, inhA promotor, pncA, mabA, embB, rpsL, rss, gyrA, gyrB, eis, tlyA, 16s rDNA genes. In some embodiments, a method or kit is provided for the detection/characterization of 2 or more (e.g., 2, 3, 4, 5, 6, 7, 8, 9, 10, or more) target sequences (e.g., selected from portions of the aforementioned genes).

In some embodiments, each of the signaling probes hybridize to their respective target sequence at distinct temperature ranges (e.g., melting of the lower Tm probe from the target begins at about a first temperature (e.g., 15° C., 20° C., 25° C., 30° C., 35° C., 40° C., 45° C., 50° C., 55° C., 60° C., 65° C., 70° C., 75° C., 80° C., or temperatures therein) and melting of the higher Tm probe from the target is complete at about a second temperature (e.g., 25° C., 30° C., 35° C., 40° C., 45° C., 50° C., 55° C., 60° C., 65° C., 70° C., 75° C., 80° C., 85° C., 90° C., or temperatures therein)).

In some embodiments, the distinct temperature ranges of the various probe sets are non-overlapping. In some embodiments, two or more of the distinct temperature ranges of the various probe sets partially overlap. In some embodiments, two or more of the distinct temperature ranges of the various probe sets overlap. In some embodiments, peak signal of signaling probes from two probe sets are separated by less than 40° C. (e.g., <35° C., <20° C., <25° C., <20° C., <15° C., <10° C., <5° C.). In some embodiments, peak signal of signaling probes from two probe sets are separated by more than 5° C. (e.g., >10° C., >15° C., >20° C., >25° C., >30° C.). In some embodiments, the melting temperature for hybridization of the signaling probe to the target sequence is higher than the temperature for hybridization of the quencher probe to the target sequence (e.g., in one or more probe sets, in all probe sets). In some embodiments, the melting temperature for hybridization of the signaling probe to the target sequence is lower than the temperature for hybridization of the quencher probe to the target sequence (e.g., in one or more probe sets, in all probe sets). In some embodiments, the signaling probes are quenching probes that comprise a non-fluorescent quencher that reduces the signal from a fluorophore when the signaling probe is not hybridized to a target. In some embodiments, the signaling probes are dual-labeled probes (e.g., 3' and 5' labeled) comprised of a single-stranded oligonucleotide comprised of DNA having a non-fluorescent quencher moiety which reduces the signal from a fluorescent moiety when said probe is not hybridized to a target (e.g., self-quenching). In some embodiments, the signaling probes are molecular beacon probes. In some embodiments, the signaling probes comprise a target binding region and a non-binding region between the non-fluorescent quencher and the fluorescent dye.

In some embodiments, analyzing the signal from the signaling probes as a function of temperature comprises generating a melt curve or annealing curve. In some embodiments, analyzing the signal from the signaling probes as a function of temperature comprises monitoring signal at multiple discrete temperatures. In some embodiments, a melt curve, annealing curve, or single temperature signal is compared to a known curve, control curve, or known or control value. In some embodiments, analyzing the signal from the signaling probes detects the presence of the target sequences. In some embodiments, analyzing the signal from the signaling probes detects the presence of sequence variations (e.g., mutations) within the target sequences. In some embodiments, specific changes (e.g., SNP) in target sequence are identifiable.

In some embodiments, the signaling probe and quencher probe of a first probe set have melting temperatures for hybridization to a first target sequence in the range of 10-75° C. (e.g., 35-55° C.). In some embodiments, the first target sequence is a portion of the *M. tuberculosis* inhA promotor gene. In some embodiments, the signaling probe of the first probe set has at least 70% identity (e.g., >70%, >75%, >80%, >85%, >90%, 95%, >98%, >99%) with SEQ ID NO: 19 and the quencher probe of the first probe set has at least 70% identity (e.g., >70%, >75%, >80%, >85%, >90%, 95%, >98%, >99%) with SEQ ID NO: 20. In some embodiments, the signaling probe and quencher probe of a second probe set have melting temperatures for hybridization to a second target sequence in the range of 10-75° C. (e.g., 45-60° C.). In some embodiments, the second target sequence is a portion of the *M. tuberculosis* katG gene. In some embodiments, the signaling probe of the second probe set has at least 70% identity with SEQ ID NO: 17 and the quencher probe of the second probe set has at least 70% identity (e.g., >70%, >75%, >80%, >85%, >90%, 95%, >98%, >99%) with SEQ ID NO: 18. In some embodiments, the signaling probe and quencher probe of a third probe set have melting temperatures for hybridization to a third target sequence in the range of 10-75° C. (e.g., 55-75° C.). In some embodiments, the third target sequence is a portion of the *M. tuberculosis* rpoB gene. In some embodiments, the signaling probe of the third probe set has at least 70% identity with one of SEQ ID NOS: 12, 14, or 15 and the quencher probe of the third probe set has at least 70% identity (e.g., >70%, >75%, >80%, >85%, >90%, 95%, >98%, >99%) with one of SEQ ID NOS: 11, 13, or 16. In some embodiments rpoB signaling probes 4, and/or 5, and/or quencher probe 1 can be substituted with signaling probes 4a, 5a, or quencher probe 1a that have slightly different sequences in order to achieve greater allele discrimination at specific codons. In some embodiments, the fourth target sequence is a portion of the *M. tuberculosis* pncA gene. In some embodiments, the signaling probe of a fourth probe set has at least 70% identity with one of SEQ ID NOS: 21, 23, 25, 27, 29, 31, 33, 35, 37, 39, 41, 42, 44, 46, 48, or 50 and the quencher probe of the third probe set has at least 70% identity (e.g., >70%, >75%, >80%, >85%, >90%, 95%, >98%, >99%) with one of SEQ ID NOS: 22, 24, 26, 28, 30, 32, 34, 36, 38, 40, 43, 45, 47, 49, 50, or 51. In some embodiments, multiple probe sets are used in identification/characterization of the pncA gene (e.g., hybridizing with the same single-stranded target) in a single assay (e.g., single color, single tube).

In some embodiments, two or more probe sets are provided for detection/characterization of different portions of a single single-stranded target sequence.

In some embodiments, the detection reagents further comprise one or more control sequences, probes, etc. In some embodiments, the detection reagents further comprise a first single-stranded or double stranded internal control sequence and a first control signal probe, wherein the signal probe for the first control sequence is labeled with the same fluorophore as the signaling probes for at least one of the target sequences. In some embodiments, the detection reagents further comprise a first single-stranded internal control sequence and a first control probe set comprising a corresponding quencher probe and signal probe, wherein the signal probe for the first control sequence is labeled with the same fluorophore as the signaling probes for at least one of the target sequences. In some embodiments, the signaling probe and quencher probe of a first control probe set have melting temperatures of less than 35° C. (e.g., <30° C., 25° C., 20° C., 15° C.) for hybridization to an internal control sequence. In some embodiments, the signaling probe and quencher probe of a first control probe set have melting temperatures for hybridization to an internal control sequence in the range of 5-15° C., 10-20° C., 15-25° C., 20-30° C., 25-35° C., etc. In some embodiments, the internal control sequence is a portion of an internal control plasmid (e.g., provided in a reaction mixture). In some embodiments, the signaling probe of the first control probe set has at least 70% identity or complementarity (e.g., >70%, >75%, >80%, >85%, >90%, 95%, >98%, >99%) with SEQ ID NO: 52 and the quencher probe of the first control probe set has at least 70% identity or complementarity (e.g., >70%, >75%, >80%, >85%, >90%, 95%, >98%, >99%) with SEQ ID NO: 53.

In some embodiments, the detection reagents further comprise a second single-stranded internal control sequence and a second control probe set comprising corresponding quencher probe and signal probe, wherein the signal probe for the second control sequence is labeled with the same fluorophore as the signaling probes of at least one of the target sequences. In some embodiments the quencher probe is covalently attached to the internal control sequence such that the quencher can quench the fluorophore on the complementary probe strand. In some embodiments, the signaling probe and quencher probe of the second control probe set have melting temperatures for hybridization to internal control sequence in the range of 70-80° C., 75-80° C., 80-90° C., etc. In some embodiments, the signaling probe of the second control probe set has at least 70% identity (e.g., >70%, >75%, >80%, >85%, >90%, 95%, >98%, >99%) with SEQ ID NO: 54 and the quencher probe of the control probe set has at least 70% identity (e.g., >70%, >75%, >80%, >85%, >90%, 95%, >98%, >99%) with SEQ ID NO: 55.

In some embodiments, amplification reagents comprise primers pairs (e.g., target-specific or mismatch tolerant primers designed to hybridize to a specific region of a gene). In some embodiments, primers pairs comprise an excess primer and limiting primer (U.S. Pat. No. 7,198,897; herein incorporated by reference in its entirety). In some embodiments, the target-specific primers have melting temperatures with the target sequences above the melting temperatures of the signaling probe and quenching probe for the respective target sequence. In some embodiments, the amplification is non-symmetric amplification to produce single-stranded nucleic acid target sequences. In some embodiments, amplification is by LATE-PCR. In some embodiments, a first target specific primer pair comprises an excess primer at least 70% identity with SEQ ID NO: 6 and a limiting primer at least 70% identity (e.g., >70%, >75%, >80%, >85%, >90%, 95%, >98%, >99%) with SEQ ID NO: 5. In some embodiments, a second target specific primer pair comprises an excess primer at least 70% identity with SEQ ID NO: 4 and a limiting primer at least 70% identity (e.g., >70%, >75%, >80%, >85%, >90%, 95%, >98%, >99%) with SEQ ID NO: 3. In some embodiments, a third target specific primer pair comprises an excess primer at least 70% identity with SEQ ID NO: 2 and a limiting primer at least 70% identity (e.g., >70%, >75%, >80%, >85%, >90%, 95%, >98%, >99%) with SEQ ID NO: 1. In some embodiments, a fourth target specific primer pair comprises an excess primer at least 70% identity with SEQ ID NO: 7 and a limiting primer at least 70% identity (e.g., >70%, >75%, >80%, >85%, >90%, 95%, >98%, >99%) with SEQ ID NO: 8.

In some embodiments, amplification reagents comprise an oligonucleotide reagent to: suppress mispriming, increase polymerase selectivity against 3' terminal mismatches, increase polymerase selectivity against AT-rich 3' ends, reduce scatter among replicates, suppress polymerase 5' exonuclease activity, and/or inhibit polymerase activity (such reagents may be referred to as Primesafe, or Primesafe I, or Primersafe II reagents; See, e.g., U.S. Pub. No. 2012/0088275; U.S. Pub. No. 2009/0226973; U.S. Pub. No. 2006/0177842; herein incorporated by reference in their entireties). In some embodiments, the oligonucleotide reagent comprises a pair of complementary oligonucleotides with a melting temperature of hybridization of about 70° C., each of said oligonucleotides being 3' and 5' end-labeled. In some embodiments, the complementary oligonucleotides are end-labeled with dabcyl groups. In some embodiments, the complementary oligonucleotides have greater than 70% identity (e.g., >70%, >75%, >80%, >85%, >90%, 95%, >98%, >99%) with SEQ ID NOS: 56 and 57.

In some embodiments, the present invention provides kits and/or reagent mixes for analyzing at single-stranded nucleic acid target sequences. In some embodiments, such kits and/or reagent mixes find use in methods of identifying/detecting/characterizing target sequences described herein. In some embodiments, such kits and/or reagent mixes comprise primers, probes, and/or control seqeunces described herein. In some embodiments, kits and/or reagent mixes further comprise suitable buffers, salt, enzymes, etc.

In some embodiments, the present invention provides methods for analyzing four or more nucleic acid target sequences in a sample, comprising: (a) contacting a sample comprising four or more nucleic acid target sequences with amplification reagents, wherein the amplification regents comprise sets of primer pairs specific for each of the four or more nucleic acid target sequences; (b) amplifying the nucleic acid target sequences under conditions that produce a single stranded amplicon of each of the target sequences; (c) contacting the sample with detection reagents, said detection regents comprising sets of probe-pairs for each of the target sequences, each of said probe-pairs comprising: (i) a quencher probe labeled with a non-fluorescent quencher, and (ii) a signaling probe labeled with a fluorescent dye, wherein background signal is emitted from the signaling probe when the signaling probe is not bound to the target sequence, wherein above background signal is emitted from the signaling probe when the signaling probe is bound to the target sequence but the quencher probe is not bound to the target sequence, wherein the signal from the signaling probe is quenched by the non-fluorescent quencher when both the signaling probe and the quencher probe are bound to the target sequence, wherein the signaling probes of each of the probe sets are labeled with the same fluorescent dyes; and (d) analyzing the signal from the signaling probes as a function of temperature. In some embodiments the signaling probe is a self-quenching probe having a fluorophore and a non-fluorescent quencher.

In some embodiments, the present invention provides kits comprising: (a) an internal control nucleic acid, (b) detection reagents, said detection regents comprising: (i) probe sets specific for each of the target sequences and the internal control nucleic acid, each of said probe sets comprising: (A) a quencher probe labeled with a non-fluorescent quencher, and (B) a signaling probe labeled with a fluorescent dye; wherein background signal is emitted from signaling probes when the signaling probe is not bound to the target sequence, wherein above background signal is emitted from the signaling probe when the signaling probe is bound to the target sequence but the quencher probe is not bound to the target sequence, wherein the signal from the signaling probe is quenched by the non-fluorescent quencher when both the signaling probe and the quencher probe are bound to the target sequence, wherein the signaling probes of each of the probe sets for the target sequences are labeled with the same fluorescent dyes, and wherein the quencher probe and signaling probe specific for the internal control nucleic acid have melting temperatures of less than 35° C. with a single stranded portion of internal control nucleic acid; and (c) amplification reagents, said amplification reagents comprising: primer pairs specific for each of the target sequences and the internal control nucleic acid, said primer pairs comprising an excess primer and a limiting primer, and wherein the target-specific primers have melting temperatures with the target sequences above the melting temperatures of the signaling probe and quenching probe for the respective target sequence or internal control nucleic acid. In some embodiments the signaling probe is a self-quenching probe having a fluorophore and a non-fluorescent quencher.

In some embodiments, methods are provided for analyzing two or more nucleic acid target sequences in a sample, comprising: (a) contacting the sample with the above internal control nucleic acid, detection reagents and amplification reagents; (b) amplifying a portion of the internal control nucleic acid and portions of each of the two or more nucleic acid target sequences with the amplification reagents to produce single-stranded amplicons; and (c) detecting signal from the signaling probes at a range of temperatures.

In some embodiments, the present invention provides kits or reagent mixes for detection and/or characterization of Mycobacteria in a sample comprising: (a) primer pairs specific for target sequences within the inhA promotor, katG, and rpoB genes, said primer pairs comprising an excess primer and a limiting primer; and (b) probe set for the target sequences within the inhA promotor, katG, and rpoB genes, each of said probe sets comprising: (i) a quencher probe labeled with a non-fluorescent quencher, and (ii) a self-quenching signaling probe having a fluorophore plus a non-fluorescent quencher, wherein background signal is emitted from the signaling probe when the signaling probe is not bound to the target sequence, wherein above background signal is emitted from the signaling probe when the signaling probe is bound to the target sequence but the quencher probe is not bound to the target sequence, wherein the signal from the signaling probe is quenched by the non-fluorescent quencher when both the signaling probe and the quencher probe are bound to the target sequence, wherein the signaling probes of each of the probe sets are labeled with the same fluorescent dyes, and wherein the primer pairs have melting temperatures with the target sequences above the melting temperatures of the signaling probe and quenching probe for the respective target sequence. In some embodiments, provided herein are methods for detection and/or characterization of Mycobacteria in a sample comprising: (a) contacting the sample with the kit or reagent mix above; (b) amplifying the target sequences with the primer pairs to produce single-stranded amplicons; and (c) detecting signal from the signaling probes at a range of temperatures.

In some embodiments, the present invention provides kits or reaction mixtures comprising: (a) a first internal control, comprising: (i) a first control sequence, (ii) primer pairs comprising excess and limiting primers for amplification of a single strand of all or a portion of the first control sequence to produce a first control amplicon, (iii) a quencher probe labeled with a non-fluorescent quencher and complementary to a first portion of the first control amplicon, and (iv) a signaling probe labeled with a fluorophore and complementary to a second portion of the first control amplicon; and (b) a second internal control, comprising: (i) a second control sequence, (ii) a quencher probe labeled with a non-fluorescent quencher and complementary to a first portion of the second control sequence, and (iii) a self-quenching signaling probe having a fluorophore plus a non-fluorescent quencher and complementary to a second portion of the second control sequence; wherein background signal is emitted from the signaling probes when the signaling probes are not bound to the control sequence, wherein above background signal is emitted from the signaling probes when the signaling probes are bound to the control sequence but the quencher probes are not bound to the control sequence, and wherein the signal from the signaling probes is quenched by the non-fluorescent quencher of the quencher probe when the signaling probe and the quencher probe are bound to the control sequence. In some embodiments, the signaling probe of the first internal control and the signaling probe of the second internal control are labeled with the same fluorescent dye. In some embodiments, the Tm of the signaling and quencher probes of the first internal control and the Tm of the signaling and quencher probes of the second internal control differ by greater than 30° C. In some embodiments, the second internal control is a non-amplifiable control and does not require amplification primers. In some embodiments, the Tm of the signaling and quencher probes of the first internal control are at least 30° C. (e.g., >35° C., >40° C., >45° C., >50° C., >55° C., >60° C.) lower than the Tm of the signaling and quencher probes of the second internal control. In some embodiments, the Tm of the signaling and quencher probes of the second internal control are at least 30° C. (e.g., >35° C., >40° C., >45° C., >50° C., >55° C., >60° C.) lower than the Tm of the signaling and quencher probes of the first internal control. In some embodiments, a kit or reaction mixture further comprises: (c) a third internal control, comprising: (i) a third control sequence, (ii) a quencher probe labeled with a non-fluorescent quencher and complementary to a first portion of the third control sequence, and (iii) a signaling probe labeled with a fluorophore and complementary to a second portion of the third control sequence. In some embodiments, a kit or reaction mixture further comprises: (iv) primer pairs comprising excess and limiting primers for amplification of a single strand of all or a portion of the third control sequence to produce a third control amplicon. In some embodiments the signaling probe is a self-quenching probe having a fluorophore and a non-fluorescent quencher.

In some embodiments, the present invention provides methods of calibrating or controlling an instrument or reaction comprising: (a) providing one of the preceding kits or reaction mixtures in a single reaction vessel; (b) exposing the reaction vessel to conditions sufficient to permit single-strand amplification; (c) analyzing the signal from the signaling probes as a function of temperature. In some embodiments, steps (a)-(c) are simultaneously or serially in multiple reaction vessels.

In some embodiments, provided herein are reaction mixtures comprising: (a) a target nucleic acid; and (b) a hybridizing probe set comprised of three or more colored-sets of probe-pairs each probe-pair comprising: (i) a signaling probe labeled with a fluorescent moiety and complementary to a particular sequence within said target nucleic acid, and (ii) a quenching probe labeled with a non-fluorescent quencher moiety and complementary to a particular hybridization sequence within said target nucleic acid; wherein each signaling probe and its adjacent quenching probe comprise a probe-pair whose melting temperatures are distinct from the melting temperature of other probe-pairs; and wherein all probe-pairs whose signaling probes fluoresce in the same signaling color, comprise a colored-set of probe-pairs, and wherein: all probe-pairs within a colored-set hybridize to sequences within said target nucleic acid, and wherein: all probe-pairs within a colored-set do not hybridize to a contiguous sequences within said target nucleic acid. In some embodiments, each signaling probe has a melting temperature for the target sequence that is distinct from the other signaling probes of the three or more probe sets; wherein each quenching probe has a melting temperature for the target sequence that is distinct from the other quenching probes of the three or more probe sets. In some embodiments, hybridization sequences for the signaling probes are not linearly arranged within said target nucleic acid according to ascending or descending magnitude of melting temperatures, and/or the hybridization sequences for the quenching probes are not linearly arranged within said target nucleic acid according to ascending or descending magnitude of melting temperatures.

In some embodiments, one or more signaling probes of colored-set of probes, emit a background signal when not bound to the target sequence, wherein above background signal is emitted from the signaling probe when the signaling probe of a probe-pair is bound to the target sequence but the quencher probe of a probe-pair is not bound to the target sequence, wherein the signal from the signaling probe of a probe-pair is quenched by the non-fluorescent quencher of a probe-pair when both the signaling probe and the quencher probe are bound to the target sequence. In some embodiments, the signaling probes and the quenching probes are sufficiently complementary to their target nucleic acid sequences to hybridize under assay conditions as some temperature.

In some embodiments, for each colored-set, the melting temperature of the signaling probe in each probe-pair to the target nucleic acid is higher than the melting temperature of the quenching probe in the same probe-pair to its target sequence.

In some embodiments, the signaling probes are self-quenching probes that comprise a non-fluorescent quencher to reduce the signal from the fluorophore when the signaling probe is not hybridized to a target. In some embodiments, the signaling probes are molecular beacon probes. In some embodiments, the signaling probes comprise a target binding region and a non-binding region between the non-fluorescent quencher and the fluorescent fluorophore.

In some embodiments, the target nucleic acid is single stranded. In some embodiments, the target nucleic acid comprises a *Mycobacterium tuberculosis* nucleic acid sequence. In some embodiments, the target nucleic acid comprises a portion of the pncA gene.

In some embodiments, provided herein are homogeneous assay methods for analyzing at least one single-stranded nucleic acid target sequence in a sample, comprising: (a) forming a reaction mixture according to the preceding paragraph, wherein, for the probes of each probe set, a background signal is emitted from the signaling probe when the signaling probe is not bound to the target sequence, wherein above background signal is emitted from the signaling probe when the signaling probe is bound to the target sequence but the quencher probe of the same probe-pair is not bound to the target sequence, wherein the signal from the signaling probe is quenched by the non-fluorescent quencher when both the signaling probe and the quencher probe of a probe-pair are bound to the target sequence; (b) detecting a fluorescent signal from said fluorescent moiety of said signaling probes at a range of temperatures; and (c) analyzing hybridization of said probe sets to said at least one target sequence as a function of temperature.

In some embodiments, provided herein are kits or reaction mixtures comprising: (a) primers for the amplification of a target nucleic acid from a sample nucleic acid; and (b) a set of hybridizing probes comprised of three or more colored-sets of probe-pairs, each probe-pair comprising: (i) a signaling probe labeled with a fluorescent moiety and complementary to a particular hybridization sequence within said target nucleic acid, and (ii) a quenching probe labeled with a non-fluorescent quencher moiety and complementary to a particular hybridization sequence within said target nucleic acid; wherein each signaling probe has a melting temperature for the target sequence that is distinct from the other signaling probes of the same colored-set; wherein each quenching probe has a melting temperature for the target sequence that is distinct from the other quenching probes of the same colored-set; and wherein: (A) all probe-pairs whose signaling probes fluoresce in the same signaling color, comprise a colored-set of probe-pairs, and wherein: all probe-pairs within a colored-set hybridize to sequences within said target nuclei acid, and wherein: (B) all probe-pairs within a colored-set do not hybridize to a contiguous sequences within said target nucleic acid. In some embodiments, the hybridization sequences for the signaling probes are not linearly arranged within said target nucleic acid according to ascending or descending magnitude of melting temperatures, and/or the hybridization sequences for the quenching probes are not linearly arranged within said target nucleic acid according to ascending or descending magnitude of melting temperatures.

In some embodiments, a background signal is emitted from the signaling probe when the signaling probe is not bound to the target sequence, wherein above background signal is emitted from the signaling probe when the signaling probe is bound to the target sequence but the quencher probe of the same probe-pair is not bound to the target sequence, wherein the signal from the signaling probe is quenched by the non-fluorescent quencher when both the signaling probe and the quencher probe of the same probe-pair are bound to the target sequence. In some embodiments, the signaling probes and the quenching probes are sufficiently complementary to their particular nucleic acid target sequences so as to allow hybridization under assay conditions. In some embodiments, the target nucleic acid is single stranded.

In some embodiments, the target nucleic acid comprises a *Mycobacterium tuberculosis* nucleic acid sequence. In some embodiments, the target nucleic acid comprises a portion of the pncA gene. In some embodiments, for each probe-pair, the melting temperature of the signaling probe to the target nucleic acid is higher than the melting temperature of the quenching probe to the target sequence. In some embodiments, the signaling probes are self-quenching probes that comprise a non-fluorescent quencher to reduce the signal from the fluorophore when the signaling probe is not hybridized to a target. In some embodiments, the signaling probes are molecular beacon probes. In some embodiments, the signaling probes comprise a target binding region and a non-binding region between the non-fluorescent quencher and the fluorophore.

In some embodiments, the primers comprise a limiting primer and excess primer having the properties required for asymmetric PCR amplification. In some embodiments, the primers comprise a limiting primer and excess primer having the properties required for LATE-PCR amplification. In some embodiments, the primers comprise a limiting primer and excess primer having the properties required for LEL-PCR (Linear-Expo-Linear) amplification. In some embodiments, the kit or reaction mixture further comprises a target nucleic acid. In some embodiments, the primers are complementary to conserved regions of said target nucleic acid and flank a variable region of said target nucleic acid.

In some embodiments, provided herein are homogeneous assay methods for analyzing a sample target nucleic acid, comprising: (a) forming a reaction mixture according to the preceding paragraphs, wherein, for the signaling probes of each probe-pair, a background signal is emitted from the signaling probe when the signaling probe is not bound to the target sequence, wherein above background signal is emitted from the signaling probe when the signaling probe is bound to the target sequence but the quencher probe of the same probe-pair is not bound to the target sequence, wherein the signal from the signaling probe is quenched by the non-fluorescent quencher of the same probe-pair when both the signaling probe and the quencher probe are bound to the target sequence; (b) amplifying said sample nucleic acid with said primers to produce a target nucleic acid; (c) detecting a fluorescent signal from said fluorescent moiety of said signaling probes at a range of temperatures; and (d) analyzing hybridization of said probe sets to said at least one target sequence as a function of temperature. In some embodiments, a target-nucleic-acid-sequence-dependent fluorescence signature is generated.

In some embodiments, the target nucleic acid is single stranded. In some embodiments, the primers comprise an excess primer and a limiting primer, and said amplifying is by LATE-PCR.

In some embodiments, provided herein is a reaction mixture comprising: (a) a target nucleic acid; and (b) three or more probe-pairs, each probe-pair comprising: (i) a signaling probe labeled with a fluorescent moiety and complimentary to a particular hybridization sequence within said target nucleic acid, and (ii) a quenching probe labeled with a non-fluorescent quencher moiety and complimentary to a particular hybridization sequence within said target nucleic acid; wherein the hybridization sequences of the signaling probe and the quencher probe of a probe-pairare adjacent (e.g., without an intervening gap, contiguous, etc.) on said target nucleic acid; wherein at least two signaling probes within said three or more probe-pairsare labeled with a first fluorescent moiety, and at least one signaling probe within said three or more probe-pairsis labeled with a second fluorescent moiety; and wherein the hybridization sequences for the at least one probe-pair comprising the signaling probe labeled with a second fluorescent moiety is contiguous on the target nucleic acid with the hybridization sequences of two of the probe-pairs comprising signaling probes labeled with the first fluorescent moiety. In some embodiments, each signaling probe has a melting temperature for the target sequence that is distinct from all other signaling probes in the reaction mixture that are labeled with the same fluorescent moiety In some embodiments, for the probes of each probe-pair, a background signal is emitted from the signaling probe when the signaling probe is not bound to the target sequence, wherein above background signal is emitted from the signaling probe when the signaling probe is bound to the target sequence but the quencher probe is not bound to the target sequence, wherein the signal from the signaling probe is quenched by the non-fluorescent quencher when both the signaling probe and the quencher probe are bound to the target sequence. In some embodiments, the signaling probes and the quenching probes are sufficiently complementary to their particular hybridization sequences so as to allow hybridization under assay conditions. In some embodiments, the target nucleic acid is single stranded.

In some embodiments, the target nucleic acid comprises a *Mycobacterium tuberculosis* nucleic acid sequence. In some embodiments, the target nucleic acid comprises a portion of the pncA gene. In some embodiments, for each probe set, the melting temperature of the signaling probe to the target nucleic acid is higher than the melting temperature of the quenching probe to the target sequence. In some embodiments, the signaling probes are self-quenching probes that comprise a non-fluorescent quencher to reduce the signal from the fluorophore when the signaling probe is not hybridized to a target. In some embodiments, the signaling probes are molecular beacon probes. In some embodiments, the signaling probes comprise a target binding region and a non-binding region between the non-fluorescent quencher and the fluorescent dye.

In some embodiments, provided herein is a homogeneous assay method for analyzing at least one single-stranded nucleic acid target sequence in a sample, comprising (a) forming a reaction mixture of the preceding paragraph, wherein, for the probes of each probe-pair, a background signal is emitted from the signaling probe when the signaling probe is not bound to the target sequence, wherein above background signal is emitted from the signaling probe when the signaling probe is bound to the target sequence but the quencher probe is not bound to the target sequence, wherein the signal from the signaling probe is quenched by the non-fluorescent quencher when both the signaling probe and the quencher probe are bound to the target sequence; (b) detecting a fluorescent signal from said fluorescent moiety of said signaling probes at a range of temperatures; and (c) analyzing hybridization of said probe sets to said at least one target sequence as a function of temperature.

In some embodiments, provided herein are kits or reaction mixtures comprising: (a) primers for the amplification of a target nucleic acid from a sample nucleic acid; and (b) three or more probe-pairs, each probe-pair comprising: (i) a signaling probe labeled with a fluorescent moiety and complementary to a unique hybridization sequence within said target nucleic acid, and (ii) a quenching probe labeled with a non-fluorescent quencher moiety and complementary to a unique hybridization sequence within said target nucleic acid; wherein the hybridization sequences of the signaling probe and the quencher probe of a probe-pair are contiguous on said target nucleic acid (e.g., no nucleotide gap); wherein at least two signaling probes within said three or more probe pair are labeled with a first fluorescent moiety, and at least one signaling probe within said three or more probe-pairs is labeled with a second fluorescent moiety; and wherein the hybridization sequence for the at least one probe-pair comprising the signaling probe labeled with a second fluorescent moiety intervenes and is contiguous with on the target nucleic acid the hybridization sequences for two of the probe-pairs comprising signaling probes labeled with the first fluorescent moiety. In some embodiments, each signaling probe has a melting temperature for the target sequence that is distinct from all other signaling probes in the reaction mixture that are labeled with the same fluorescent moiety (e.g., in the same colored-set).

In some embodiments, provided herein are homogeneous assay methods for analyzing at least one sample nucleic acid, comprising: (a) forming a reaction mixture according to the preceding paragraph, wherein, for the probes of each probe-pair, a background signal is emitted from the signaling probe when the signaling probe is not bound to the target sequence, wherein above background signal is emitted from the signaling probe when the signaling probe is bound to the target sequence but the quencher probe is not bound to the target sequence, wherein the signal from the signaling probe is quenched by the non-fluorescent quencher when both the signaling probe and the quencher probe are bound to the target sequence; (b) amplifying said sample nucleic acid with said primers to produce a target nucleic acid; (c) detecting a fluorescent signal from said fluorescent moiety of said signaling probes at a range of temperatures; and (d) analyzing hybridization of said probe-pairs to said at least one target sequence as a function of temperature.

In some embodiments, provided herein are reaction mixtures comprising: (a) a target nucleic acid; (b) a first colored-set comprising a plurality of probe-pairs, each probe-pair of the first colored-set comprising: (i) a signaling probe comprising a first fluorescent moiety and complementary to a particular hybridization sequence within said target nucleic acid, and (ii) a quenching probe comprising a quencher moiety and complementary to a particular hybridization sequence within said target nucleic acid; wherein the hybridization sequences of the signaling probe and the quencher probe of a probe-pair are adjacent on said target nucleic acid; and (c) a second colored-set comprising a plurality of probe-pairs, each probe-pair of the second color set comprising: (i) a signaling probe comprising a second fluorescent moiety with excitation/emission spectra from said first fluorescent moiety, and complementary to a unique hybridization sequence within said target nucleic acid, and (ii) a quenching probe comprising a quencher moiety and complementary to a unique hybridization sequence within said target nucleic acid; wherein the hybridization sequences of the signaling probe and the quencher probe of each probe set in the first plurality of probe sets are adjacent on said target nucleic acid; wherein the hybridization sequences of the signaling probe and the quencher probe of each probe-pair are adjacent on said target nucleic acid; wherein the hybridization sequences of a first probe-pair from said first colored-set and the hybridization sequences of a second probe-pair from said first colored-set are intervened by and contiguous with the hybridization sequence of at least one probe-pair from the second colored-set. In some embodiments, for the probes of each probe-pair, a background signal is emitted from the signaling probe when the signaling probe is not bound to the target sequence, wherein above background signal is emitted from the signaling probe when the signaling probe is bound to the target sequence but the quencher probe is not bound to the target sequence, wherein the signal from the signaling probe is quenched by the non-fluorescent quencher when both the signaling probe and the quencher probe are bound to the target sequence. In some embodiments, the signaling probes and the quenching probes are sufficiently complementary to their particular hybridization sequences so as to allow hybridization under assay conditions. In some embodiments, the target nucleic acid is single stranded. In some embodiments, for each probe-pair, the melting temperature of the signaling probe to the target nucleic acid is higher than the melting temperature of the quenching probe to the target sequence. In some embodiments, the signaling probes are self-quenching probes that comprise a non-fluorescent quencher to reduce the signal from the fluorophore when the signaling probe is not hybridized to a target. In some embodiments, the signaling probes are molecular beacon probes. In some embodiments, the signaling probes comprise a target binding region and a non-binding region between the non-fluorescent quencher and the fluorescent dye. In some embodiments, the target nucleic acid comprises a *Mycobacterium tuberculosis* nucleic acid sequence. In some embodiments, the target nucleic acid comprises a portion of the pncA gene. In some embodiments, the nucleic acid sequences of probes are selected from nucleic acid sequences having at least 70% (e.g., <70%, <75%, <80%, <85%, <90%, <95%) sequence identity with nucleic acids selected from the group consisting of SEQ ID NOS: 65-102. In some embodiments, the reaction mixture further comprises: (d) a third colored-set comprising a plurality of probe-pairs, each probe-pair of the third colored-set comprising: (i) a signaling probe comprising a third fluorescent moiety with distinct excitation/emission spectra from said first fluorescent moiety and said second fluorescent moiety, and complementary to a particular hybridization sequence within said target nucleic acid, and (ii) a quenching probe comprising a quencher moiety and complementary to a particular hybridization sequence within said target nucleic acid; wherein the hybridization sequences of the signaling probe and the quencher probe of each probe-pair of the third colored-set are contiguous on said target nucleic acid; wherein the hybridization sequences of a first probe-pair from said third colored-set and the hybridization sequences of a second probe-pair from said third colored-set are intervened by and/or contiguous with at least one probe-pair from the first or second colored-sets. In some embodiments, the target nucleic acid comprises a *Mycobacterium tuberculosis* nucleic acid sequence. In some embodiments, the target nucleic acid comprises a portion of the pncA gene. In some embodiments, the nucleic acid sequences of the probes comprise at least 70% (e.g., <70%, <75%, <80%, <85%, <90%, <95%) sequence identity with nucleic acid sequences selected from the group consisting of SEQ ID NOS:65-102. In some embodiments, the probes are selected from the group consisting of SEQ ID NOS: 65-102.

In some embodiments, provided herein are homogeneous assay methods for analyzing at least one sample nucleic acid, comprising: (a) forming a reaction mixture described in the preceding paragraph, wherein, for the probes of each probe-pair, a background signal is emitted from the signaling probe when the signaling probe is not bound to the target sequence, wherein above background signal is emitted from the signaling probe when the signaling probe is bound to the target sequence but the quencher probe is not bound to the target sequence, wherein the signal from the signaling probe is quenched by the non-fluorescent quencher when both the signaling probe and the quencher probe are bound to the target sequence; (b) detecting a fluorescent signal from said fluorescent moiety of said signaling probes at a range of temperatures; and (c) analyzing hybridization of said probe-pairs to said at least one target sequence as a function of temperature.

In some embodiments, provided herein are reaction mixtures comprising: (a) a first target nucleic acid sequence; (b) a second target nucleic acid sequence; (b) a first colored-set comprising a plurality of probe-pairs, each probe-pair comprising: (i) a signaling probe comprising a first fluorescent moiety and complementary to a particular hybridization sequence within said first target nucleic acid sequence or said second target nucleic acid sequence, and (ii) a quenching probe comprising a quencher moiety and complementary to a particular hybridization sequence contiguous with the particular hybridization sequence of the signaling probe of the probe set; and (c) a second colored-set comprising a plurality of probe-pairs, each probe-pair comprising: (i) a signaling probe comprising a second fluorescent moiety with excitation/emission spectra from said first fluorescent moiety, and complementary to a particular hybridization sequence within said first target nucleic acid sequence or said second target nucleic acid sequence, and (ii) a quenching probe comprising a quencher moiety and complementary to a particular hybridization sequence contiguous with the unique hybridization sequence of the signaling probe of the prob-pair; wherein the hybridization sequences for at least one probe-pair from each of said first colored-set and said second colored-set are within said first target nucleic acid sequence, and wherein the hybridization sequences from at least one probe-pair from each of said first colored-set and said second colored-set are within said second target nucleic acid sequence. In some embodiments, each of said colored-sets comprises three or more probe sets.

In some embodiments, provided herein are reaction mixtures comprising: (a) a target nucleic acid; (b) a first colored-set of nucleic acid probes, the probes of which are complementary to hybridization sequences within the target nucleic acid; wherein the first colored-set comprises three or more probe-pairs, wherein each probe-pair comprises a signaling probe labeled with a first fluorophore and a quenching probe labeled with a quencher moiety; and wherein the signaling and quenching probes of each probe-pair are contiguous on the target nucleic acid; and (c) a second colored-set of nucleic acid probes, the probes of which are complementary to hybridization sequences within the target nucleic acid; wherein the second colored-set comprises three or more probe-pairs, wherein each probe-pair comprises a signaling probe labeled with a second fluorophore and a quenching probe labeled with a quencher moiety; and wherein the signaling and quenching probes of each probe-pair are contiguous on the target nucleic acid; wherein the hybridization sequences of at least one probe-pair from the first colored-set intervene and are contiguous with particular hybridization sequences of two probe-pairs from the second colored-set. In some embodiments, reaction mixtures further comprise: (d) a third colored-set of nucleic acid probes, the probes of which are complementary to hybridization sequences within the target nucleic acid; wherein the third colored-set comprises three or more probe-pairs, wherein each probe-pair comprises a signaling probe labeled with a third fluorophore and a quenching probe labeled with a quencher moiety; and wherein the signaling and quenching probes of each probe-pair are contiguous on the target nucleic acid; wherein the hybridization sequences of at least one probe-pair from the third colored-set intervene and are contiguous with particular hybridization sequences of two probe-pairs from either the second colored-set or the first colored-set. In some embodiments, reaction mixtures further comprise a fourth colored-set, fifth colored-set, sixth colored-set, etc.

DEFINITIONS

Figure 1:
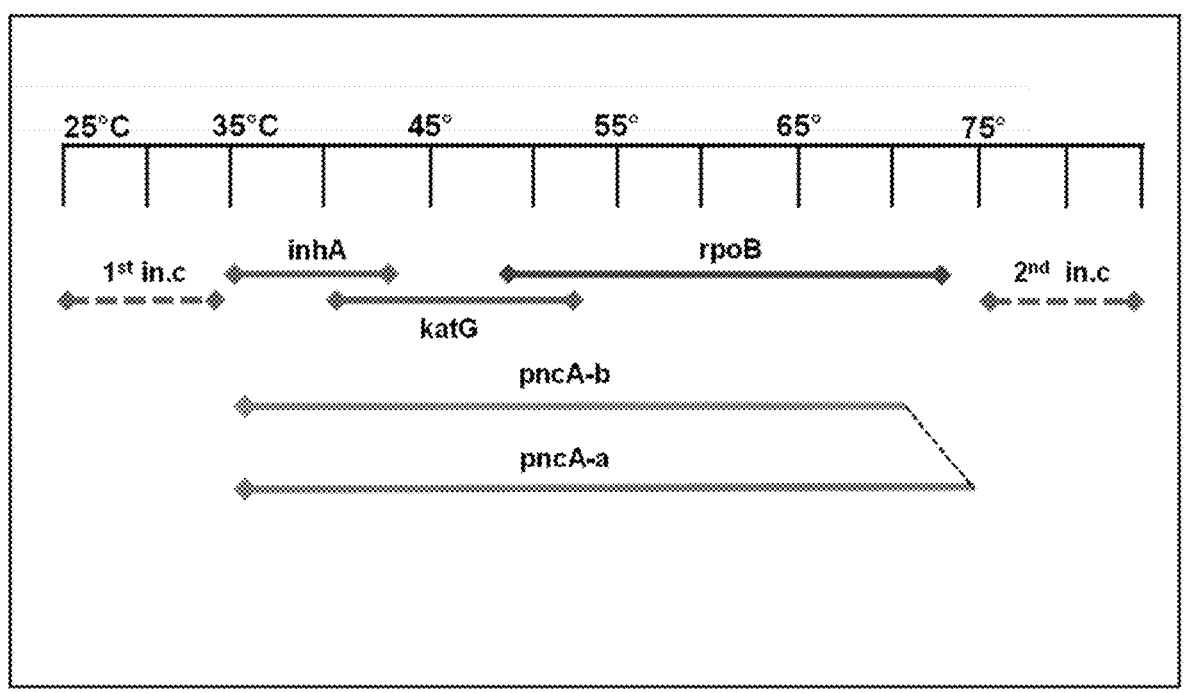
FIG. 1 shows an exemplary assay design for single-tube, single-color, LATE PCR detection of multi/extensive drug-resistant tuberculosis (M/XDR-TB).
Figure 2:
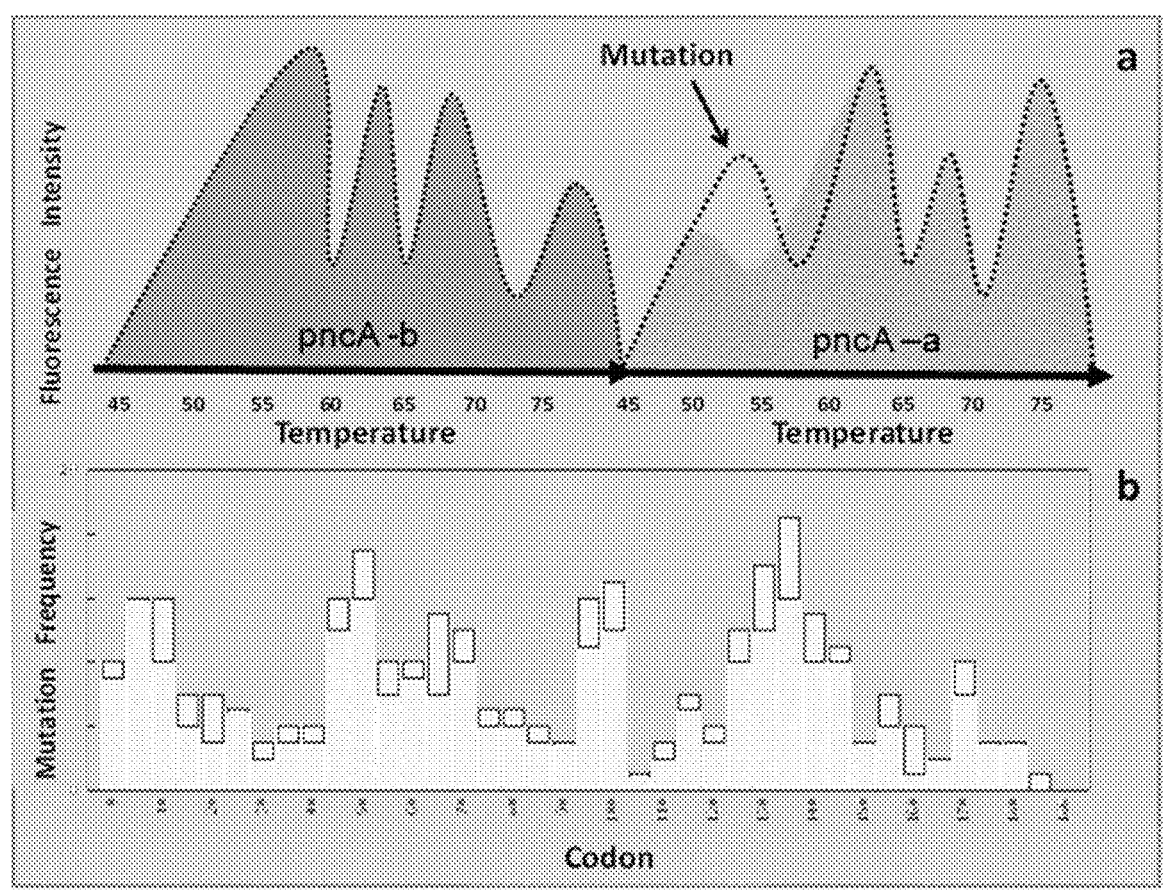
FIG. 2 shows a schematic for pncA gene mutation detection assay in two colors.
Figure 3:
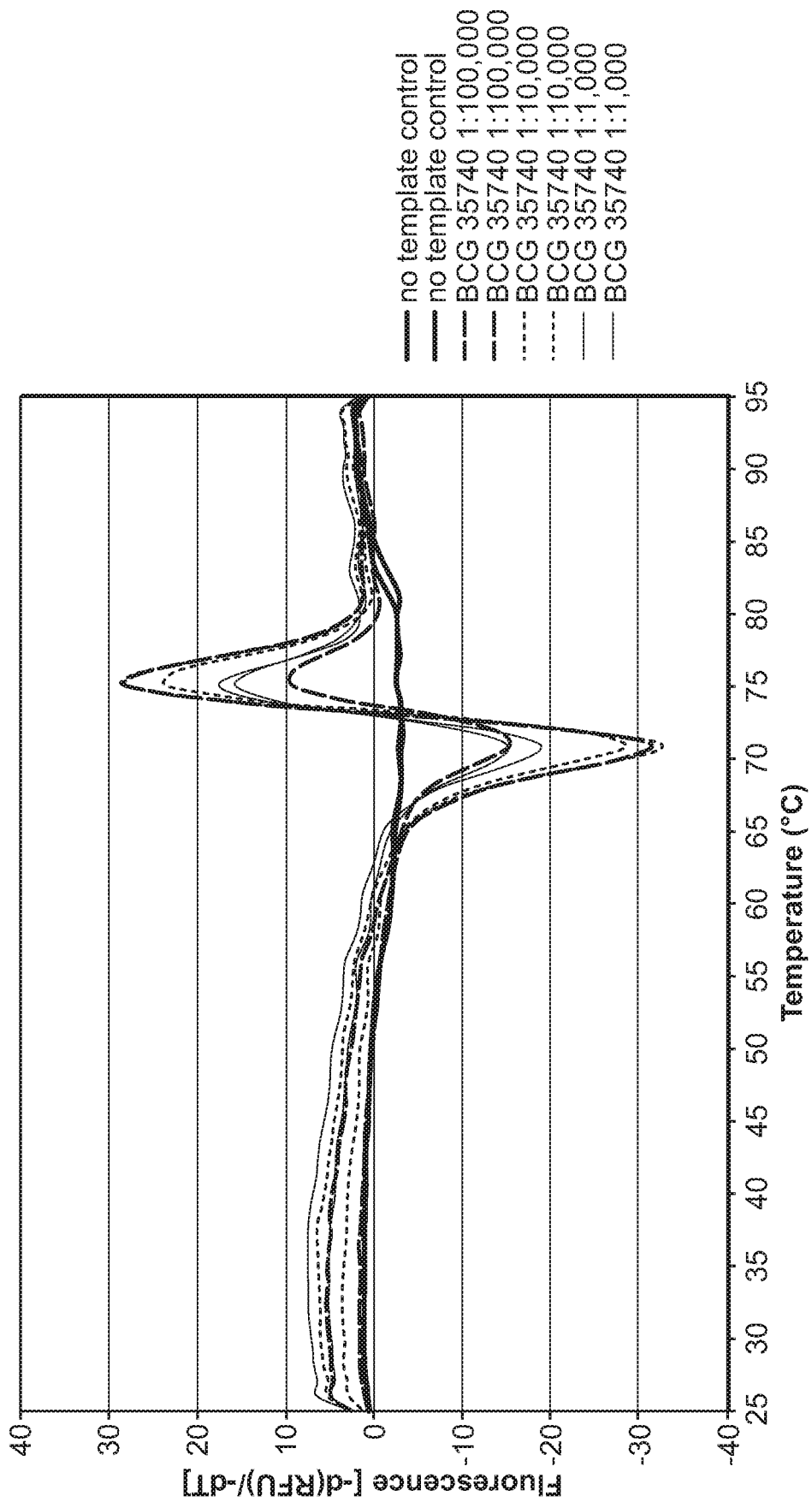
FIG. 3 shows a fluorescent signature obtained of an *M. bovis* sample across three tenfold range of concentrations with no template control, using 100 nM pncA_probe 406_427 ON_Bovis (SEQ ID NO: 44) and 300 nM pncA_probe_428_448_OFF (SEQ ID NO: 45) probes.
Figure 4:
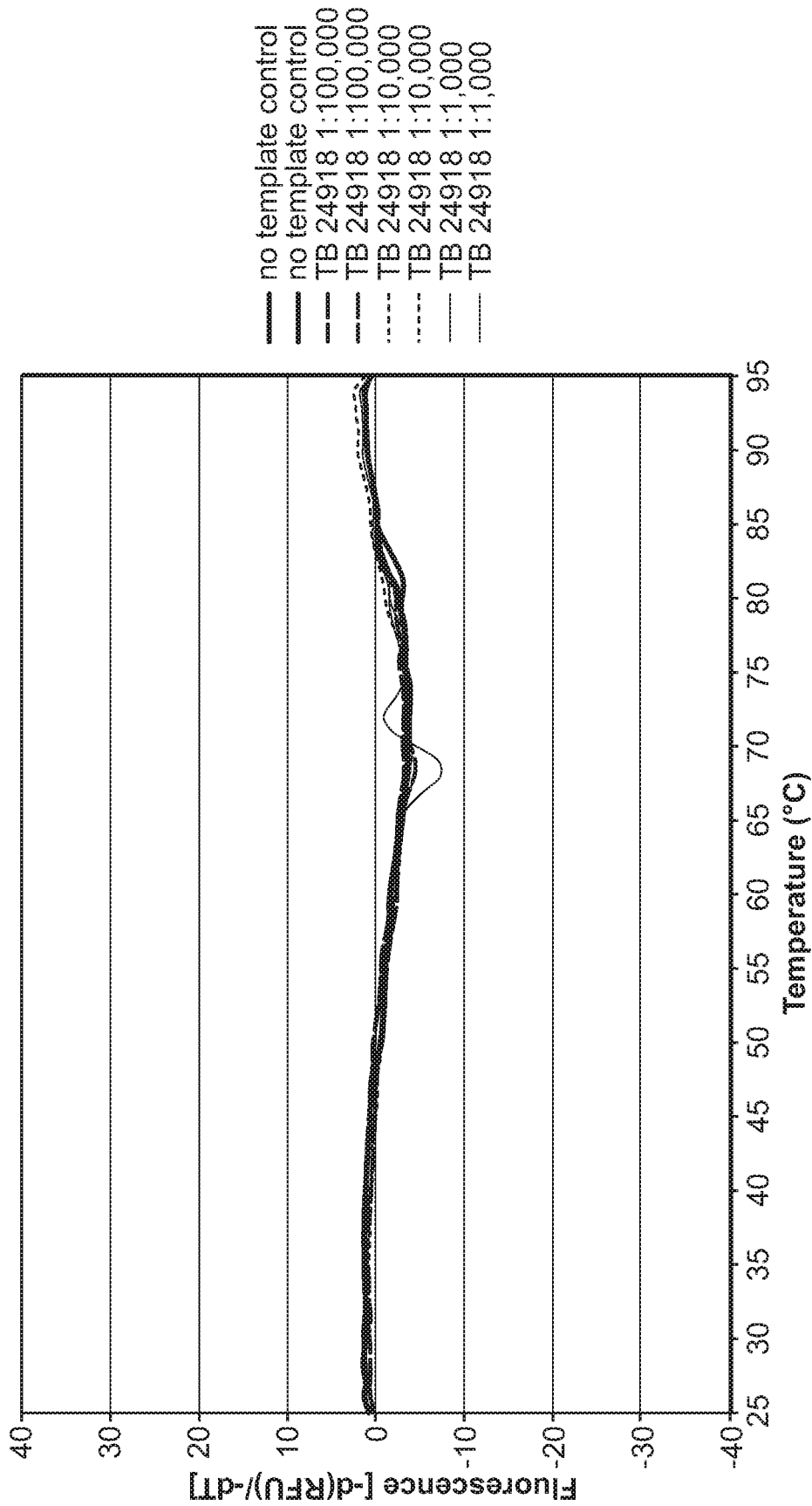
FIG. 4 shows a fluorescent signature obtained of an *M. tuberculosis* sample across three tenfold range of concentrations with no template control, using 100 nM pncA_probe 406_427 ON_Bovis (SEQ ID NO: 44) and 300 nM pncA_probe_428_448_OFF (SEQ ID NO: 45) probes.
Figure 5:
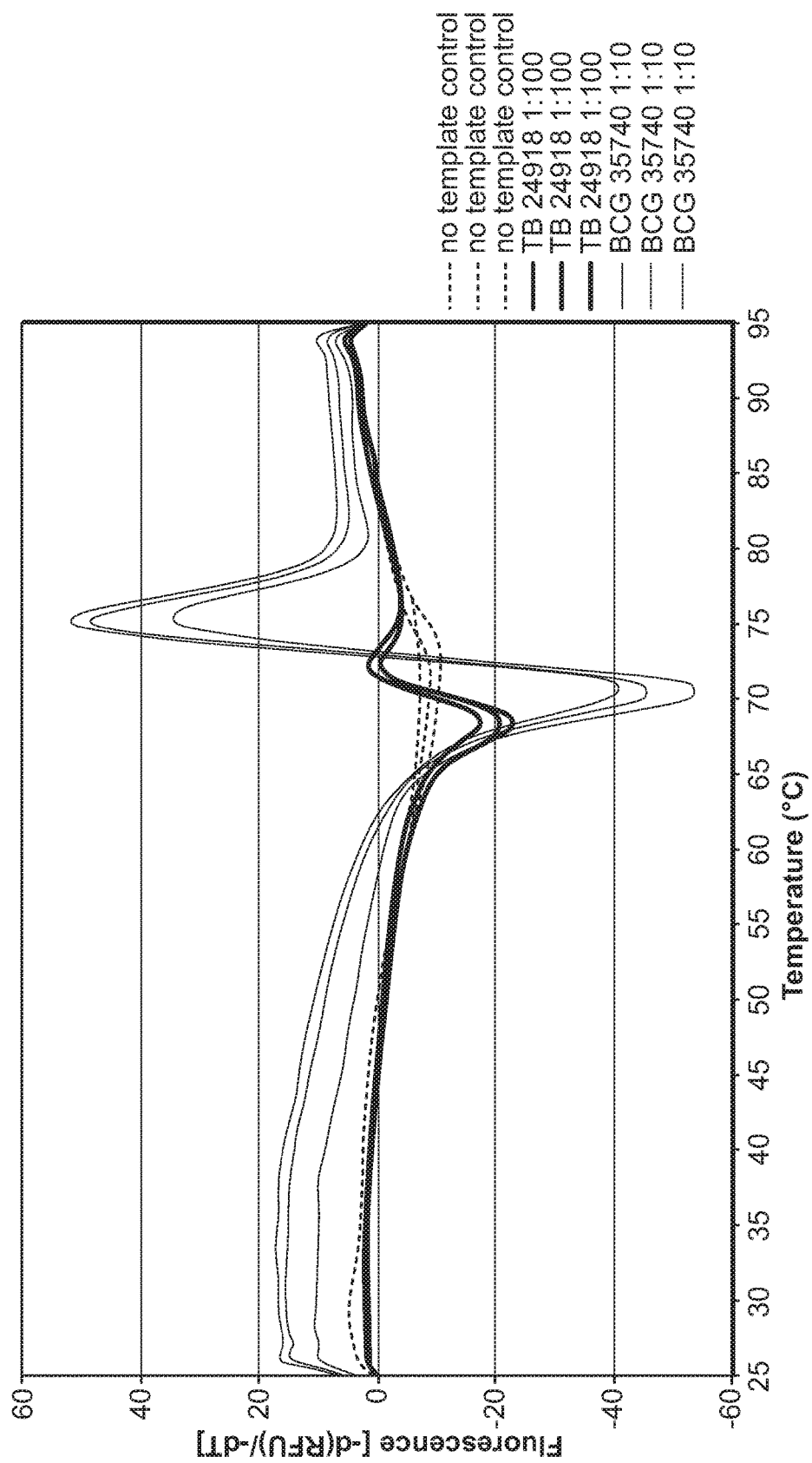
FIG. 5 shows a comparison of the fluorescent signature of a *M. bovis, M. tuberculosis*, an no-template control, using 200 nM pncA_probe

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to a delivery system comprising two or more separate containers that each contains a subportion of the total kit components. The term "kit" includes both fragmented and combined kits.

As used herein, the term "reaction mix" or "reaction mixture" refers to a combination of reagents (e.g., nucleic acids, enzymes, fluorophores, buffers, salts, etc.) in solution in a single vessel (e.g., microcentrifuge tube, PCR tube, well, microchannel, etc.).

The term "sample" is used herein in its broadest sense. It is meant to include: a specimen or culture (e.g., microbiological cultures), a prepared solution or mixture, and both biological and environmental samples. Biological samples may be animal, including human, or microbiological. Biological samples may take the form of a fluid or solid, and may be obtained from any suitable biological source. Environmental samples include environmental material such as surface matter, soil, plants, and water. These examples are not to be construed as limiting the sample types applicable to the present invention.

As used herein, the term "gene" refers to a nucleic acid (e.g., DNA) sequence that comprises coding sequences necessary for the production of a polypeptide or precursor (e.g., katG, rpoB, inhA promotor, pncA, etc.). The term "gene" encompasses both cDNA and genomic forms of a gene.

As used herein, the term "target specific," when used in reference to an oligonucleotide reagent, as in, for example "target-specific probe" or "target-specific primer," refers to reagents designed and produced for hybridization to a specific target sequence (e.g., for detection, characterization, or amplification of the target sequence). A target-specific reagent may be allele discriminating or mismatch tolerant.

As used herein, the term "internal control" or "IC" refers to a nucleic acid molecule (e.g., plasmid, oligonucleotide, etc.) which is co-amplified and/or co-detected in the same vessel as one or more target sequences. The IC may be mixed in a reaction mixture to monitor the performance of amplification and/or detection, avoid false results, and/or calibrate reactions. An IC may be amplified with primers for a target or with IC-specific primers. An IC is typically detected with IC-specific probes.

As used herein, the term "amplifiable internal control" refers to a non-target nucleic acid molecule (e.g., plasmid, oligonucleotide, etc.) that is amplifiable by PCR or other amplification methods (e.g., isothermal amplification (e.g., rolling circle). Typically, amplification primers and detection probes for such a control are provided.

As used herein, the term "non-amplifiable internal control" refers to a non-target nucleic acid molecule (e.g., plasmid, oligonucleotide, etc.) for which detection probes but not amplification primers are provided.

As used herein, the term "melting temperature" or "Tm" refers to the temperature at which a population of hybridized nucleic acid molecules becomes half dissociated into single strands. Equations for calculating the Tm of nucleic acids is well known in the art. For example, a "concentration-adjusted melting temperature" of a probe or primer to its target may be calculated using, for example, a Nearest Neighbor method (See SantaLucia (1998) Proc. Natl. Acad. Sci. USA 95:1460-1465; Allawi, H. T. and SantaLucia (1997) Biochem. 36:10581-10594; herein incorporated by reference in their entireties). More accurate estimates of oligonucleotide Tm in PCR buffers can be made using software programs (e.g. Visual OMP, version 7.5.0.0, DNA Software Inc., Ann Arbor, Mich.) or on-line programs (e.g. The DINAMelt Web Server) that use a modification of the Nearest Neighbor formula that calculate the effect of magnesium concentration on Tm. Preferably, Tm is measured empirically (U.S. Pat. Pub. No. 2004/0053254; herein incorporated by reference in its entirety).

As used herein, the term "overlapping" applies to temperature ranges, when the signals produced by signaling probes that hybridize over the respective temperature ranges produce detectably additive signal.

As used herein, the term "target sequence" or "target nucleic acid sequence" refers to a region of nucleic acid (e.g., an amplicon) to be analyzed by the methods described herein. The term "hybridization sequence" refers to a portion of a target sequence that is sufficiently complementary to a probe ("probe hybridization sequence") or primer ("primer hybridization sequence") to allow hybridization of the probe or primer under assay conditions. The hybridization sequences may include nucleotides that are not complementary with the corresponding nucleotides in the primer or probe, as long as hybridization is capable of occurring under assay conditions. A single target sequence may contain multiple hybridization sequences, for example, aligned adjacently so as to cover every nucleotide of the target sequence (although in some embodiments a target sequence may comprise gaps between hybridization sequences). A single amplicon or other nucleic acid may contain a single target sequence or may contain multiple non-adjacent target sequences.

As used herein, the term "fluorescent moiety" refers to a compound or other moiety that can be attached to an oligonucleotide, and is excited by electromagnetic radiation and emits electromagnetic radiation in response in an amount sufficient to be detected in an assay. The skilled artisan will understand that a fluorescent moiety absorbs and emits over ranges of wavelengths, referred to as an "absorbance spectrum" and an "emission spectrum." A fluorescent moiety will exhibit a peak emission wavelength that is a longer wavelength than its peak absorbance wavelength. The term "peak" refers to the highest point in the absorbance or emission spectrum.

As used herein, the terms "quencher" or "quencher moiety" refer to a compound or moiety that absorbs energy from an excited donor compound or moiety. For example, the quencher moiety may function by absorbing fluorescent photons emitted by a donor fluorophore, thereby masking the donor's fluorescence.

As used herein, the term "signaling probe" refers to an oligonucleotide probe labeled with a fluorescent moiety and having sufficient complementarity to a hybridization sequence on a etarget nucleic acid, so as to hybridize to the hybridization sequences with separate melting temperatures between about 30° C. and about 80° C. In the embodiments described herein, a fluorescent moiety is typically attached to the 5' or 3' end of the signaling probe. In addition to the fluorescent moiety, a signaling probe may further comprise a second fluorescent moiety or a quencher moiety (e.g., at the opposing end from the first fluorescent moiety).

As used herein, the terms "quenching probe" and "quencher probe" refer to an oligonucleotide probe labeled with a quencher moiety and having sufficient complementarity to a hybridization sequence on a target nucleic acid, so as to hybridize to the hybridization sequences with separate melting temperatures between about 30° C. and about 80° C. In addition to the quencher moiety, a quencher probe may further comprise a second fluorescent moiety or a quencher moiety (e.g., at the opposing end from the first fluorescent moiety).

As used herein, the terms "probe set" or "probe-pair" refer to a pair of labeled nucleic acid oligonucleotides having sufficient complementarity to adjacent hybridization sequences on a target nucleic acid so as to hybridize to the hybridization sequences with separate melting temperatures between about 30° C. and about 80° C. A probe-pair comprises a signaling probe and a quenching probe; although one or both the probes in a probe-pair may be shared probes (below). Typically, the signaling probe of a probe-pair emits above background fluorescence when it is hybridized to its hybridization sequence and the quenching probe is not. When both probes of a probe-pair are bound to their hybridization sequences, the quencher of the quenching probe quenches the fluorescence from the fluorophore of the signaling probe.

As used herein, the term "shared probe" refers to a probe that is part of two adjacent probe-pairs. When hybridized to its hybridization sequence, the label (e.g., fluorescent moiety or quencher moiety) on the 5' end of the probe interacts with the label of a probe of a first probe-pair and the label (e.g., fluorescent moiety or quencher moiety) on the 3' end of the probe interacts with the label of a probe of a second probe-pair. The shared probe typically comprises two quencher moieties (which interact with fluorophores of adjacent signaling probes), or a fluorescent moiety (which interacts with a quencher moiety of an adjacent quencher probe) and a quencher moiety (which interacts with a fluorescent moiety of an adjacent singling probe). The shared probe is said to be part of both probe-pairs. A shared probe may be a signaling probe in a first probe-pair and a quenching probe in a second probe-pair, or a quenching probe in two different probe-pairs.

As used herein, the "colored-set" refers to three or more probe-pairs having hybridization sequences within the same target nucleic acid or set of target nucleic acids, the signaling probes of each of the probe-pairs of the colored-set being labeled with the same fluorescent moieties and/or quencher moieties.

As used herein, the term "hybridizing set of probes" refers to two or more different colored-sets (e.g., each colored-set has a distinct fluorescent moiety), the hybridization sequences of the probe-sets of which are within the same target nucleic acid or set of target nucleic acids.

As used herein in reference to nucleic acid sequences and/or probe binding sites, the terms "contiguous" and "adjacent" refer to two or more sequences or nucleic acid segments without intervening nucleotides (e.g., gaps) between them (i.e., the 3' nucleotide of a first hybridization sequence is linked via a phosphodiester bond with the 5' nucleotide of a second hybridization sequence). For example, if 'sequence X' and 'sequence Y' are contiguous, then there are no nucleotides separating those sequences. Likewise, if the hybridization sequences for 'probe 1' and 'probe 2' are contiguous, then there are no nucleotides intervening those hybridization sequences.

As used herein in reference to nucleic acid sequences and/or probe binding sites, the term "intervening" and other forms there of (e.g., "intervened by") refers to one sequence or nucleic acid segment located between two other nucleic acid segments. For example, if 'sequence A' and 'sequence C' are intervened by 'sequence B', then sequence B is between sequences A and C. An intervening sequence may be, but is not necessarily, contiguous with the sequences it is between.

DETAILED DESCRIPTION

Provided herein are reagents and kits for analysis of nucleic acid target sequences in a single-tube, multi-probe assay, and methods of use thereof. In particular embodiments, multiplex assays are provided, for example, for the detection of *Mycobacterium tuberculosis* complex target sequences (e.g., katG, rpoB, inhA promotor, pncA, etc.). One or more target sequences may be analyzed using multiple probes labeled with a single type of fluorophore (e.g., single color), or in a multi-color assay. The probe descriptions (e.g., lengths, labels, melting temperatures, etc.), assay protocols, controls, and other reagents, methods, etc. described herein apply to single-target and multi-target, single-color and multi-color, multiplex and monoplex, and/or Design I and Design II assays.

In certain embodiments, provided herein are reagents and kits for detection of multiple target sequences in a single-tube, single-color assay, and methods of use thereof. In particular embodiments, multiplex assays are provided for the detection of *Mycobacterium tuberculosis* complex target sequences (e.g., katG, rpoB, inhA promotor, pncA, etc.). For example, a single-tube, single-color, tetraplex assay is provided for the detection of *Mycobacterium tuberculosis* complex target sequences (e.g., katG, rpoB, inhA promotor, etc.), for example, together with a $1^{st}$ (amplifiable) internal control target sequence. The four single-stranded products of this tetraplex are detected using sets of probes labeled with a fluorophore in one color. These reaction components can also include a second (non-amplifiable) control, also labeled in the same color (or labeled in a different color). The use of such reagents and methods with other detection and characterization assays (e.g., detection of the Mycobacterial pncA gene with an additional color) is also provided herein. In some embodiments, provided herein are multiplex (e.g., multicolor) assays for the detection and/or characterization of, for example, the Mycobacterial pncA gene.

In some embodiments, provided herein are reagents and kits for detection of one or more target sequences in a single-tube, multi-color assay, and methods of use thereof. In particular embodiments, monoplex and multiplex assays are provided for the detection of *Mycobacterium tuberculosis* complex target sequences (e.g., pncA, etc.) or other target sequences (e.g., long sequences requiring multiple probe sets). For example, a single-tube, multi-color, monoplex assay is provided for the detection of the *Mycobacterium tuberculosis* complex target sequence pncA. A single-stranded target amplicon is detected using sets of probes labeled with multiple fluorophores (e.g., grouped (Design I), or mixed (Design II) probe sets).

In some embodiments, provided herein are assays to detect/identify/characterize multiple nucleic acid target sequences in a single reaction vessel. In some embodiments, probe sets and primer pairs are provided for the amplification and detection of 3 or more, 4 or more, 5 or more, 6 or more, 7 or more, 8 or more, 9 or more, 10 or more (e.g., 10, 11, 12, 13, 14, 15, or more) targets in a single vessel and using a single color of fluorophore. In some embodiments, target sequences are identified in the presence of multiple possible target sequences (e.g., non-target sequence, near-target sequences (e.g., >90% identity to target, >95% identity to target, >98% identity to target, >99% identity to target), etc.) in a sample. In some embodiments, methods and reagents allow the discrimination of various target variants, wherein variant target sequences comprise a variable sequence flanked by conserved or at least relatively conserved sequences. In particular embodiments, single-stranded versions of target sequences and/or target sequence variants are generated by an amplification method that generates single-stranded amplicons, for example, a non-symmetric polymerase chain reaction (PCR) method, such as Linear-Expo-Linear (LEL)-PCR, or most preferably Linear-After-the Exponential (LATE)-PCR. In some embodiments, only a few pairs of primers, generally not more than three pairs, preferably not more than two pairs and more preferably only a single pair of primers are used for any one target (e.g., even if a number of target variants may be present). Target-specific primers (e.g., excess and limiting) hybridize to the sequences flanking the region of interest (e.g., species, sub-species, and/or resistance identifying region). In some embodiments, a probe-pair (e.g., signaling and quencher probes) is provided that hybridizes to the amplified region. In particular embodiments, the signal generated by the temperature-dependent hybridization of the signaling and quencher probes to the target (e.g., over a temperature range) identifies the target sequence as present in the sample and/or distinguishes between variant versions of the target sequence (e.g., a resistance mutation). In typical embodiments, primer pairs and probe sets are provided (e.g., in a single kit or reaction volume) that are each specific to different target sequences. Such embodiments allow for the temperature-dependent detection and/or characterization of multiple targets within a single sample, in a single vessel and/or reaction. In some embodiments, all probe sets in a reaction or kit comprise the same detectable label (e.g., fluorophore), and the methods described herein allow for single-color detection/characterization of multiple targets in a single vessel and/or reaction.

Figure 17:
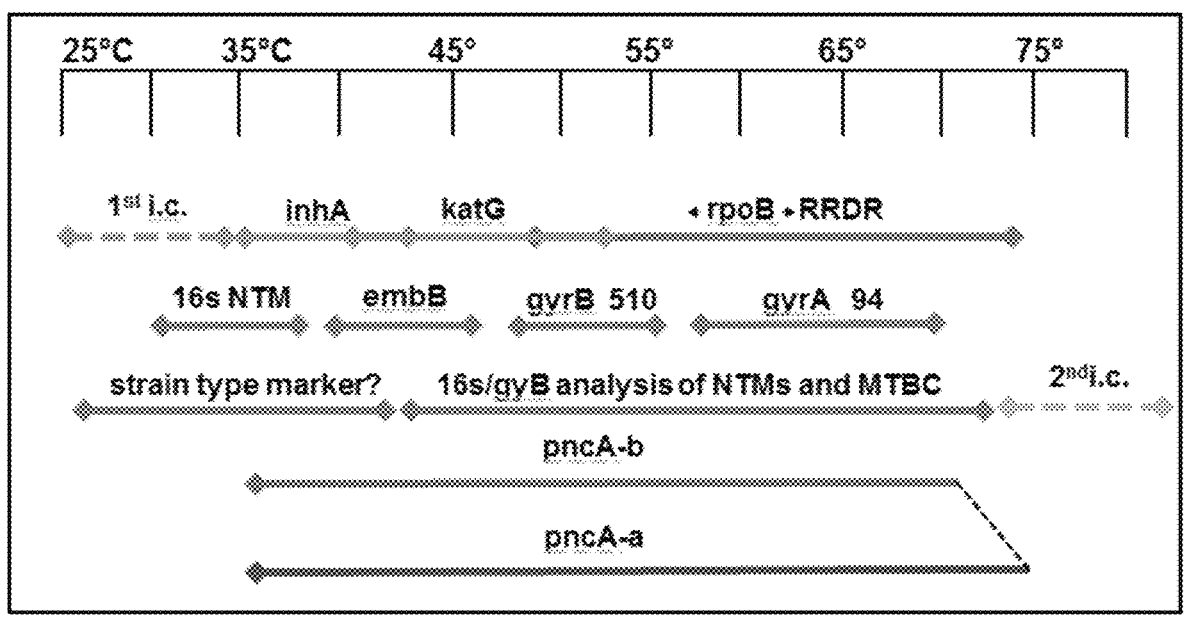
Figure 18:
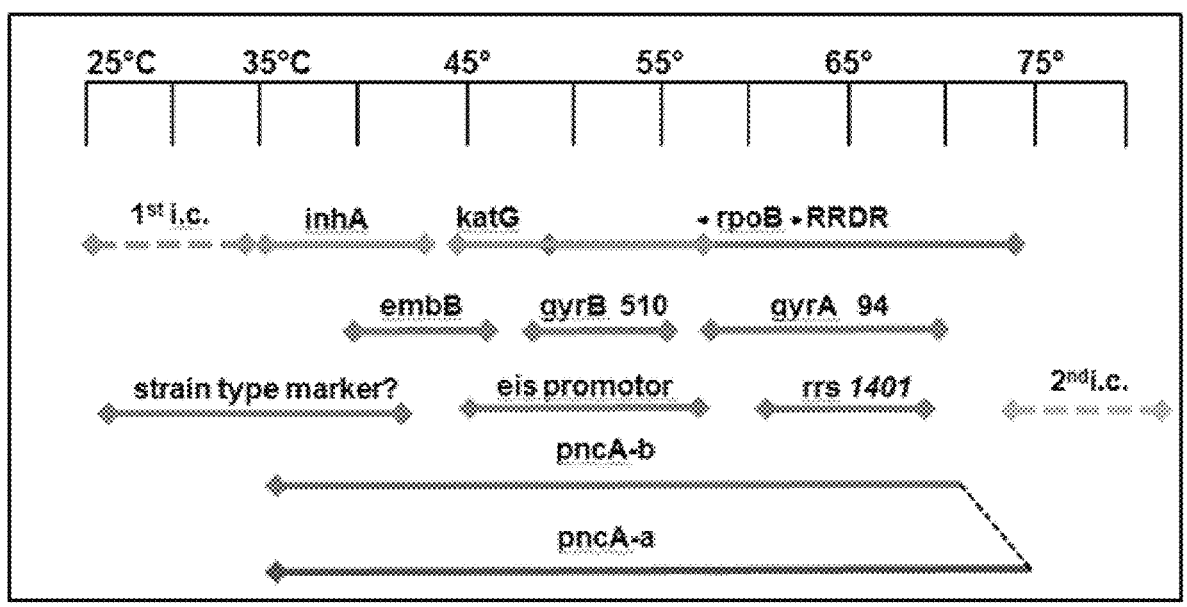
Figure 19:
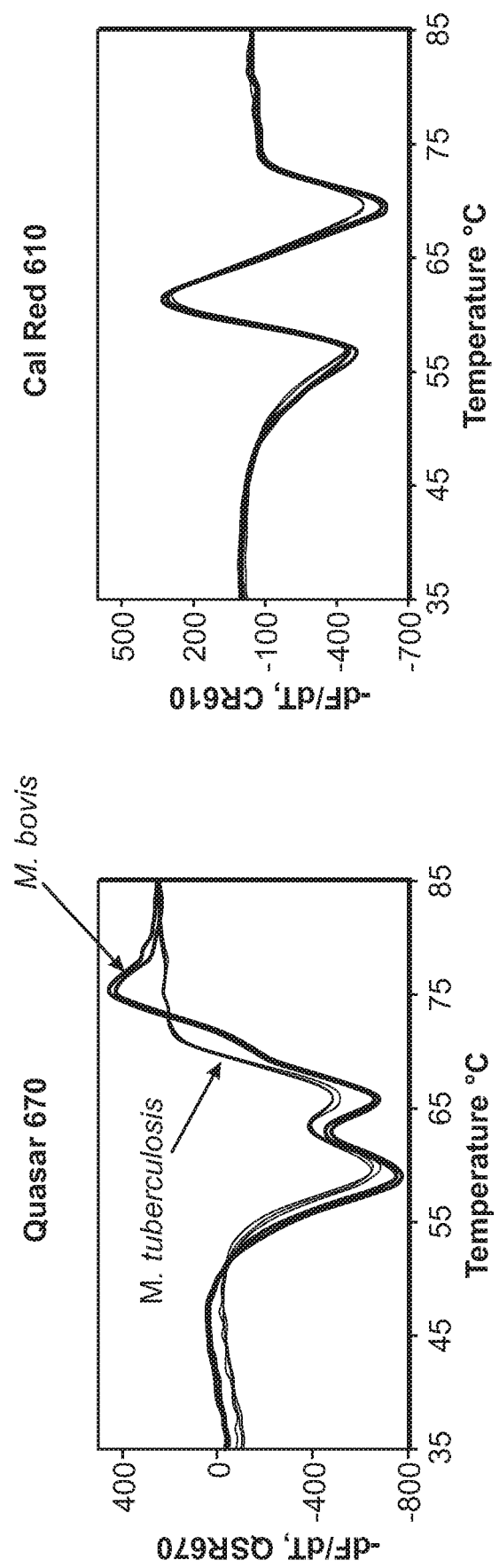
Figure 20:
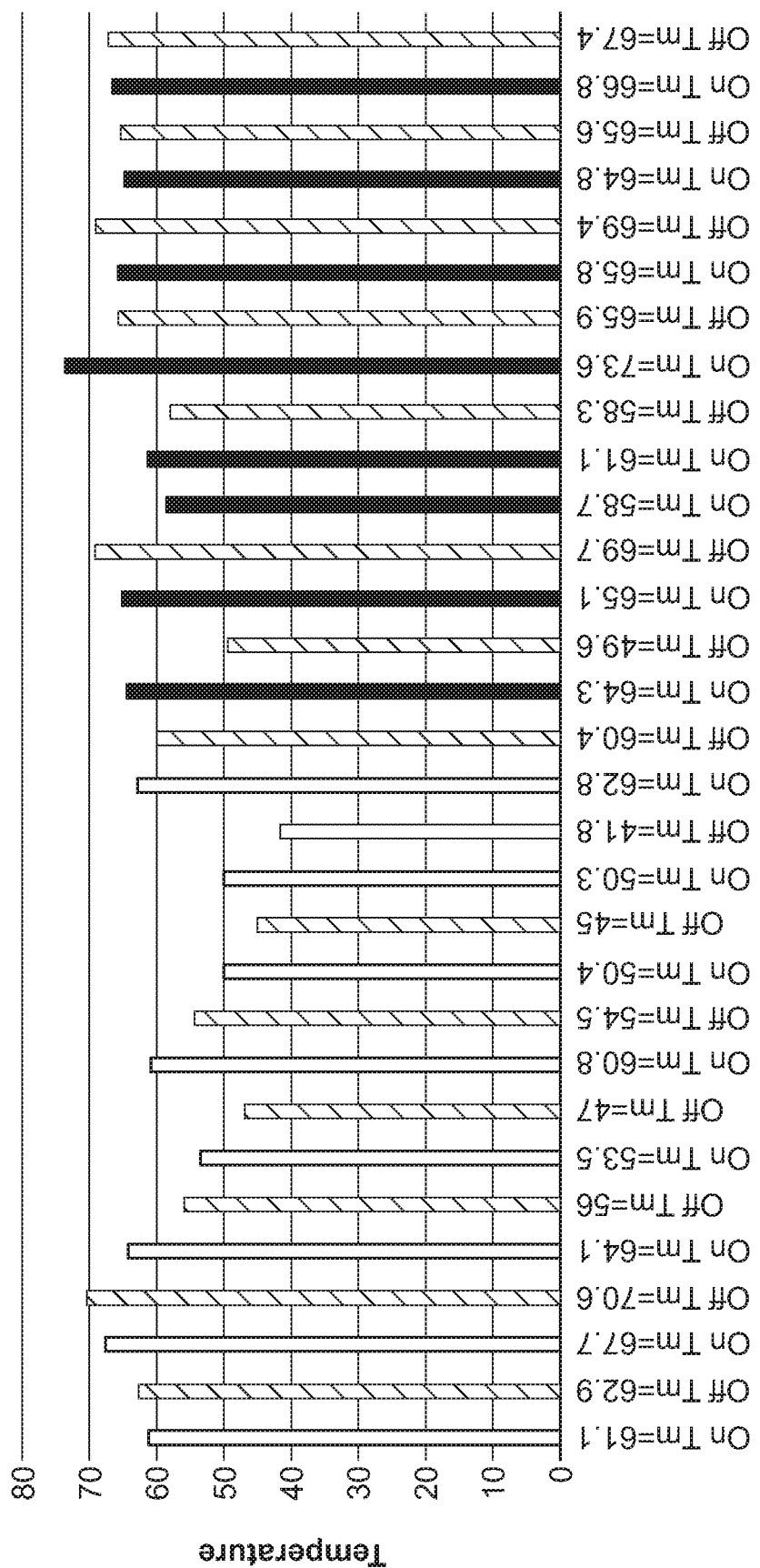
Figure 21:
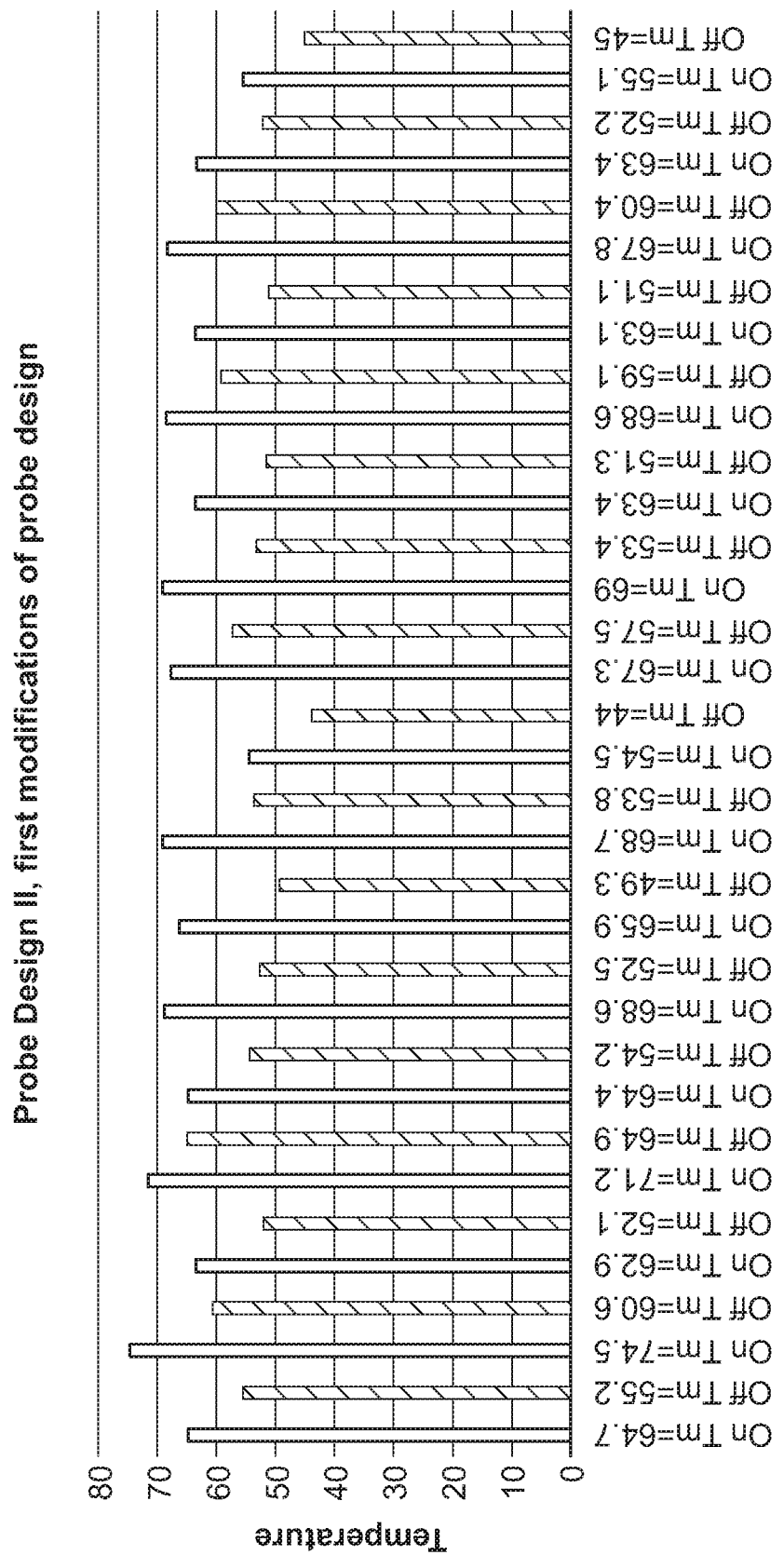
Figure 22:
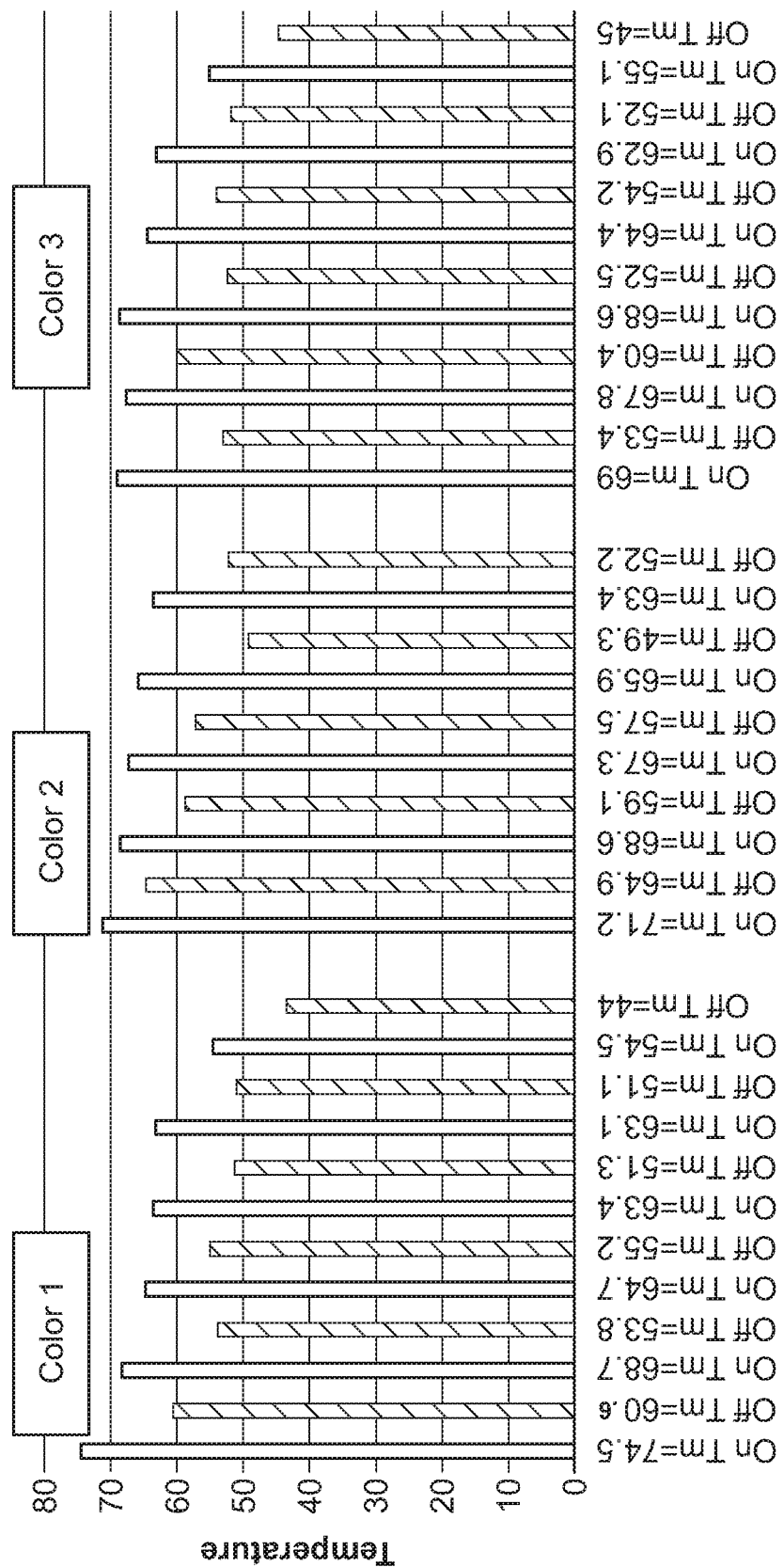
Figure 23:
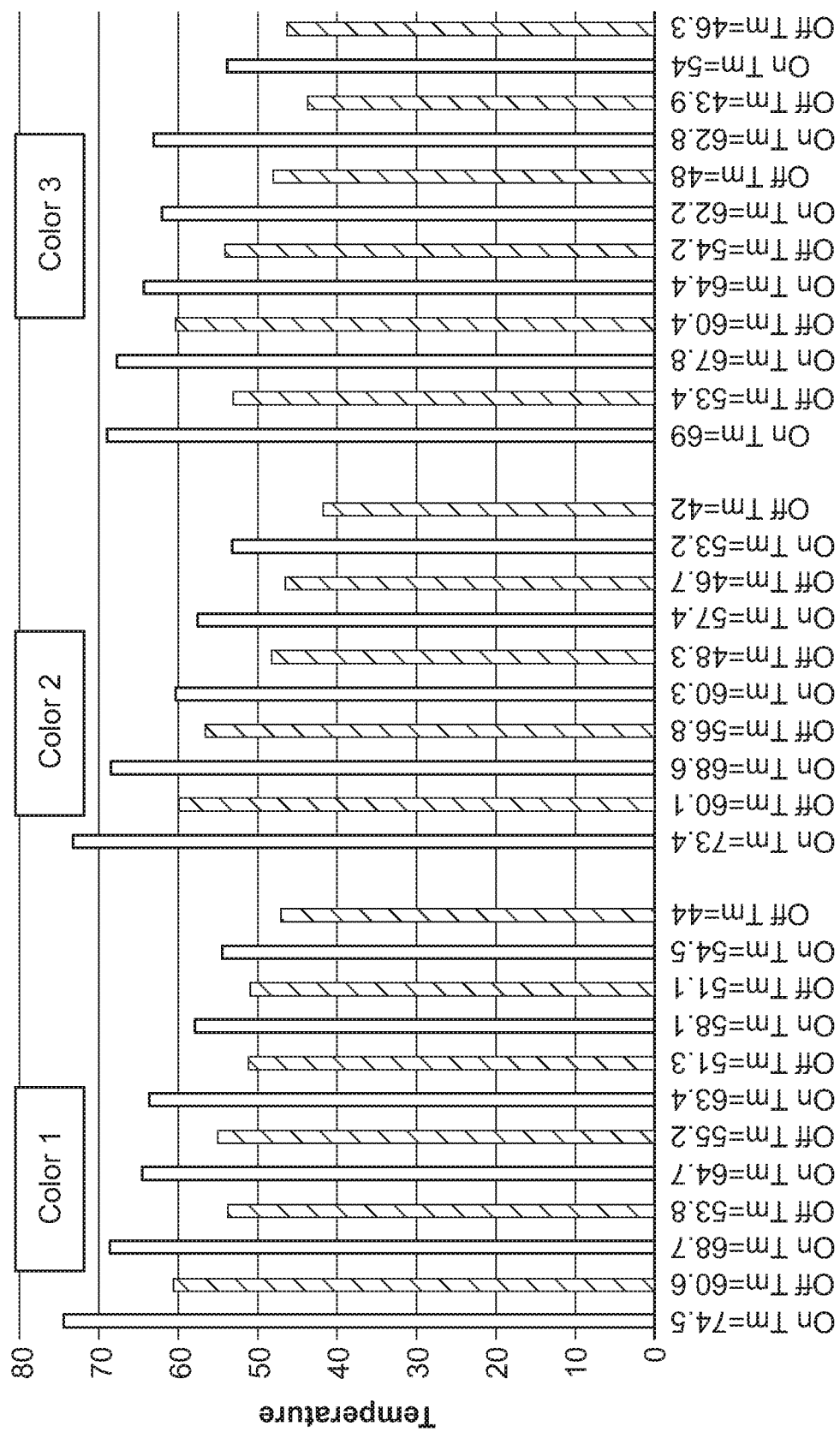

In some embodiments, single color assays described herein are combined with other assays (e.g., utilizing other detection methods or utilizing one or two additional color fluorophores) for detection of TB and/or additional pathogens. In some embodiments, multiple different single-color (muti-target) assays are combined into a single vessel (See, e.g., FIGS. 17 and 18). In some embodiments, multi-color assays are provided (e.g., Design I and Design II assays).

In particular embodiments, the present invention provides reagents and methods for the detection, differentiation, and/or characterization of the *Mycobacterium tuberculosis* complex, including, but not limited one or more of *Mycobacterium tuberculosis*, *Mycobacterium africanum*, *Mycobacterium bovis*, *Mycobacterium caprae*, *Mycobacterium microti*, *Mycobacterium mungi*, *Mycobacterium orygis*, *Mycobacterium pinnipedii*, and *Mycobacterium canettii*. Methods and reagents described herein allow for identification of the species, strain, and/or subspecies, characterization of drug resistance/susceptibility, and/or determination of nation/region or origin. In particular embodiments, primers and probes are provided for the amplification, detection, and characterization of portions of the katG, rpoB, inhA promotor, pncA, mabA, embB, rpsL, rss, gyrA, gyrB, eis, tlyA, and/or 16s rDNA genes. In particular embodiments, primers and probes are provided for the amplification, detection, and characterization of portions of the katG, rpoB, inhA promotor, and/or pncA genes (e.g., the portions defined by the primers herein). In some embodiments, variants of those genes are identified that confer various drug resistances (e.g., isoniazid resistance (katG/inhA promotor), rifampicin resistance (rpoB), ethionamide resistance (inhA promotor), pyrazinamide resistance (pncA), etc.). In some embodiments, primers and probes are provided that are capable of distinguishing all allelic variants (e.g., all known variants, known and unknown variants) of a target (e.g., all variants of rpoB codons 516, 526, 531, and 533).

In some embodiments, probe-pairs (e.g. signaling and quencher probes) are configured to hybridize to a target sequence (e.g., a variable sequence located between conserved primer binding sequences) and to differentiate between multiple target sequences (e.g. in a single sample or mixture) (See, e.g., FIG. 14). In some embodiments, the signaling and quencher probes hybridize with different Tm to nearby or adjacent portions of the target sequence. Signal from the signaling probe increases as it hybridizes to the target, the signal is then quenched as the quench probe hybridizes to its adjacent target. Alternatively, signal from the background level of a signaling probe decreases when it hybridizes to the target adjacent to an already bound quencher probe. In some embodiments, multiple probe sets are designed with different hybridization temperature ranges (See, e.g., FIG. 1) such that the hybridization to multiple targets can be discriminated in a single tube with a single color. In some embodiments, one or both probes of a probe set (e.g. signaling and/or quencher probes) comprise different degrees of complementarity to the variable regions of the different target sequences. In some embodiments, a signaling probe and/or quencher probe is configured to hybridize to the variable sequence (e.g. overlapping the actual sequence difference) of multiple target sequences (e.g. with different Tm to the different target sequences). In some embodiments, a signaling probe is configured to hybridize to the variable sequence of multiple target sequences (e.g. with different Tm to the different target sequences). In some embodiments, a quencher probe is configured to hybridize to the variable sequence of multiple target sequences (e.g. with different Tm to the different target sequences).

In certain embodiments, provided herein are reagents and kits for detection of one or more target sequences in a single-tube, multi-color assay (e.g., two color, three color, four color, or more), and methods of use thereof. In some embodiments, multiple colors are utilized due to the length of a target or targets, and/or the difficulty of spanning the target(s) with probe sets differentiated by melting temperature alone (e.g., as in a single color assay). To overcome the problem of resolving the number of probe sets needed to cover a target or targets, two or more groups of probe sets are employed, each group having a distinctly labeled signaling probes (e.g., each group of probe sets defined by its own 'color'), and having probes spanning the available melting temperature space. By utilizing two, three, or more colors, the same temperature space (e.g., probe melting temperatures for the target of between about 10° C. and about 80° C.) can be utilized two, three, or more times in the same assay in PCR devices with the appropriate heating and cooling capacites. In particular embodiments, assays (e.g., multiplex, monoplex, etc.) are provided for the detection of *Mycobacterium tuberculosis* complex target sequences (e.g., pncA, etc.).

In some embodiments, probe sets of a first color are assigned to one target or one portion of a target (e.g., a first contiguous portion of a target), probe sets of a second color are assigned to a second target or second portion of a target, etc. (e.g., for a third color of probe sets, fourth color of probe sets, etc.). In such, embodiments, the fluorescence spectrum of the first color correlates to the sequence of the first target or portion of a target; changes in the first spectrum can be assigned to changes in that sequence. Likewise, the fluorescence spectrum of the second color correlates to the sequence of the second target or portion of a target, and changes in the second spectrum can be assigned to changes in that sequence; and so on for third colors, fourth colors, etc. In some embodiments, in addition to grouping probe sets by color, the group is arranged along the target or portion of target in descending or ascending order of melting temperature. Therefore, as the fluorescence spectrum for a color moves from low to high, it corresponds to movement through the corresponding target sequence or portion of target sequence from one end to the other (e.g., 5' to 3' or 3' to 5'). In some embodiments, probes and probe sets grouped on a target sequence according to label color and/or aligned within a color group according to magnitude of melting temperature are designed according to a 'Design I' design process (See below).

In some embodiments probe-pairs, comprised of a signaling probe having a first color, second color, third color etc. plus a quenching probe for each signaling probe, bind in pairs throughout a target or targets (e.g., colors are interspersed). In such, embodiments, the fluorescence spectrum of the first color correlates to sequence changes at various locations throughout the target or targets. Likewise, the fluorescence spectrum of the second color correlates to sequence changes at various locations throughout the target or targets, and so on for additional colors. But the particular probe target sequences within a color are not grouped along the target sequence(s). Nevertheless, the probe target sequences are arranged according to ascending or descending probe/target melting temperatures within a color. Therefore, as the melting temperatures of probe-pairs within a color move from low to high, the corresponding particular target sequences are found at non-contiguous locations along the target sequence or sequences. In some embodiments, correlation of changes in a fluorescence spectrum to sequence changes requires comparison to a key or to control spectrum or spectra (e.g., because the color of the spectrum and/or temperature along the spectrum do not correlate to a specific region of the target). In some embodiments, probes and probe-pairs that are not grouped on a target sequence according to label color, and/or are not aligned within a color group according to magnitude of melting temperature, are designed according to a 'Design II' design process (See below).

In some embodiments, the probing and analysis methods provided herein apply to samples containing single-stranded nucleic acid target(s). Methods of this invention include analysis of a single sequence, analysis of two or more sequences in the same strand, analysis of sequences in different strands, and to combinations of the foregoing. A single-stranded nucleic acid target sequence may be a control sequence added to a sample. A nucleic acid target sequence may be DNA, RNA or a mixture of DNA and RNA. It may come from any source. For example, it may occur naturally, or the target sequence may occur in double-stranded form, in which case the single-stranded target sequence is obtained by strand separation and purification, or a single-strand amplification method (e.g., LEL-PCR or LATE-PCR). If the single-stranded nucleic acid target sequence is a cDNA sequence, it is obtained from an RNA source by reverse transcription.

In many instances a natural source will not contain a target sequence in sufficient copy number for probing and analysis. In such instances the single-stranded target sequence is obtained by amplification, generally an amplification method that includes exponential amplification. Useful amplification methods include isothermal amplification methods and thermal cycling amplification methods. The amplification reaction may generate the single-stranded nucleic acid target sequence directly, or it may generate the target sequence in double-stranded form, in which event the single-stranded target sequence is obtained by strand separation and purification, as stated above. Useful amplification methods that may be employed include, the polymerase chain reaction (PCR), including symmetric PCR, asymmetric PCR, LEL-PCR and LATE-PCR, any of which can be combined with reverse transcription for amplifying RNA sequences, NASBA, SDA, TMA, and rolling circle amplification. If the single-stranded nucleic acid target sequence is a cDNA sequence, the amplification method will include reverse transcription, for example, RT-PCR. In some embodiments, when non-symmetric amplification is utilized, probe sets are included in the amplification reaction mixture prior to amplification to avoid contamination.

Probe sets useful in methods provided herein include a signaling probe and an associated quencher probe. The signaling probe is a hybridization probe that emits a detectable signal, preferably a fluorescent signal, when it hybridizes to a single-stranded nucleic acid target sequence in a sample, wherein the signal is quenchable by the nearby (e.g., adjacent) hybridization of the associated quencher probe. The quencher probe does not emit visible light energy. Generally, a signaling probe has a covalently bound fluorescent moiety. Signaling probes include probes labeled with fluorophores or other fluorescent moieties. In some embodiments, preferred signaling probes are dual-labeled probes; that is, probes that emit little or no signal when in solution and not bound to target, even if stimulated, but emit a signal when they hybridize to a single-stranded nucleic acid sequence (e.g., in the absence of an adjacently bound quencher). For example, when the probe is in solution, it assumes a conformation (e.g., random coil, etc.) wherein the quencher randomly interacts with the fluorophore, and the probe emits a low level of fluorescence (e.g., completely dark (e.g., >90% quenched, >95% quenched, >98% quenched, >99% quenched, or more), or partially darkened (e.g., <80% signal, <70% signal, <60% signal, <50% signal, <40% signal, <30% signal, <20% signal, <10% signal, or less)). When the probe hybridizes to its target, however, it is forced into a conformation (e.g., open conformation, stable conformation, etc.) in which the fluorophore is physically separated from the quencher, and the probe signals.

In quenched signaling probes (e.g., self-quenching probes), quenching may be achieved by any mechanism, typically by FRET (Fluorescence Resonance Energy Transfer) between a fluorophore and a non-fluorescent quenching moiety or by contact quenching. In some embodiments, preferred signaling probes are dark or very nearly dark in solution (e.g., not hybridized) to minimize background fluorescence. In other embodiments, the quenching moiety only partially quenches the fluorophore when in solution (e.g., <95%, <90%, <80%, <70%, <60%, <50%, <40%, <30%, >10%, >20%, >30%, >40%, >50%, >60%, >70%, >80%, etc.). In some embodiments, quenching is achieve be contact quenching or FRET quenching. In some embodiments, the distance between a quenching moiety and signaling moiety is extended by inclusion of a non-binding region within the probe (e.g., a portion of the probe that is not complementary to the target, for example a polyA tract). By extending the sequence between the quenching moiety and signaling moiety, the additional sequences decrease the amount of signal quenching in solution.

The quencher probe of a probe set is or includes a nucleic acid strand that includes a non-fluorescent quencher. The quencher can be, for example, a non-fluorescent chromophore such a dabcyl or a Black Hole Quencher (Black Hole Quenchers, available from Biosearch Technologies, are a suite of quenchers, one or another of which is recommended by the manufacturer for use with a particular fluorophore). In some embodiments, preferred quenching probes include a non-fluorescent chromophore. In some embodiments, quenchers are Black Hole Quenchers (e.g., BHQ2). The quencher probe of a set hybridizes to the single-stranded nucleic acid target sequence adjacent to or near the signaling probe such that when both are hybridized, the quencher probe quenches, or renders dark, the signaling probe (e.g., >80% quenched, >85% quenched, >90% quenched, >95% quenched, >98% quenched, >99% quenched). Quenching may be by fluorescence resonance energy transfer (FRET or FET) or by contact (e.g., "collisional quenching" or "contact quenching").

In some embodiments, various controls (e.g., control probes, control primers, control plasmids, etc.) are provided. In some embodiments, internal controls (e.g., co-amplified and/or co-detected with the target(s) in a single container) are provided. In some embodiments, internal controls are non-target sequences (e.g., highly conserved sequences) within the sample nucleic acid (e.g., M. tuberculosis genome, non-target portion of a target gene, etc.) that are amplified with control-specific primers, and detected with control-specific probes. In some embodiments, internal controls are nucleic acid molecules (e.g., oligonucleotides, plasmids, etc.) that are provided as a reagent along with primers and probes for their amplification and detection. In some embodiments, internal controls are non-target sequences (e.g., highly conserved sequences) within the sample nucleic acid (e.g., M. tuberculosis genome, non-target portion of a target gene, etc.) that are not amplified (e.g., no appropriate primers are provided), but are detected with control-specific probes. In some embodiments, internal controls are nucleic acid molecules (e.g., oligonucleotides, plasmids, etc.) that are not amplified (e.g., no appropriate primers are provided), but are detected with control-specific probes (e.g., known concentration). In some embodiments, control probes comprise the same fluorophore as target probes. In other embodiments, control probes comprise the different fluorophores from the target probes. In some embodiments, a control comprises a pair of oligonucleotides, one or both of which are end-labeled with a fluorophore and or quencher (See, e.g., U.S. Pro. App. No. 61/755,872; herein incorporated by reference in its entirety). In such embodiments, the fluorescent signal from the control oligonucleotides is altered (e.g., quenched or unquenched) as the oligonucleotides melt apart. The signal from such a control is useful as the Tm is precisely known and normalizes the melting curves, for example, if there is a variation due to instrumentation or sample variation (e.g., introducing high salt concentrations with the sample). In some embodiments, the double stranded reagent also interacts with the polymerase during PCR and improves amplification specificity.

In some embodiments, controls are provided with differing probe hybridization temperatures (e.g., a high temperature control and a low temperature control). In certain embodiments, probe hybridization temperatures are more extreme than any target hybridization temperatures. In certain embodiments the two controls can signal in the same color or in different colors. Such controls allow for calibrating the temperature scale and any fluorescent signatures within that temperature span. A control sequence may be a single stranded oligonucleotide, double stranded oligonucleotide pair, a plasmid, etc.

In some embodiments, control probe concentrations are relatively low (e.g., 50 nM for ON probe, 150 nM for OFF probe) compared to target probes. In such embodiments, the low control-probe concentration reduces background fluorescence from the control reagents in the target-detection temperature range. In other embodiments, control probe concentrations are equal to or higher than the target concentrations. In such embodiments, the magnitude of the control peak provides a measure of the overall efficiency with which the target sequence was recovered and amplified in each sample. In some embodiments, both the amplitude of a control peak and the depth of the control valley are used as constants for comparison with the amplitudes of the target peaks and valleys of the rest of the signature (e.g., provides a means of quantifying the amount of the unknown signal). In some embodiments, control probes are at concentrations in excess of the final amplicon concentration (e.g. above 500 nM) in order to quantify the amplicon, for example, to test the efficiency with which target molecules recovered during sample preparation and subsequently amplified. In some embodiments, control probes are at limiting concentrations (e.g 50 nM or 100 nM) to provide a consistent signal in all samples regardless of variations in the efficiency of target recovery during sample preparation and subsequent amplification.

In some embodiments, a control is a low temperature hybridization control. In some embodiments, a synthetic nucleic acid (e.g., control plasmid, control oligo, etc.) is designed to allow detection of probe hybridization (e.g. signaling and quenching) at low temperature (<35° C., <30° C., <25° C., <20° C., <15° C., <5° C., >10° C., >15° C., >20° C., ranges therein). In some embodiments, the low temperature hybridization range for the control allows measurement (e.g., quantitative) of the control without interfering with target detection which occurs at higher temperatures. The Low Tm of the control provides a signal at a predetermined low temperature. In certain embodiments, it cannot be assumed that every position in a thermal cycler works exactly the same, nor that calibration at a high temperature is also accurate for low temperature. Thus, in some embodiments, a Low-Tm control along with a High Tm control allows for dual temperature calibration in each reaction. Dual temperature calibration in the absence of genomic targets can also be carried out prior to or after analysis of samples. This is useful for routine maintenance of the machine and the resulting data can even be analyzed at a distance (i.e. anywhere in the world via a "cloud" connection). Calibration reflects the functioning of both the thermal cycler and the optical system of the device. Fluorophores emitting at different wavelengths may be affected differently by experimental and equipment variations, making multiple controls useful. Further, certain impurities that may be present in a sample or instrument absorb light of different wavelengths differently. Thus, if the Low-Tm and the High-Tm internal controls are designed to fluoresce at different wavelengths, the ratio of their signal intensities (as well as their actual temperatures) can be analyzed. If the optical system is dirty the signal from the fluorophore which is sensitive to the impurity will be impacted more than the fluorophore which is insensitive (less sensitive) to impurity and the ratio of the values will change.

In some embodiments, reagents and methods described herein find use in calibration of instruments (e.g., thermocycler, plate reader, fluorimeter, high-throughput robotic platform, etc.), calibration of reaction conditions, or as controls for use with other assays not described herein. In some embodiments, calibration or control kits are provided, for example, comprising control sequences (e.g., plasmids, oligonucleotides, etc.), primers, probes, and any other useful reagents (e.g., enzymes, buffers, etc.). In particular embodiments, a high Tm control (e.g., a control with a Tm of hybridization of probe to control sequence of greater than 60° C. (e.g., >65° C., >70° C., >75° C.)) and a low Tm control (e.g., a control with a Tm of hybridization of probe to control sequence of less than 40° C. (e.g., <35° C., <30° C., <25° C., <20° C., <15° C.)) are provided. In some embodiments, one or both of the internal controls are non-amplifiable (e.g., probes provided but no primers). In some embodiments, one or both of the internal controls are amplifiable (e.g., probes and primers provided). In some embodiments, one or more additional intermediate Tm controls (e.g., amplifiable or non-amplifiable) are provided. Calibration kits and method within the scope of the invention are not limited by the combinations of controls described herein. Any suitable combination (e.g., 2 internal controls, 3 internal controls, 4 internal controls, or more) of the controls described herein (e.g., high Tm, low Tm, amplifiable, non-amplifiable, etc.). In some embodiments, amplification and detection of such controls allows a user, including a user at a substantial distance to monitor and calibrate and instrument and/or perform quality control over time.

Variation in salt concentrations, (e.g., due to carryover from sample preparation) as well as other variations in reagents or equipment can change the empirical Tm of hybridization probes, but may affect probes differently. For example a long, GC-rich, or completely complementary probe may display a greater or lesser change in Tm compared to a probe that is short, AT-rich or partially complementary. It is useful, therefore, to have controls in both the higher and lower ranges of the temperature space that is used for detection. The relative change in fluorescence maxima (or minima) of the controls relative to standard conditions can be measured and expressed as a factor of temperature. Adjustments to fluorescence at intermediate temperatures then can be made using normalization factors that vary with temperature, as would be apparent to those knowledgeable in the art.

The design of quality Low-Tm probes (considered here to have empirical Tm no higher than 40° C., and preferred versions no higher than 30° C.) includes criteria that are not generally required (or at least not considered) for High-Tm probes. The single-stranded target to which the probe hybridizes should have limited secondary structure (e.g., hairpin formation at the detection temperature). As temperature is lowered, the potential for hairpin formation increases. If hairpins are present that have Tm several degrees above that of the probe/target hybrid, that nucleotide region has reduced availability for probe hybridization, will slow the rate of hybridization and probe signals may be limited. In some embodiments of this invention, target regions are selected from endogenous sequences that are predicted to be free of hairpins having Tm above that of probe/target hybrid. In some preferred embodiments, predicted hairpin Tm are no higher than 5 degrees below the predicted Tm of the hybrid. Such predictions can be made using software programs such as Visual OMP, version 7.5.0.0 (DNA Software, Ann Arbor, Mich., USA). Sequences can be altered to a limited extent during amplification by the use of primers with mismatches to the targets, as is well known by those experienced in the art. Some of the potential for specific hairpin formation can be reduced using such mismatched primers to generate a modified sequence.

Figure 15:
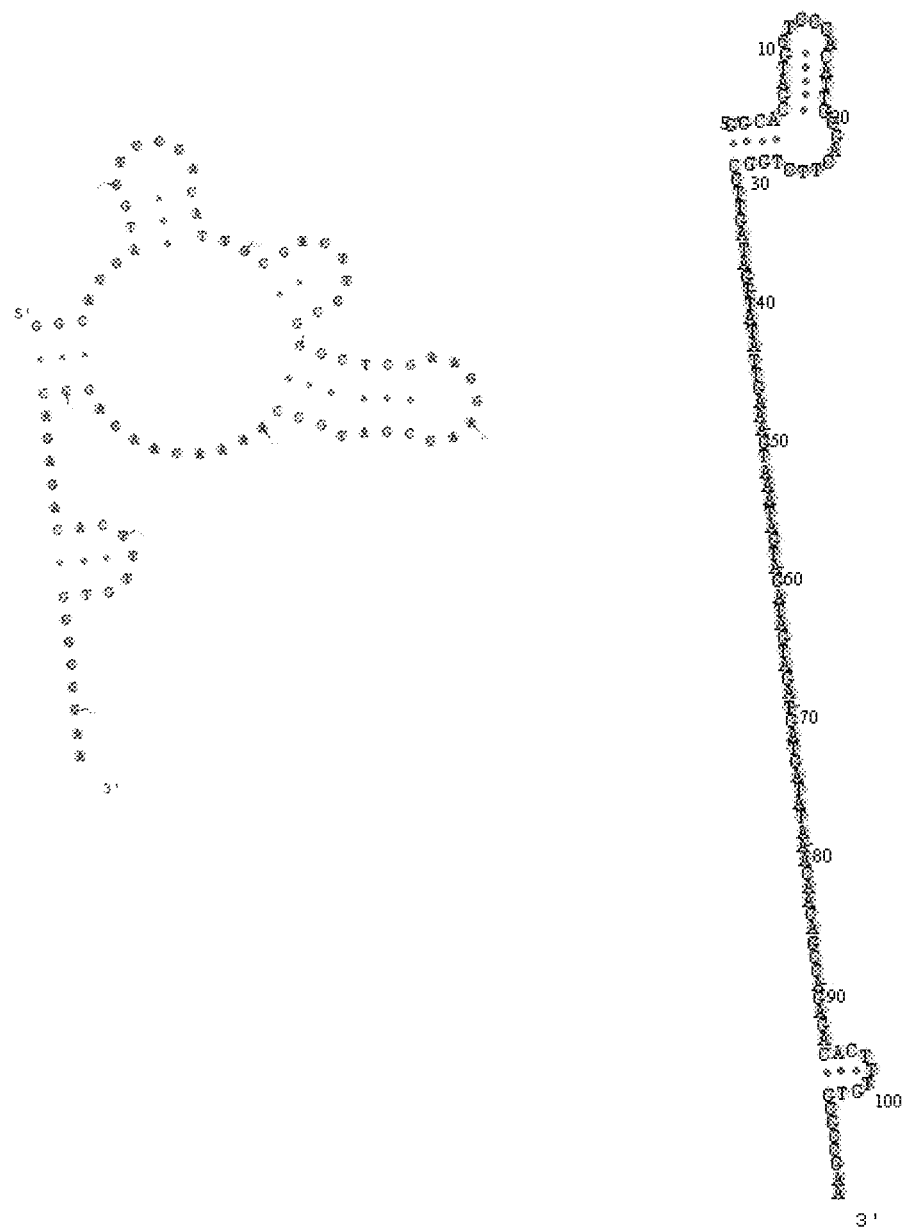

In the case of synthetic targets, such as those used for controls, including internal amplified controls, the sequence can be specifically designed or altered from a naturally occurring sequence to reduce or eliminate hairpin formation in the probe-targeted region(s) above a given temperature. FIG. 15 shows a portion of a randomly generated sequence and its subsequently modified sequence with reduced secondary structure. Some of the nucleotides in the original sequence found in the hybrid portions of the hairpins were modified (typically to A or T) or were deleted from the sequence. Visual OMP software was again used to predict hairpin formation and nucleotides in those hairpins were substituted or deleted. This process was repeated until hairpin Tm in the probe targeted region was not higher than the Tm of the probe/target hybrid. Additional changes were subsequently made to achieve the preferred embodiment that a predicted hairpin involving the probe-targeted nucleotides have a Tm is no higher than 5 degrees below the predicted Tm of the hybrid.

In some embodiments, the low-Tm-probe-targeted regions and adjacent regions of synthetic targets consist of 80%, 90%, or 100% of 2 non-complementary nucleotides (e.g. A and G) in order to limit or prevent hairpins with Tm above a particular Tm. In preferred embodiments, at least 20, or at least 30, or at least 40 or at least 50 nucleotides on either side of the probe-targeted nucleotides consist exclusively of 2 non-complementary nucleotides and the probe-targeted nucleotides consist of at least 80% of those same nucleotides.

Probe-targeted regions described above can be targets of a single probe, or of a pair of probes such as a signaling probe and a quenching probe. Efficient hybridization of one of a pair of probes can limit hairpin formation in the region. Therefore, in some embodiments targets are selected or designed such that the predicted Tm of hairpins is no higher than the highest Tm of the two probe/target hybrids, preferably no higher than 5 degrees below the highest Tm of the two probe/target hybrids.

In some embodiments, interaction between the fluors and quenchers of juxtapositioned, hybridized probe pairs can stabilize both probes to the target nucleotides and increase the Tm of each, particularly the one with the lower predicted Tm. In such cases, the predicted Tm of any hairpin involving targeted nucleotides should be no higher than the empirical Tm of at least one probe/target hybrid, preferably the Tm of both probe/target hybrids, and most preferably at least degrees below the empirical Tm of both probe/target hybrids.

The following patents and publications describe reagents and methods that find use with various embodiments described herein: U.S. Pat. Nos. 8,367,325; 7,972,786; 7,915,014; 7,632,642; 7,517,977; 7,465,562; 7,198,897; U.S. Pub. No. 2013/0210656; U.S. Pub. No. 2013/0203626; U.S. Pub. No. 2013/0095479; U.S. Pub. No. 2012/0282611; U.S. Pub. No. 2012/0208191; U.S. Pub. No. 2012/0202203; U.S. Pub. No. 2012/0198576; U.S. Pub. No. 2012/0088275; U.S. Pub. No. 2012/0040352; U.S. Pub. No. 2011/0311971; U.S. Pub. No. 2009/0226973; U.S. Pub. No. 2009/0111170; U.S. Pub. No. 2009/0081648; U.S. Pub. No. 2008/0280292; U.S. Pub. No. 2008/0193934; U.S. Pub. No. 2006/0275773; U.S. Pub. No. 2006/0177842; U.S. Pub. No. 2006/0177841; and U.S. Pub. No. 2004/0053254; herein incorporated by reference in their entireties.

Embodiments described herein as utilizing a single type or color of fluorophore may make use of the fluorophores exemplified herein, or may make use of additional fluorophores known to those in the relevant fields. As used herein, "fluorophore," "fluorescent dye," "fluorescent label," "fluorescer," etc. are used synonymously. Suitable fluorophores than may find use in embodiments of the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue, Texas Red, and others described in the 6th Edition of the Molecular Probes Handbook by Richard P. Haugland, hereby expressly incorporated by reference in its entirety for all purposes and in particular for its teachings regarding labels of use in accordance with the present invention. Commercially available fluorescent dyes for use with certain embodiments of the invention include, but are not limited to: Cy3, Cy5, (Amersham Biosciences, Piscataway, N.J., USA), fluorescein, tetramethylrhodamine-, TEXAS RED, CASCADE BLUE, BODIPY FL-14, BODIPY R, BODIPY TR-14, RHODAMINE GREEN, OREGON GREEN 488, BODIPY 630/650, BODIPY 650/665-, ALEXA FLUOR 488, ALEXA FLUOR. 532, ALEXA FLUOR 568, ALEXA FLUOR 594, ALEXA FLUOR 546 (Molecular Probes, Inc. Eugene, Oreg., USA), Quasar 570, Quasar 670, Cal Red 610 (BioSearch Technologies, Novato, Ca), ALEXA FLUOR 350, ALEXA FLUOR 532, ALEXA FLUOR 546, ALEXA FLUOR 568, ALEXA FLUOR 594, ALEXA FLUOR 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, CASCADE BLUE, CASCADE YELLOW, Dansyl, lissamine rhodamine B, MARINA BLUE, OREGON GREEN 488, OREGON GREEN 514, PACIFIC BLUE, RHODAMINE 6G, RHODAMINE GREEN, RHODAMINE RED, tetramethylrhodamine, TEXAS RED (available from Molecular Probes, Inc., Eugene, Oreg., USA), and Cy2, Cy3.5, Cy5.5, and Cy7 (Amersham Biosciences, Piscataway, N.J. USA, and others).

Although many embodiments described herein are useful for single-color and/or single-tube assays, it is within the scope of the present invention to combine such assays, or embodiments thereof, with additional fluorophores (e.g., for the detection of other targets) or additional assays performed in other reaction vessels (e.g., mass spec detection of M. tuberculosis).

In some embodiments, reagents and methods are provided for nucleic acid analysis by a multi-color, single-tube assay (a Design I or Design II assay).

Figure 24:
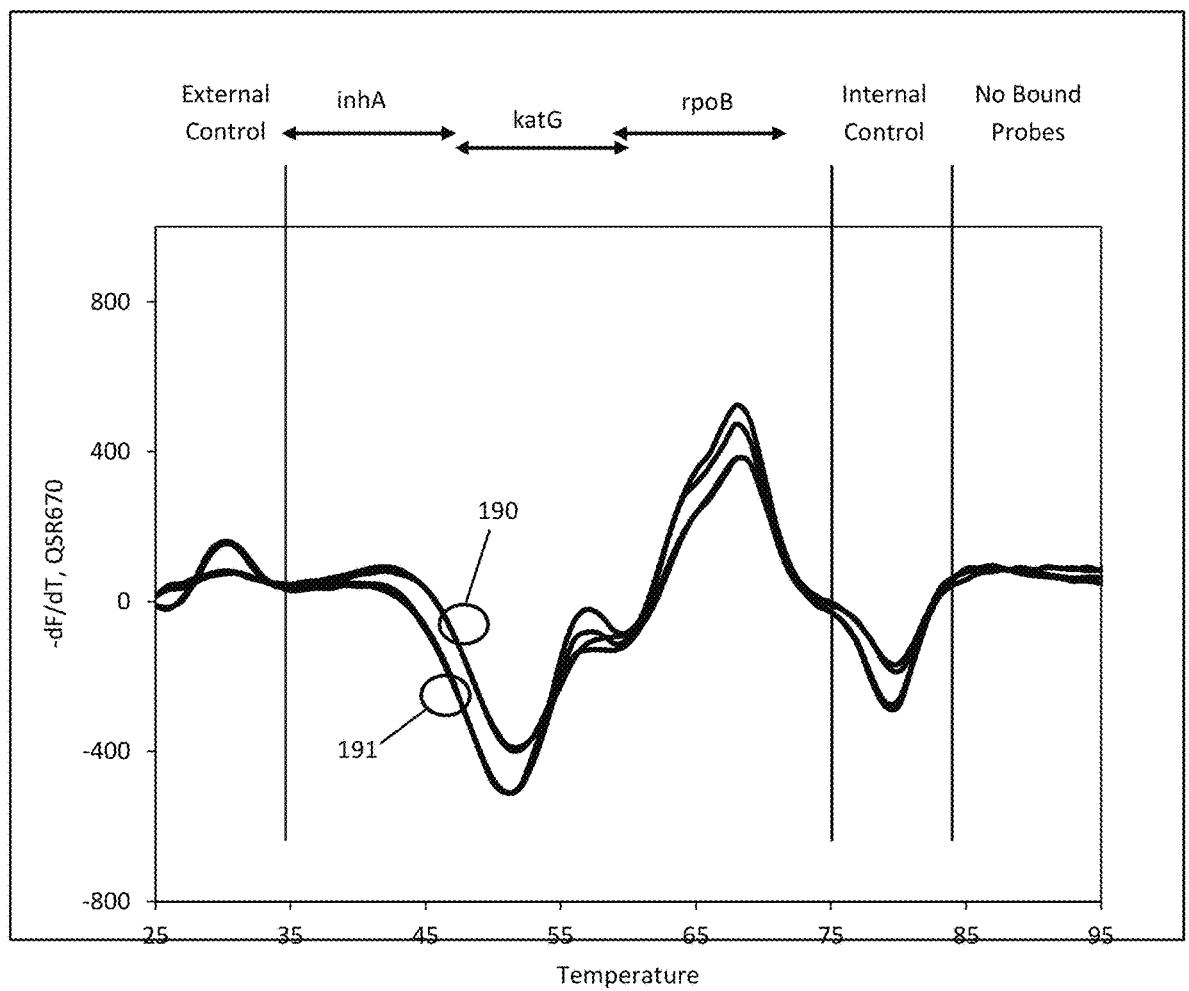
Figure 25:
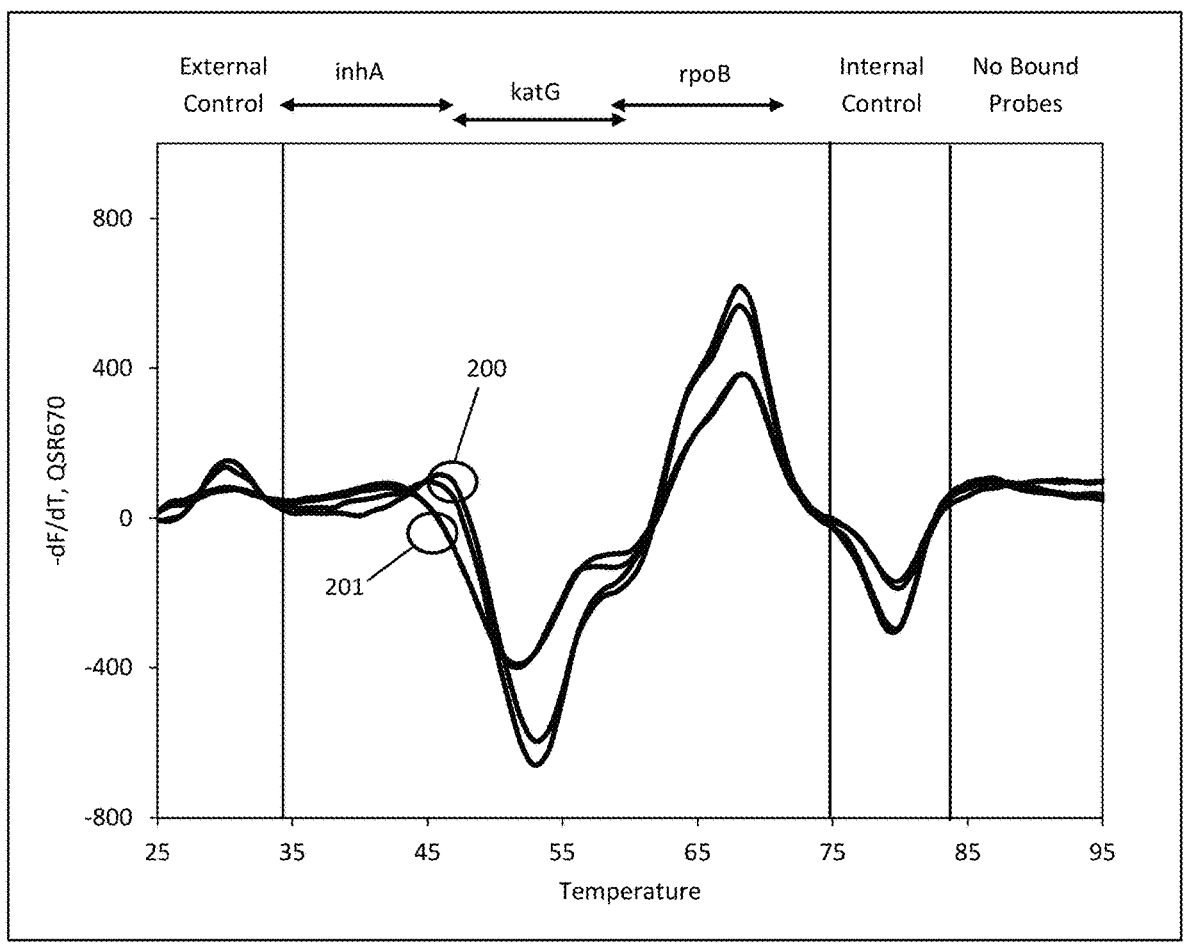

An exemplary multicolor, single tube assay (Design I assay) for the analysis of the pncA gene is depicted, for example, in FIGS. 1-2 and 19-20. Such an assay is referred to herein as a Design I assay. The pncA gene target is 561 base pair in length which was divided for the distribution of the probes into two sections of approximately equal length of the gene sequence. Correct identification of *Mycobacterium bovis* from *Mycobacterium tuberculosis* sequences which differ by a single base pair was the first step in the probe design in order to give each species its own fluorescent signature. This paired On/Off probe set design contained a high Tm On probe (75° C.) that was complementary to the *M. bovis* sequence and a single mismatch to the *M. tuberculosis* sequence. The Off probe was complementary to both sequences. This design insured that *M. bovis* would generate a fluorescence signal at a higher temperature and both sequences would be turned off by the binding of the Off probe at the same temperature. Thus creating a distinct signature that would clearly identify *M. bovis* from *M. tuberculosis* (FIG. 24). With this pair of probes designed to distinguish *M. bovis*, the subsequent pairs of probes were designed in relationship with the actual location within the gene itself. The basic formulation for paired probe design was a length of 25 base pairs for the On probe and 17 base pairs for the Off probe. Subsequent modifications were made to the probes based on: (1) potential secondary structure formation that would reduce the capabilities of the probes to bind to the target, and (2) inter-molecular cross hybridization of the same probe binding to itself. These types of interactions were predicted using Visual OMP software version 7.5.1.0 (DNA Software Inc., Ann Arbor, Mich. USA) and the probes were modified by changing the sequence of the probe to reduce or eliminate these interactions. Substituting a cytosine (C) nucleotide for a thymine (T) will cause a minimal disruption of the base pairing between the probe and its complementary target; therefore, this substitution was the first choice when confronted with potential secondary structure formation or inter-molecular cross hybridization. FIG. 25 shows the final design of the two-color scheme (Design I). The first two pairs of On/Off probes show Off probe Tm higher than the paired On probe's. While in most On/Off pairings the Off probe turns the On probe off in a temperature dependent manner, not all pairing was designed this way. For example, in the Quasar 670 region there is a pair of On probes adjacent to each other (Tm=58.7, Tm=61.1) in which the quencher from the upstream On probe is used to turn off the fluorescent of the other On probe.

Another exemplary multicolor, single tube assay, in this instance also for the analysis of the pncA gene is referred to herein as a Design II assay. In such a design, the probes are not contiguously arranged along the target sequence according to temperature and/or color. Rather, in some embodiments, particular sequences are selected along the target sequence on the basis of their length (number of nucleotides), Tm's for the probes to those particular sequences are determined, and then colors are assigned to adjacent probe-pair in anticipation of converting them to On/Off probe-pairs in an specific order within a color that maximizes the Tm-spacings between the probes of each color. The result of such a design is that adjacent probe-pairs (On/Off pairs) may not be related to each other in either color (e.g., different label) nor temperature (e.g., not arranged sequentially according to Tm magnitude). Probe Design II uses the wide temperature space that is afforded when both the probe and target are single stranded DNA, particularly at the end of a LATE-PCR reaction, an LEL-PCR, or an asymmetric PCR reaction. Instead of being constrained by where a probe would align with its complementary hybridization sequence, the arrangement of On/Off probe-pairs is based on their respective Tm's. Thus the On/Off pairs are first designed and assigned Tm values according to their sequences. Then the probe pairs are assigned colors based on their Tm values, rather than on their location along the length of the target sequence, finally the sequences of probes within a color adjusted to maximize their temperature spacing across the entire temperature range available for probe target hybridization. The result is that the probe pairs become contiguous over temperature but are not necessarily contiguous along the target sequence.

Figure 26:
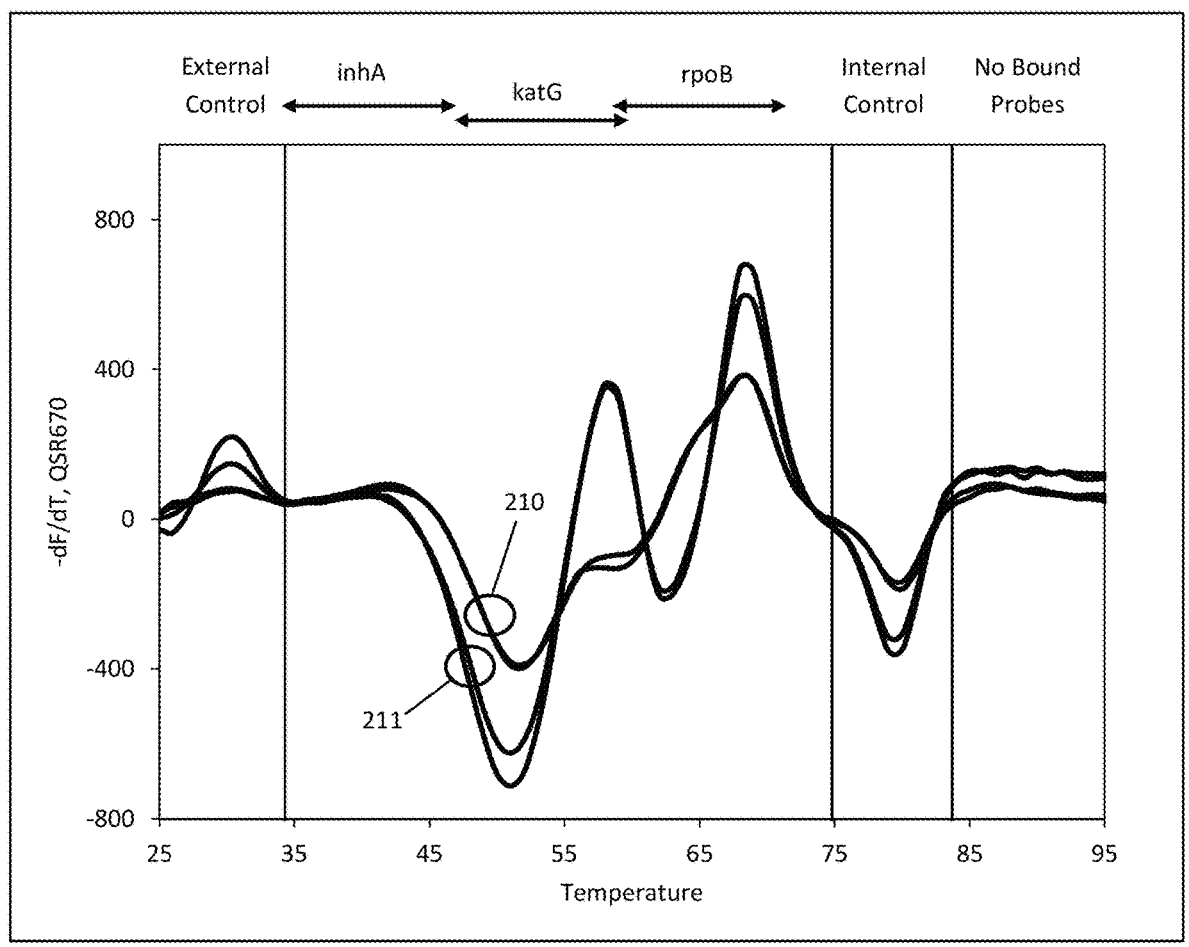
Figure 27:
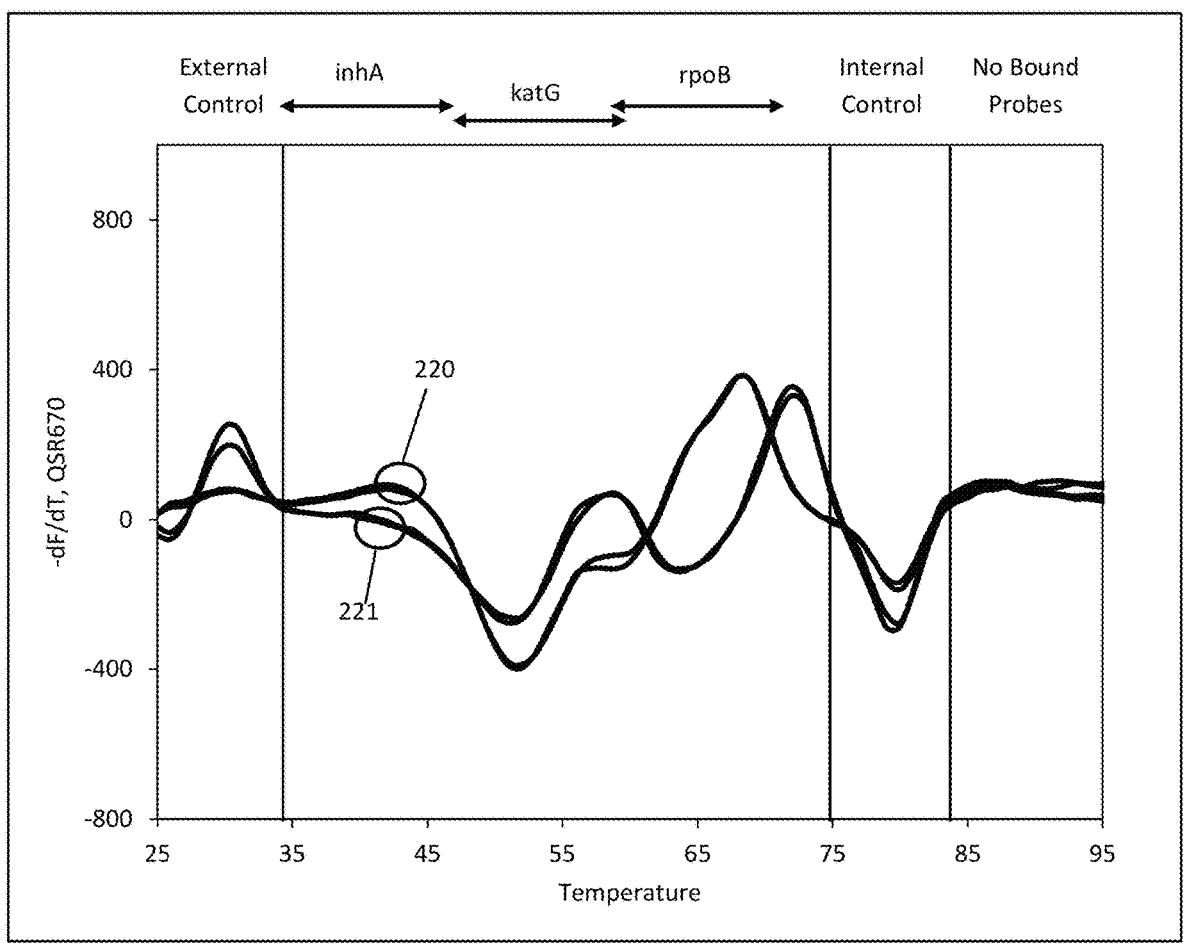
Figure 28:
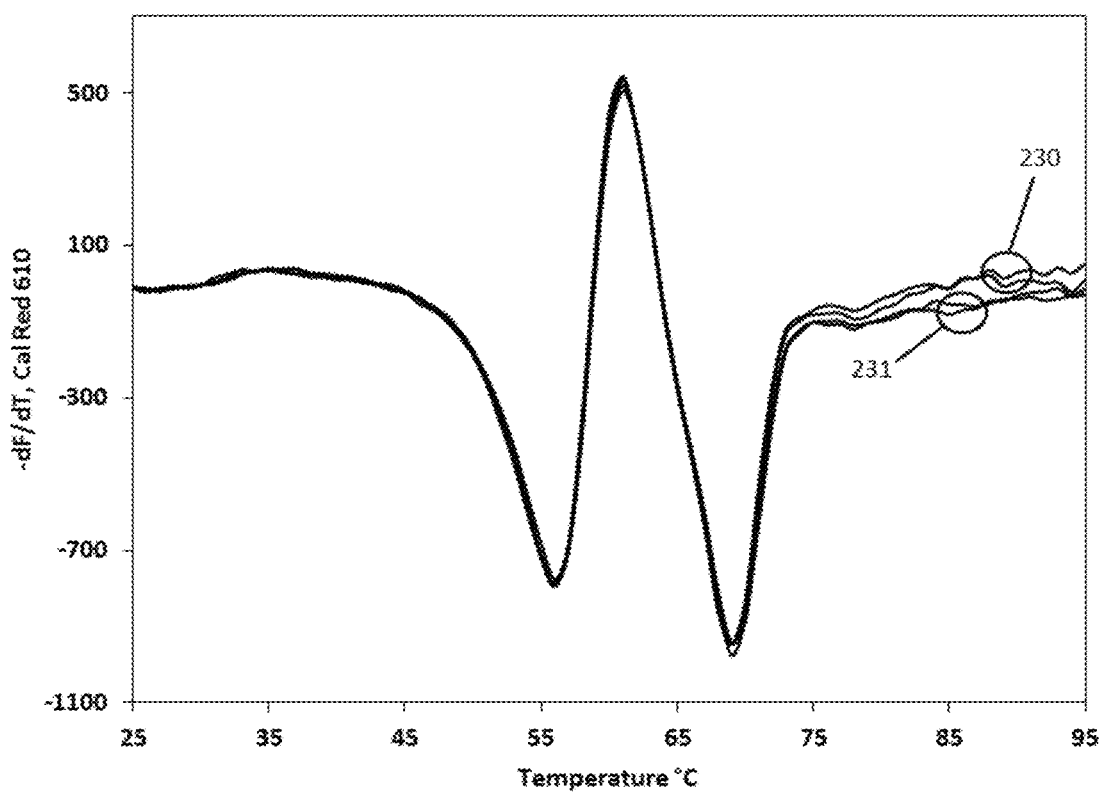
FIG. 28 shows exemplary temperature-dependent fluorescence data from a single tube, two-color, pncA assay, with panel (A) showing Cal Red 610 and panel (B) showing Quasar 670.
Figure 28:
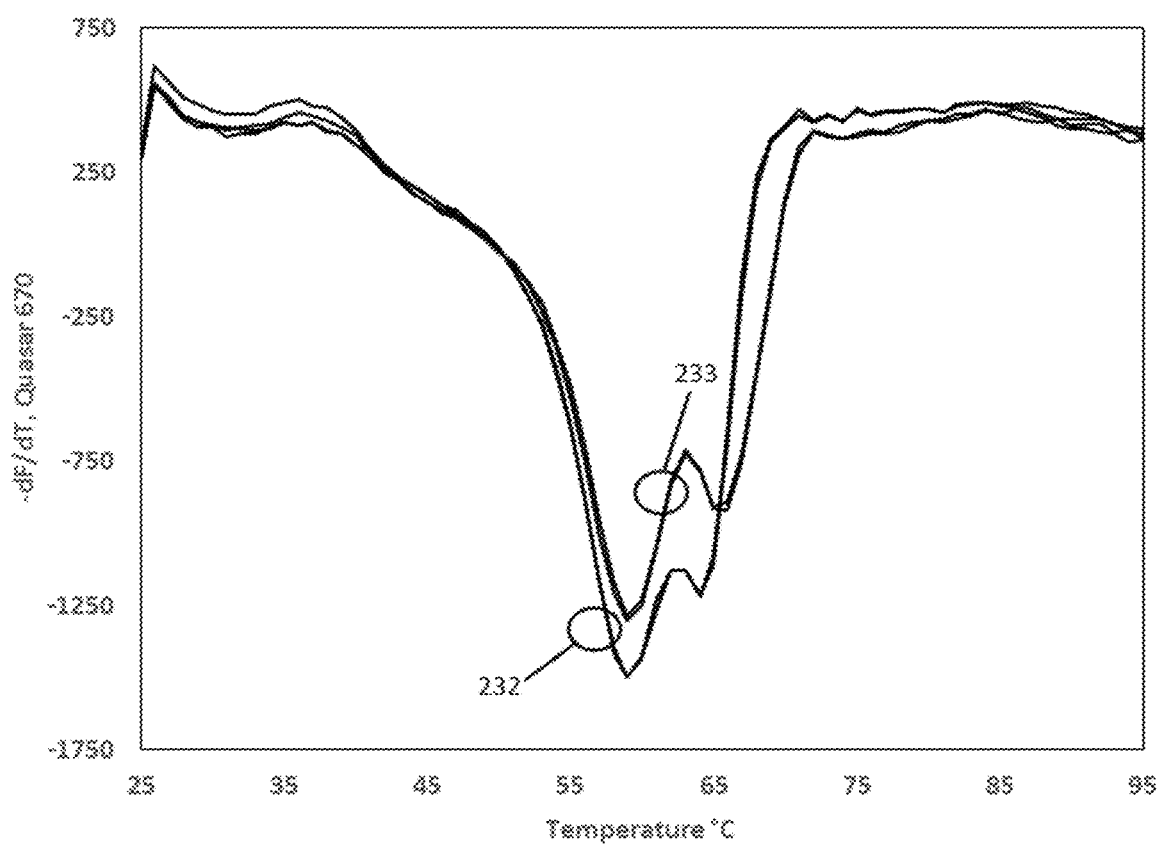

The Design II process begins by the selection of length of On (signaling) and Off (quenching) probes. In the exemplary pncA Design II assay, 20 base pairs hybridization sequences for On probes and adjacent 15 base pair hybridization sequences for Off probes were aligned across the target sequence. An optional second step includes nucleotide substitutions, as describe above for Design I, to correct for any potential secondary structure formation or inter-molecular cross hybridization. The probe Tm's produced following these modifications are shown in FIG. 26. In a third step each signaling probe within a probe-pair is assigned a color based on its Tm rather than position, in order to maximize the temperature space regardless of location along the target sequence. FIG. 27 shows the results of this rearrangement based on temperature. Additional refinement of the Tm differences among the probes is made to maximize the use of the temperature space. One method to adjust the Tm of a probe to its hybridization sequence is introducing a C to G change in the probe which results in a G to T mismatch between the probe and the target, thus reducing the overall Tm of the probe. Any introduction of a mismatch will lower the Tm of the probe/target hybridization to its perfect complement. In order to increase the overall differences in some of the probes to the complementary target (*M. tuberculosis*, H37Rv strain) mismatches were introduced to the probe sequences. The resulting refinement is shown in FIG. 28. Each of the probe-pairs for the exemplary pncA gene (PZA resistance) assay are described in Table 2.

TABLE 2

Exemplary Design II, pncA probes

| Sequence 5' to 3' | SEQ ID NO: | Tm's | 5' Modification | 3' Modification | Nucelotide Position |
|---|---|---|---|---|---|
| AACGCCGCGCTGGAGGAGATGCTT | 65 | 74.5 | QSR670 | BHQ2 | 196_215 |
| GGCCGATACCACCGT | 66 | 60.6 | | BHQ2 | 216_230 |
| ACCATCGGAGCGTACAGCGGCTGT | 67 | 68.7 | QSR670 | BHQ2 | 406_425 |
| CTACAAGGGTGCCTA | 68 | 53.8 | | BHQ2 | 426_440 |
| ACAGTTGGTTTGCAGCTCCTGAGT | 69 | 64.7 | QSR670 | BHQ2 | 161_180 |
| GCACTGCCGGCGTCG | 70 | 55.2 | | BHQ2 | 181_195 |
| AAGACCCGGGTGATCACTTCTCTT | 71 | 63.4 | QSR670 | BHQ2 | 546_565 |
| AAGGACTTCCACATC | 72 | 51.3 | | BHQ2 | 566_580 |
| AACGCTATCAGTGACTACCTGGTT | 73 | 58.1 | QSR670 | BHQ2 | 616_635 |
| CGCTGCGTTGGCTCG | 74 | 51.1 | | BHQ2 | 636_650 |
| AATCGGCAATTGAGTCGGTGTTTT | 75 | 54.5 | QSR670 | BHQ2 | 441_460 |
| CAGTCTGGACGCG | 76 | 47.3 | | | 461_475 |
| TAGCGGTACGCAATGGCTTGGCCTA | 77 | 73.4 | CO560 | BHQ1 | 266_285 |
| AGACGGCCGAGGAC | 78 | 60.1 | | BHQ1 | 286_300 |
| ACACCATCACGTCGTGGCAACCGT | 79 | 68.6 | CO560 | BHQ1 | 581_600 |
| CCGGAGCGGCGGGCT | 80 | 56.8 | | BHQ1 | 601_615 |
| ACCTCTCGGCGTGGACTTCTATCCGT | 81 | 60.3 | CO560 | BHQ1 | 476_495 |
| ATTGCGTTAGCGGTA | 82 | 48.3 | | BHQ1 | 496_510 |
| TTTCGTTGACGTGCAGAATGACAA | 83 | 57.4 | CO560 | BHQ1 | 685_705 |
| TGCGGGTGTTGGTCA | 84 | 46.7 | | BHQ1 | 706_720 |

TABLE 2-continued

Exemplary Design II, pncA probes

| Sequence 5' to 3' | SEQ ID NO: | Tm's | 5' Modification | 3' Modification | Nucelotide Position |
|---|---|---|---|---|---|
| AAAGAATGGTACGTCACTGCTGTT | 85 | 53.2 | CO560 | BHQ1 | 371_390 |
| TCGGAGGAGTTGACG | 86 | 42 | | BHQ1 | 391_405 |
| ACTTCCTCGTCGTGGCCATCGCGT | 87 | 69 | CR610 | BHQ2 | 511_530 |
| CGGCACACTGGACTA | 88 | 53.4 | | BHQ2 | 531_345 |
| AGCGCGGCGTCGATGAGGTTGACT | 89 | 68.6 | CR610 | BHQ2 | 336_355 |
| AATTGGCTGCGGTAA | 90 | 52.5 | | BHQ2 | 356_370 |
| AATCGCTGGCGGTAACTGGTGGTT | 91 | 67.8 | CR610 | BHQ2 | 651_670 |
| TTCTGCGAGGGTGGC | 92 | 60.4 | | BHQ2 | 671_685 |
| AACATCGATCATTGTGTGCGCCTT | 93 | 64.4 | CR610 | BHQ2 | 301_320 |
| TGTGGTCGGTATTGC | 94 | 54.2 | | BHQ2 | 321_335 |
| AAGACTTGACAGCGGGTGTGTCTT | 95 | 62.9 | CR610 | BHQ2 | 231_250 |
| ACTAGGGTGCTGGTG | 96 | 52.1 | | BHQ2 | 251_265 |
| TTCCGAACGTATGGTGGATGTAAA | 97 | 55.1 | CR610 | BHQ2 | 721_740 |
| TGCTTGGGCAGTTGC | 98 | 45 | | BHQ2 | 741_755 |

Underlined nucleotides are not complementary to the hybridization sequence. The 5' modifications are QSR670 is quasar 670, CO560 is cal orange 560 and CR610 is cal red 610. While the 3' modifications BHQ1 and BHQ2 are black hole quenchers.

The Design I and Design II methods of designing probe sets for analyzing a target seqeuence are not limited to the pncA examples described above. In particular, the Design II method is advantageous for at least the following reasons: (a) it can be applied to any long target sequence; (b) assignment of On probe and Off probe lengths is rapid because they do not have to be adjusted to achieve specific Tm's; (c) ordering of probe-pairs by Tm over the desired temperature space is rapid; (d) assignment of colors is rapid; and (e) adjustment of Tm's by introducing specific types of mis-matches is made in the context of whole sets of probes and is rapidly accomplished.

In some embodiments, the Design II method is used to design probe sets for a single-color, two-color, three-color, four-color, or further multi-color assays. In some embodiments, the Design II method is used to design probe sets for single-target or multi-target assays.

The assays described herein typically include three or more probe-pairs (e.g., each probe-pair comprising an On (signaling) and Off (quenching) probe). When designed using the Design II method the arrangement of the colors and/or Tm's of the hybridization sequences for the probe-pairs is unrelated to their linear order along the target. For a single color assay, the Design II method may result in no ascending or descending linear order to the Tm's of the hybridization sequences along the target sequence. Further, because particular probe target sequences are initially arranged along the target sequence, irrespective of the identity of the target sequence, the resulting particular sequences and probes have Tm's that are not arranged in any particular order (e.g., ascending or descending), but are instead dictated by their particular base composition along the target sequence.

EXPERIMENTAL

Example 1

Design of a Synthetic Internal Control Target with Reduced Secondary Structure, Amplification with LATE-PCR Primers, and Detection Using Signaling and Quenching Probes A random sequence of 60% G and C nucleotides and 40% A and T nucleotides was generated.

(SEQ ID NO: 58)
5'CTTCACGTAATACAAGAACCAGCGGGGGTTCGGGGCACACTCACCACG

CGGGGCCGGTGTGGCCCTAAGCGCAGTCGAGACTTGTCGGGTAGTGCGCC

TGGTTCTGAGCGGTGTGGAGTGGGTGCGCCCTACGTGGGGGAGGCTTCAC

GAGCTTCCGAGTTGCATCTGTGAGTGCGAGCTTAACGAGCGAGCTGCTCC

AGTATGTGGCATGGACACGGTCCGCGCCCTCAGAATGCGACGGCAAAATG

CTCGCGAGCTGCGGTCCGCCGTACCGATGGTACCAGATAAGAGACCTGTT

AGGCAACCTGTTCAACGGGGCATGCTCTCAAGTGGATAGACTCCACCAGT

GCTGGAGGACTCGGCATGTCTCGGAGGTCGAGGCATGGCACGATGCTCCC

CTATTGCGACTTCCGGGCTCGAAGGAACCGATGCCAAAAGCAACAGCCAG

AGACACTTTGTGCGCCGACTGCCTAGGTCTGGTCAGCAATTCCCAATACA

GC-3'

LATE-PCR primers were selected that would amplify an 82 nucleotide segment of the control target (FIG. 15, left). To insure that probes with very low $T_m$ (20 to 40° C. range) would hybridize efficiently, the portion of the target between the primer and primer complement sequences was modified to prevent some predicted hairpin formation. Some nucleotides, mainly C nucleotides, in the predicted hairpin stems were deleted or altered. Additional G and A nucleotides, as well as some T nucleotides were added to that region to enable possible hybridization of a second probe and to further separate the probe—targeted segments from primer regions (FIG. 15, right). High $T_m$ hairpins were similarly eliminated from other portions of the target for possible future primer and probe design. The sequence of the modified internal control target was (SEQ ID NO: 59)
5'CTTCACGTAATACAAGAAGCAGCGGGTTCGGGAGTGTCACAGTGGGTT

GCCGTGTGTAAGAGTCGAGACTTGTCGGGTAGTCCTGGTTGTGTGGTCGA

ACGCATTAGCTTGGGTCAACGAGCTTCCGAGTTGCATCTGTGAGTTTAAC

GAGAGCCAGTATGTAGCGTCAGAATGCAGAATCAGCAGGCACGTGTCCGC

CGTAGATGGTACCAGATAAGAGACCTGTTAGGCAACCTGTTCAAAATACT

ACTCTGGAGGACTGAGATGGCACGATGCTCCCACATTGCGACTTCTGCCC

TTGATAGTTATATTGAAAGTAAATAGTAGATAGTAGATGATGATATAAAC

-continued

AACAGCCAGAGACACTTTGTGCGCCGACTGCCTATCAAATTCCCAATACA

GC-3'

A synthetic DNA with the 400 base pair modified sequence was synthesized, inserted into the pIDTSMART-KAN plasmid, cloned and purified by Integrated DNA Technologies (Coralville, Iowa, USA). An estimated 100 or 1,000 copies of the plasmid were added to a reaction mixture containing final concentrations of 50 nM limiting primer (SEQ ID NO: 9), 1,000 nM excess primer (SEQ ID NO: 10), 100 nM signaling probe (SEQ ID NO: 52), 300 nM quenching probe (SEQ ID NO: 53), 0.3 mM dNTPs, 3 mM magnesium, 1× Platinum Taq PCR Buffer and 1.5 units Platinum Taq DNA polymerase (Life Technologies) in a final volume of 25 microliters. A Stratagene Mx3005P thermal cycler was used to carry out a program of 95° C. for 3 minutes, then 50 cycles of 95° C. for 10 seconds and 75° C. for 40 seconds, followed by 10 minutes at 25° C. and a melt from 25° to 95° C. in 1° C. steps every 30 seconds with detection for Quasar 670 fluorescence at each step.

Figure 16:
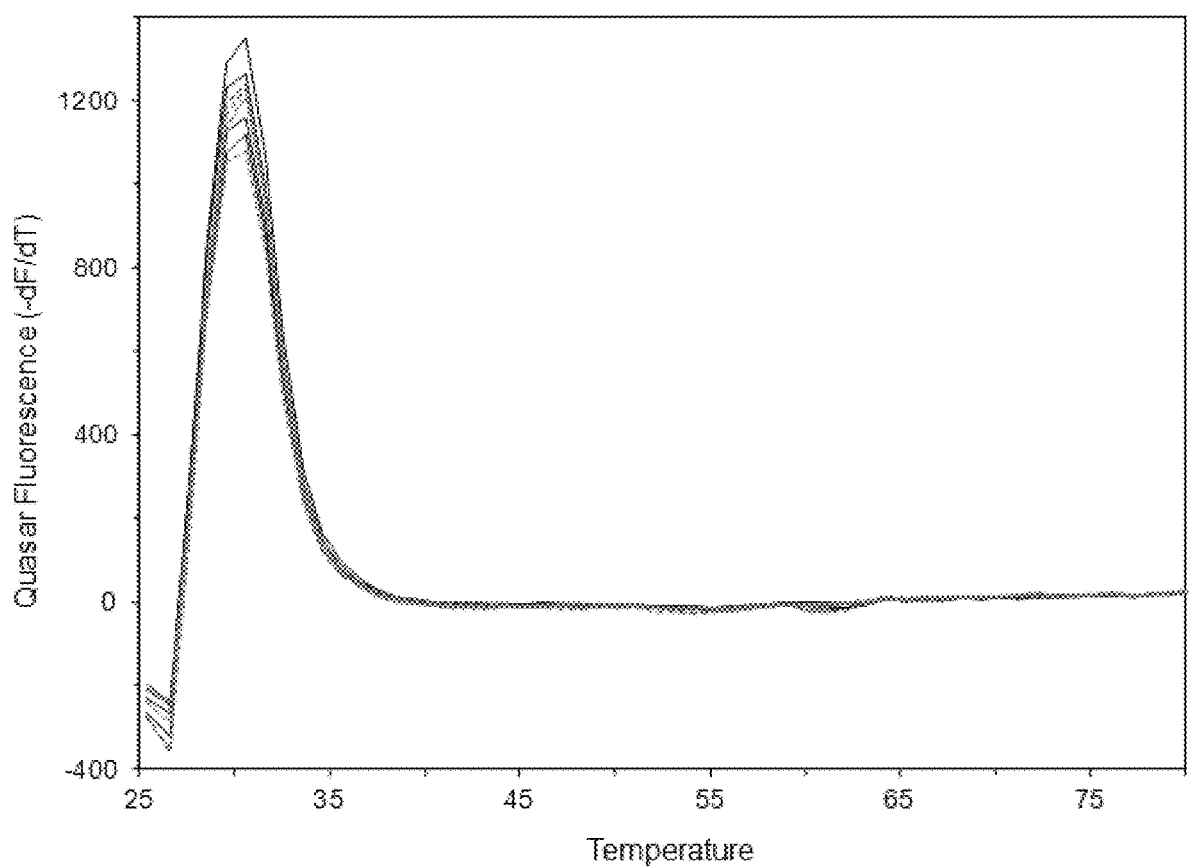

FIG. 16 shows the negative derivative of the fluorescence values. The valley at 27° C. indicates the approximate $T_m$ of the quencher probe as it melts from the amplified target and allows the hybridized signaling probe to emit higher levels of fluorescence. The peak at 30° C. indicates the $T_m$ of the signaling probe with the amplified target. Solid lines represent replicate samples with an estimated initial 1,000 targets and dashed lines represent replicate samples with an estimated 100 targets. The overlapping plots indicate that the amplified target has reached saturation levels with the signaling probe (target is in excess in all cases); a desirable result for control signal consistency.

Example 2

Multiplex Detection of Drug Resistance in Three Different Genes for Strains of *M. Tuberculosis*

A tetraplex LATE PCR assay was used to detect drug resistance in the three genes inhA promotor (promoter region), katG, and rpoB, plus an amplifiable $1^{st}$ internal control and a non-amplifiable $2^{nd}$ internal control. The location of each target (See Table 1) was based on the Genbank sequence NC_000962.3.

TABLE 1

Target Sequnces

| | Sequence 5' to 3' | |
|---|---|---|
| rpoB Sequence | ACGTGGAGGCGATCACACCGCAGACGTTGATCAACATCCGGCCGGTGGTCGCCGCGAT CAAGGAGTTCTTCGGCACCAGCCAGCTGAGCCAATTCATGGACCAGAACAACCCGCTGT CGGGGTTGACCCACAAGCGCCGACTGTCGGCGCTGGGGCCCGGCGGTCTGTCACGTGA GCGTGCCGGGCTGGAG | SEQ ID NO: 61 |
| katG Sequence | GCTTGGGCTGGAAGAGCTCGTATGGCACCGGAACCGGTAAGGACGCGATCACCAGCGG CATCGAGGTCGTATGGACGAACACCCCGACGAAATGGGACAACAGTTTCCTCGAGATCC TGTACGGCTACGAGTGGGAGCT | SEQ ID NO: 62 |
| inhA promotor Sequence | TCGCAGCCACGTTACGCTCGTGGACATACCGATTTCGGCCCGGCCGCGGCGAGACGATA GGTTGTCGGGGTGACTGCCACAGCCACTGAAGGGGCCAAACCCCCATTCGTATCCCGTT CAGTCCTGGTTACCGGAGGAA | SEQ ID NO: 63 |
| Internal Control Sequence | GGCACGATGCTCCCACATTGCGACTTCTGCCCTTGATAGTTATATTGAAAGTAAATAGTA GATAGTAGATGATGATATAAACAACAGCCAGAGACACTTTGTGCGCCGAA | SEQ ID NO: 64 |

The rpoB target sequence is 191 base pair in length and located at nucleotides 761011 to 761201. The six probes used for this target cover 101 base pairs within the target between the nucleotides 761078 to 761178. This covers the 81 base pair region known as the RRDR responsible for rifampin resistance in *M. tuberculosis*. The katG target sequence is 139 base pair in length and located at nucleotides 2155084 to 2155222. The two probes used for this target cover 31 base pairs within the target between the nucleotides 2155160 to 2155190 which include codons 309 to 317, in particular codon 315. The inhA promotor target sequence is 139 base pair in length and located at nucleotides 1673371 to 1673509. The two probes used for this target cover 31 base pairs within the target between the nucleotides 1673419 to 1673449. The probes covers 21 nucleotides of the promoter region in particular the mutation sites −15 and −8 and the first three codons of inhA promotor gene.

Results are shown in FIGS. 6-11.

For the inhA promotor promoter region all strains were drug sensitive while strains 16 and 22 contained a single nucleotide change (C/T) at the minus 15 position, and strain 21 had a minus 8 position change (T/C) were drug resistance. For the katG gene the strains 1, 5, 11, 14, 21 and 22 were drug sensitive while all other strains (S315T, a serine located at amino acid position 315 changed to a tyrosine) were resistant. For the rpoB gene, the strains 1, 19, and 22 were drug sensitive while all other strains contain a variety of mutations that were resistant.

Reaction Components and Conditions were as Follows:

For the inhA Promotor Gene (Promoter Region)

```
Limiting Primer:
                                        (SEQ ID No. 5)
5' TTCCGGTAACCAGGACTGAACGGGATACGAATGGGGGTTTGG Excess Primer:
                                        (SEQ ID No. 6)
5' TCGCAGCCACGTTACGCTCGTGGACATAC
```

Probes used for inhA Promotor

```
inhA promotor_ON
                                        (SEQ ID No. 19)
5' BHQ2-AAAAAAAAAAAAAAGGCAGTCATCCCGTT-QSR670 inhA promotor_OFF
                                        (SEQ ID No. 20)
5' BHQ2-TTACAGCCTATCGCCTCGC-C3 Spacer
```

For katG Gene

```
Limiting Primer:
                                        (SEQ ID No. 3)
5' AGCGCCCACTCGTAGCCGTACAGGATCTCGAGGAAAC Excess Primer:
                                        (SEQ ID No. 4)
5' TCTTGGGCTGGAAGAGCTCGTATGGCAC
```

For 1st Internal Control

```
Internal control limiting primer
TTCGGCGCACAAAGTGTCTCTGGCTGTTGT (SEQ ID NO: 9)

Internal control excess primer
GGCACGATGCTCCCACATTGCGACTTC    (SEQ ID NO: 10)
```

Probes used for katG Gene

```
katG_ON
                                        (SEQ ID No. 17)
5' QSR670-ACTCGCGTCCTTACCCAAAAAAAAAAAAAA-BHQ2 katG_OFF
                                        (SEQ ID No. 18)
5' ATGTCGGTGGTGA-BHQ2
```

For rpoB Gene

```
Limiting Primer:
                                        (SEQ ID No. 1)
5' CTCCAGCCAGGCACGCTCACGTGACAGACCG
```

```
Excess Primer:
                                        (SEQ ID No. 2)
5' ACGTGGAGGCGATCACACCGCAGACGTT
```

Probes used for rpoB Gene

```
rpoB_Probe1_OFF
                                        (SEQ ID NO: 11)
BHQ2-CTGGTTGGTGCAGAAG-C3 Spacer rpoB_Probe2_ON
                                        (SEQ ID NO: 12)
BHQ2-TCAGGTCCATGAATTGGCTCAGA-QSR670 rpoB_Probe3_OFF
                                        (SEQ ID NO: 13)
BHQ2-CAGCGGGTTGTT-C3 Spacer rpoB_Probe4_ON
                                        (SEQ ID NO: 14)
BHQ2-ATGCGCTTGTGGATCAACCCCGAT-QSR670 rpoB_Probe5_ON
                                        (SEQ ID NO: 15)
QSR670-AAGCCCCAGCGCCGACAGTCGTT-BHQ2 rpoB_Probe6_OFF
                                        (SEQ ID NO: 16)
ACAGACCGCCGG-BHQ2

1st Internal Control ON
                                        (SEQ ID NO: 52)
QSR670-ATTCTATTATTTATTTTCAT-BHQ2

Internal Control OFF
                                        (SEQ ID NO: 53)
ATCATTATTTACTA-BHQ2
```

2nd Internal Control

```
Internal Control Fluor Strand
                                        (SEQ ID NO: 54)
QSR670-CAGCTGCACTGGGAAGGGTGCAGTCTGACC-C3

Internal Control Quencher Strand
                                        (SEQ ID NO: 55)
GGTCAGACTGCACCCTTCCCAGTGCAGCTG-BHQ2
```

Primesafe

```
Primesafe Sense
                                        (SEQ ID NO: 56)
Dabcyl-GGATCAGATTAGCACTGATGTA-Dabcyl Primesafe Antisense
                                        (SEQ ID NO: 57)
Dabcyl-TACATCAGTGCTAATCTGATCC-Dabcyl
```

LATE PCR amplifications were carried out in a 25 µl volume consisting of 1×PCR buffer (Invitrogen, Carlsbad, Calif.), 3 mM MgCl2, 300 nM dNTPs, 50 nM limiting primer and 1000 nM excess primer for each primer set, 2.0 units of Platinum Taq DNA Polymerase (Invitrogen, Carlsbad, Calif.), 100 nM of On Probe and 300 nM of Off Probe for all probes except for the 1st internal control probe set which was 50 nM of On Probe with 150 nM of Off Probe. Each Primesafe II strand was added at 600 nM while the fluor strand for the $2^{nd}$ internal control was 50 nM and the quencher strand was 150 nM. For each strain tested approximately 1000 genomes equivalents were used and amplification reactions were run in triplicate.

The thermal profile for the amplification reaction was as follows: 98° C./3 min for 1 cycle, followed by 98° C./10 s-75° C./40 s for 60 cycles, followed by 10 min at 75° C.

This is followed by a melt starting at 25° C. with 1° C. increments at 30 s intervals to 98° C.

Figure 6:
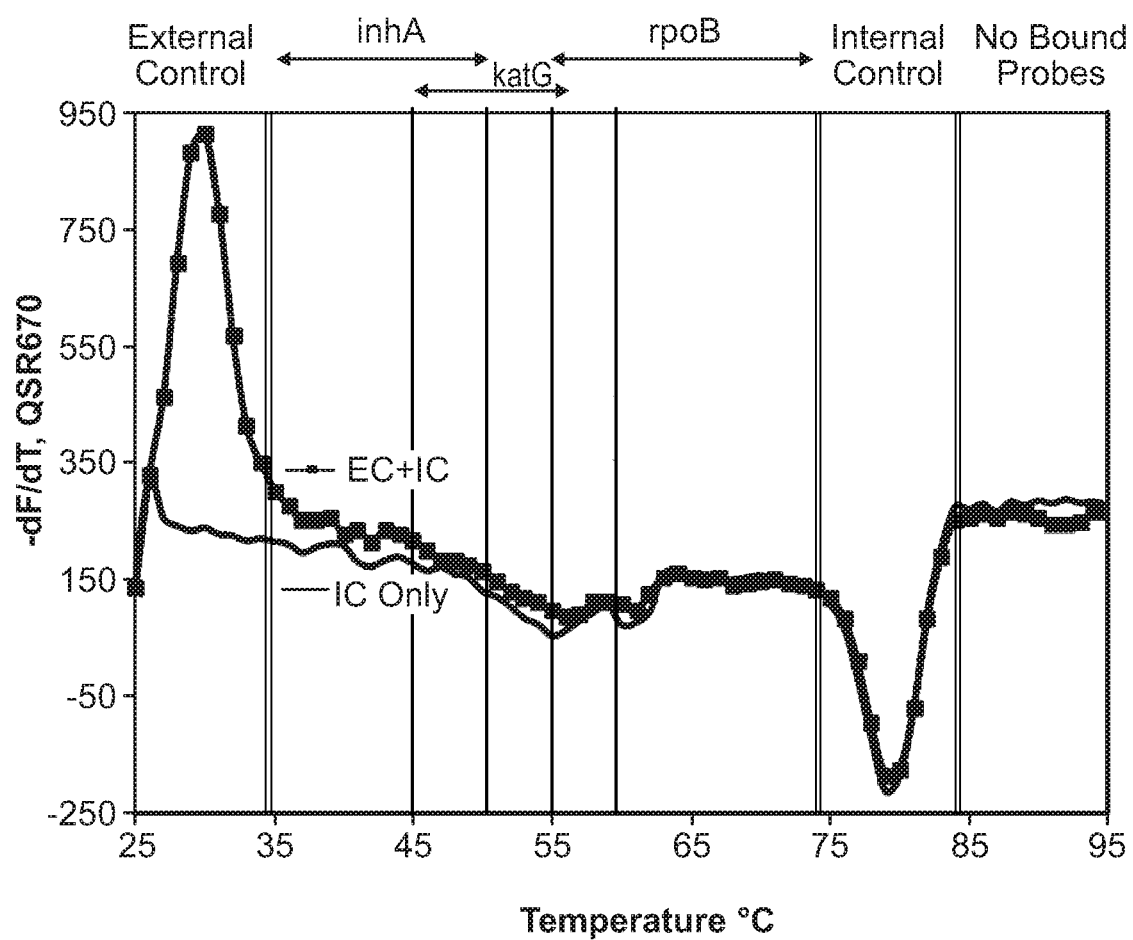
Figure 7:
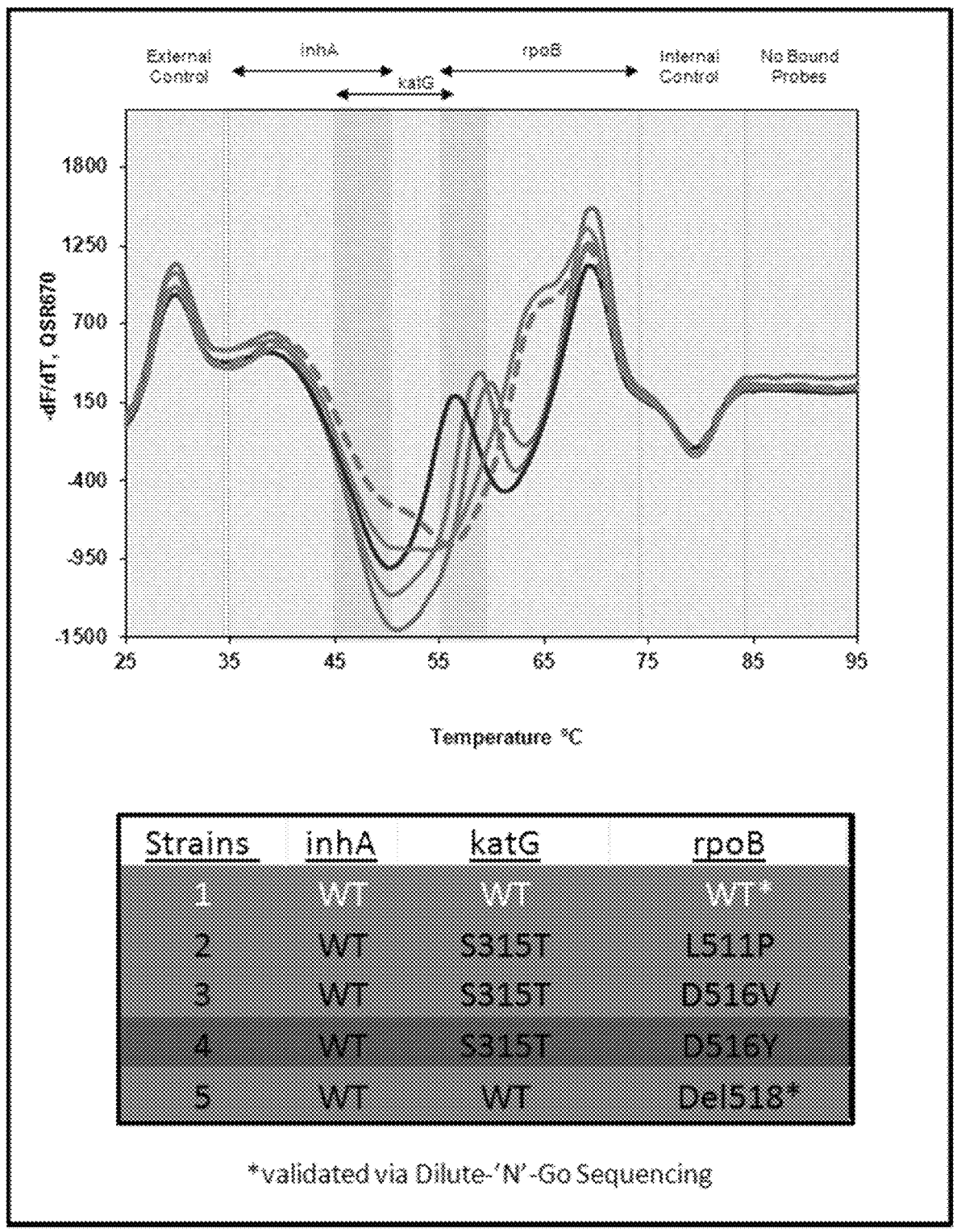
Figure 8:
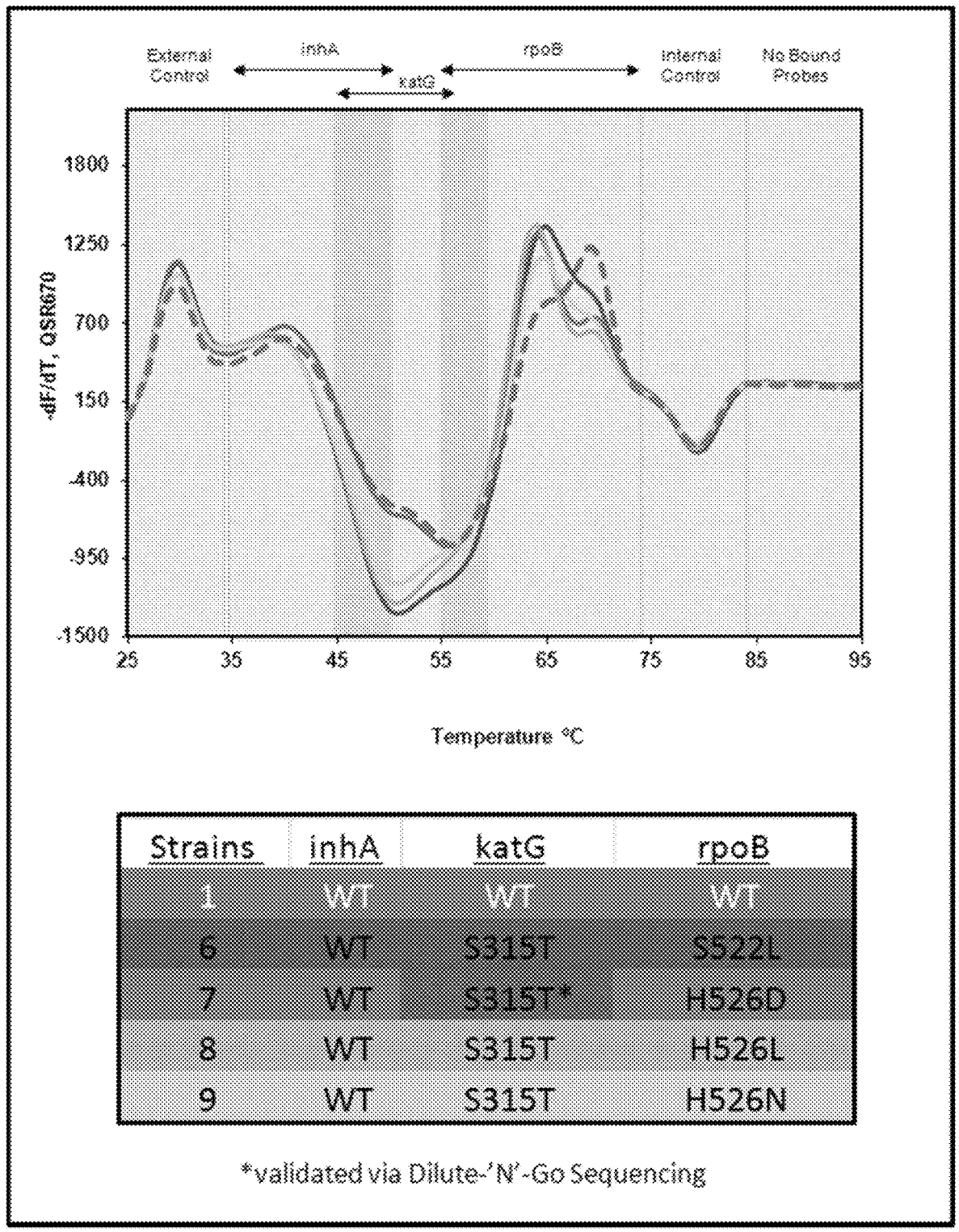
Figure 9:
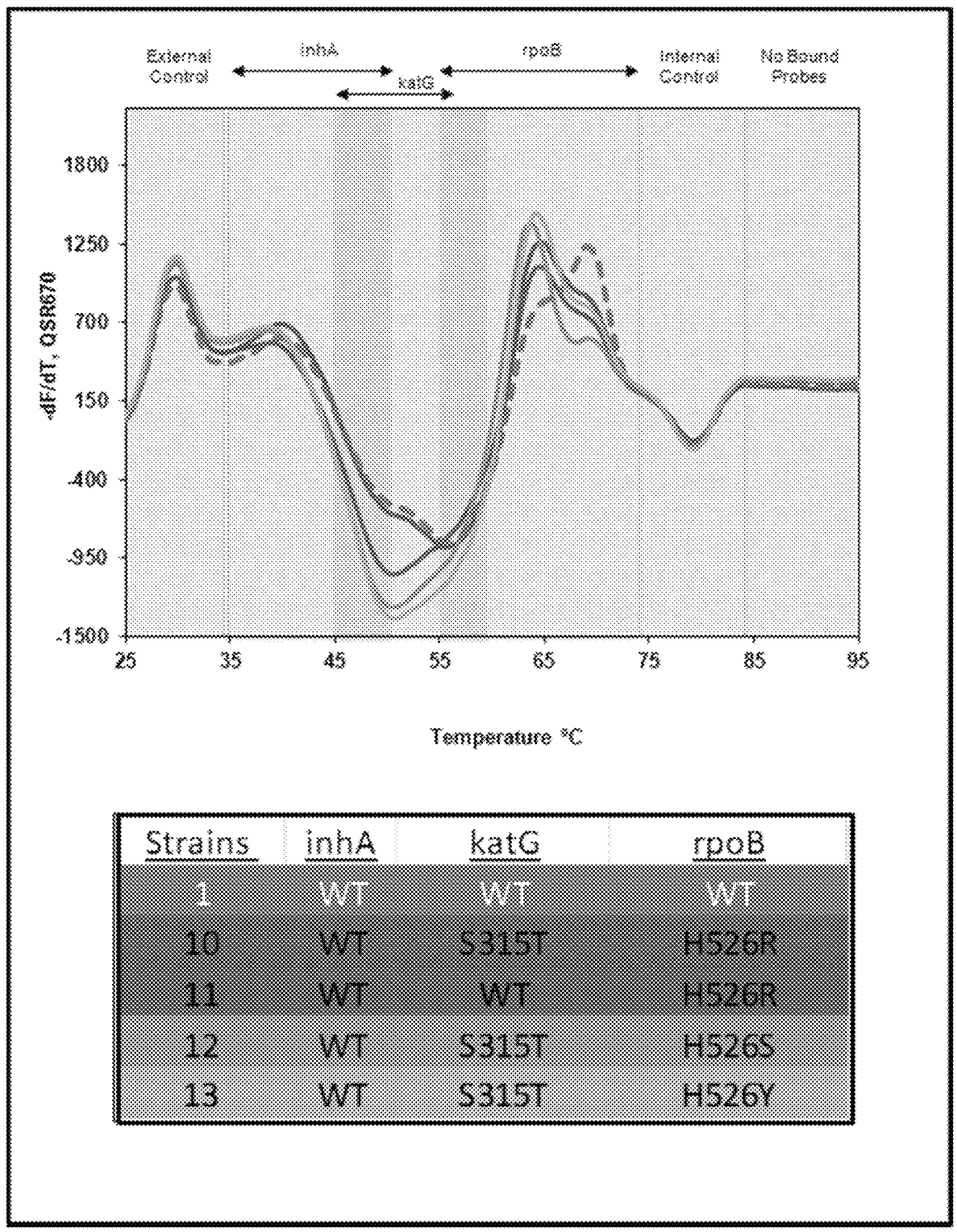
Figure 10:
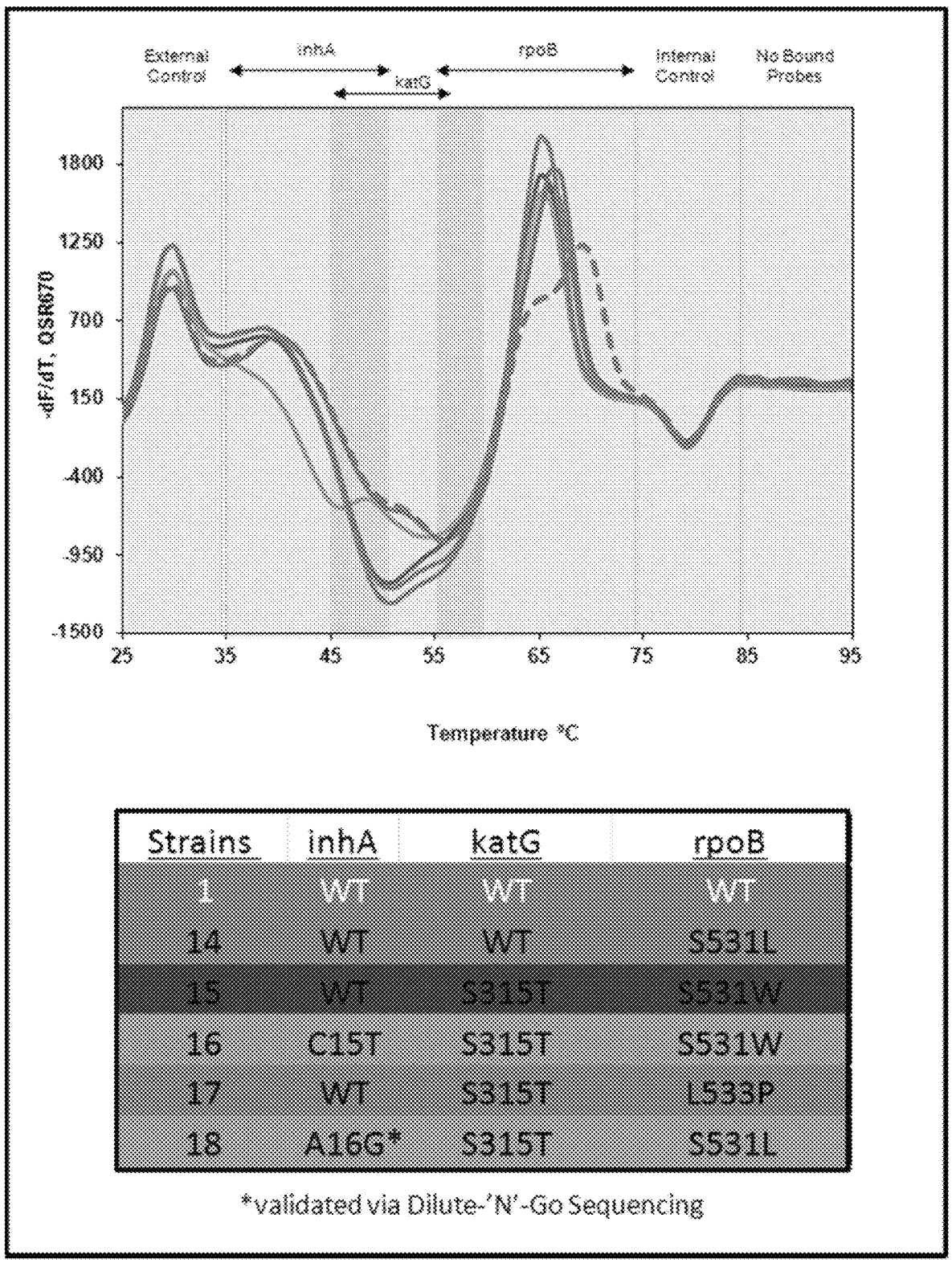
Figure 11:
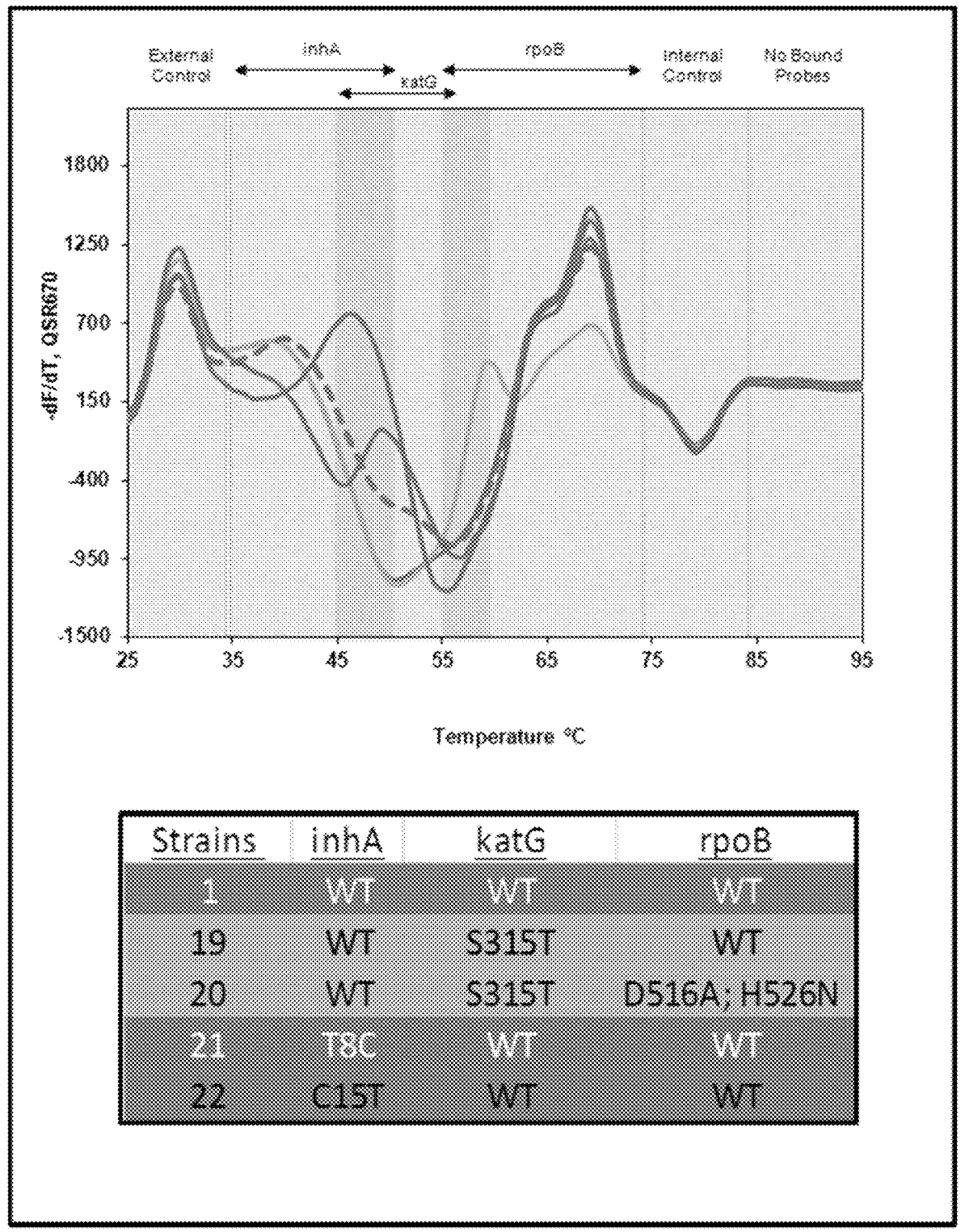
Figure 12:
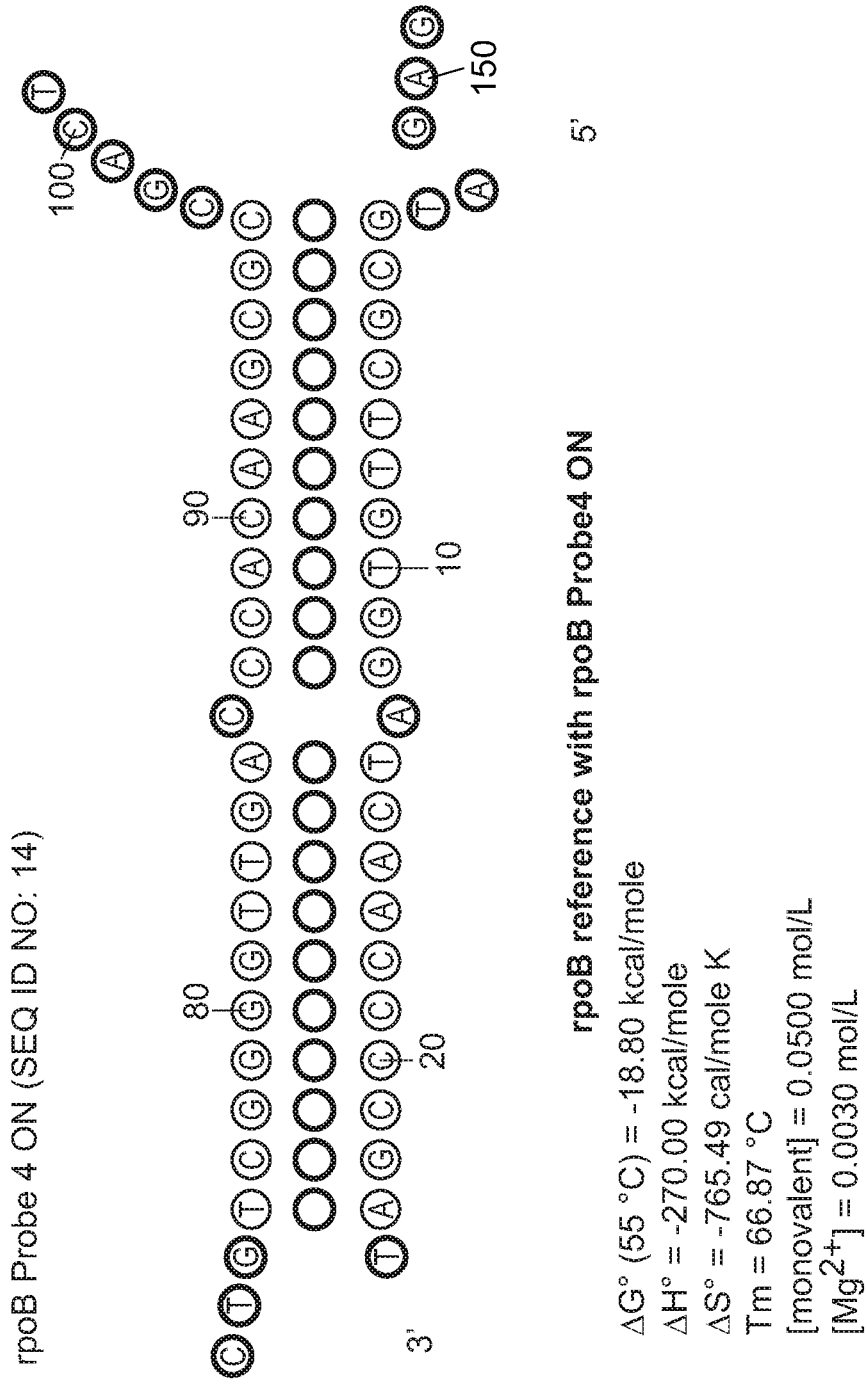
Figure 12:
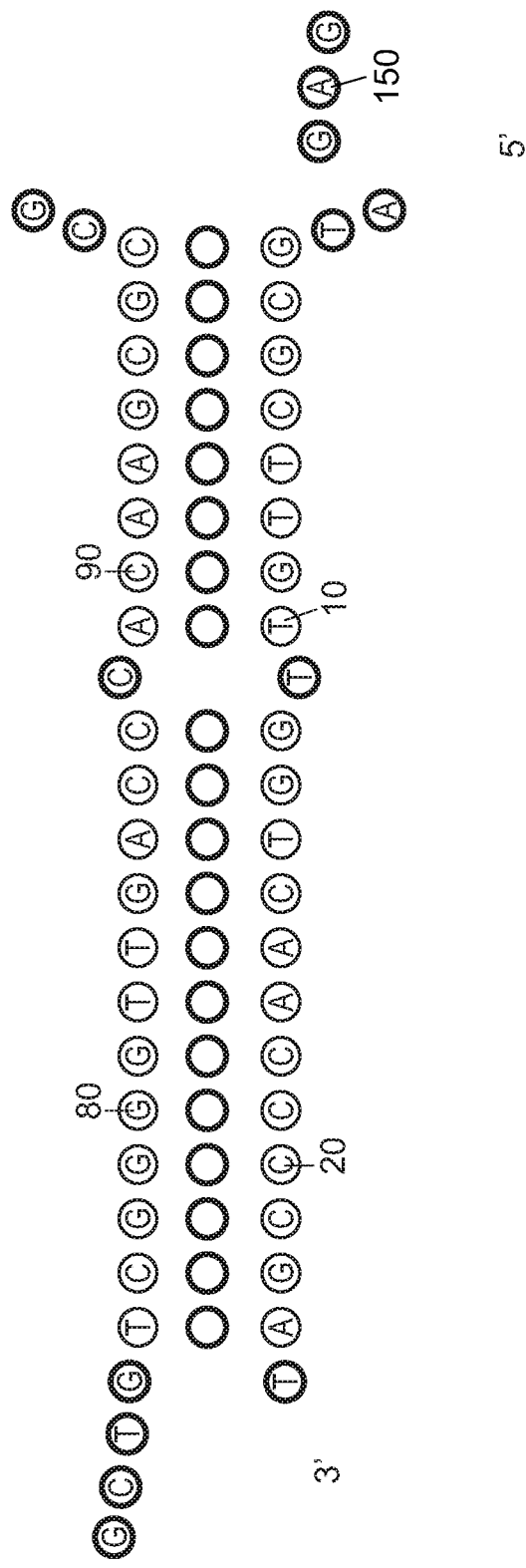
Figure 12:
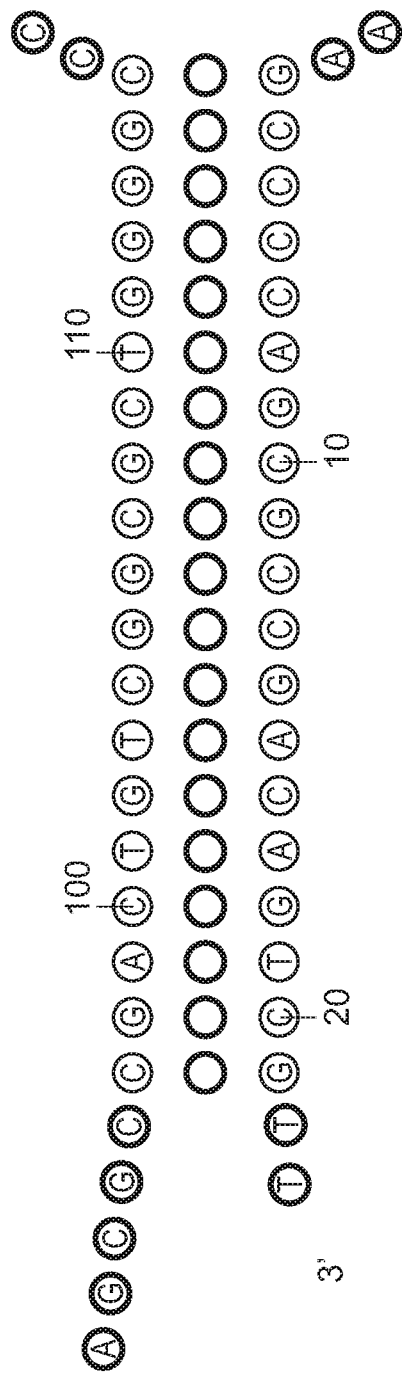
Figure 12:
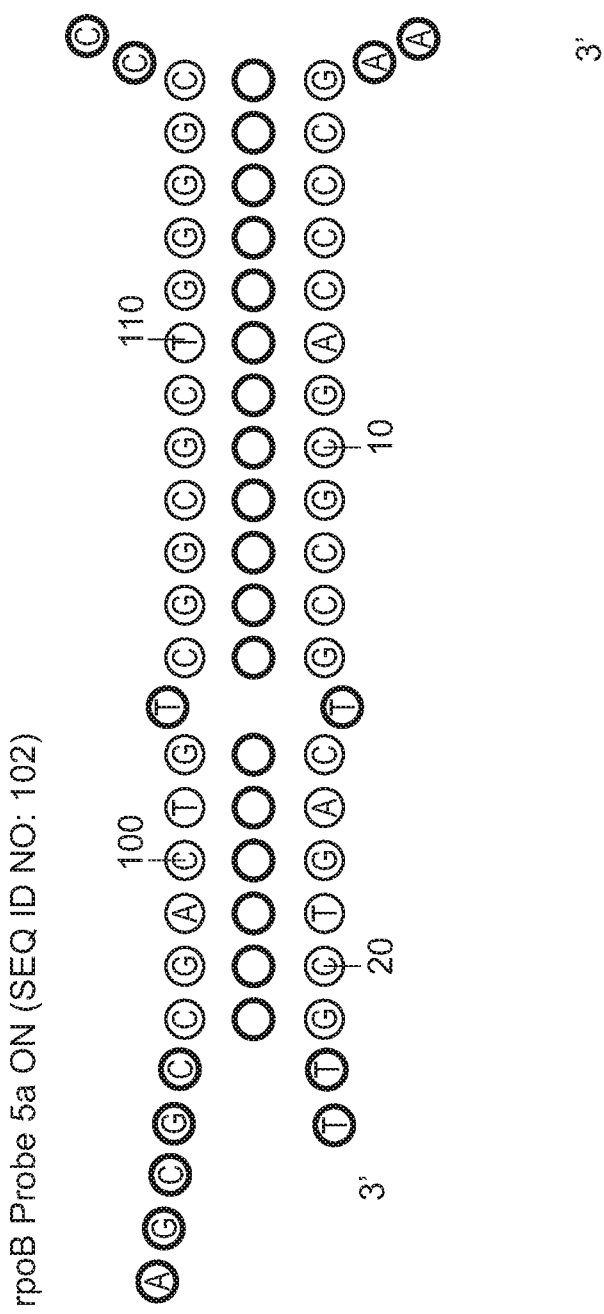
Figure 13:
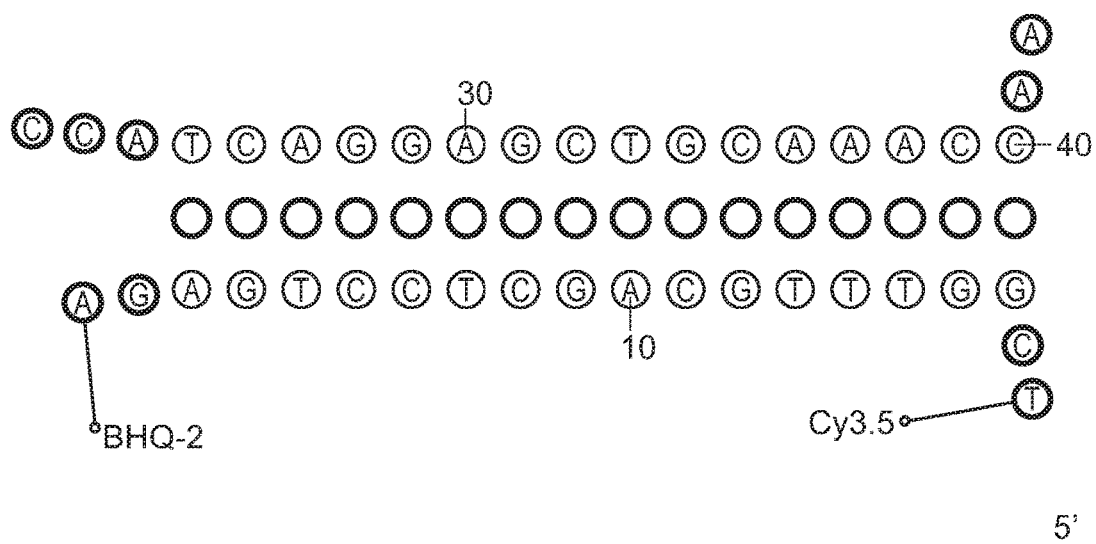
Figure 13:
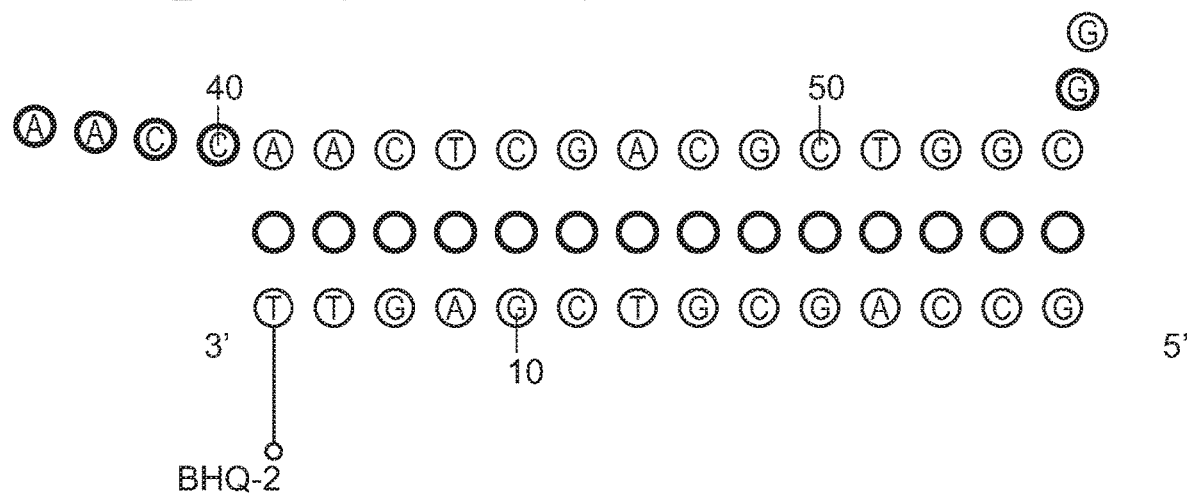
Figure 13:
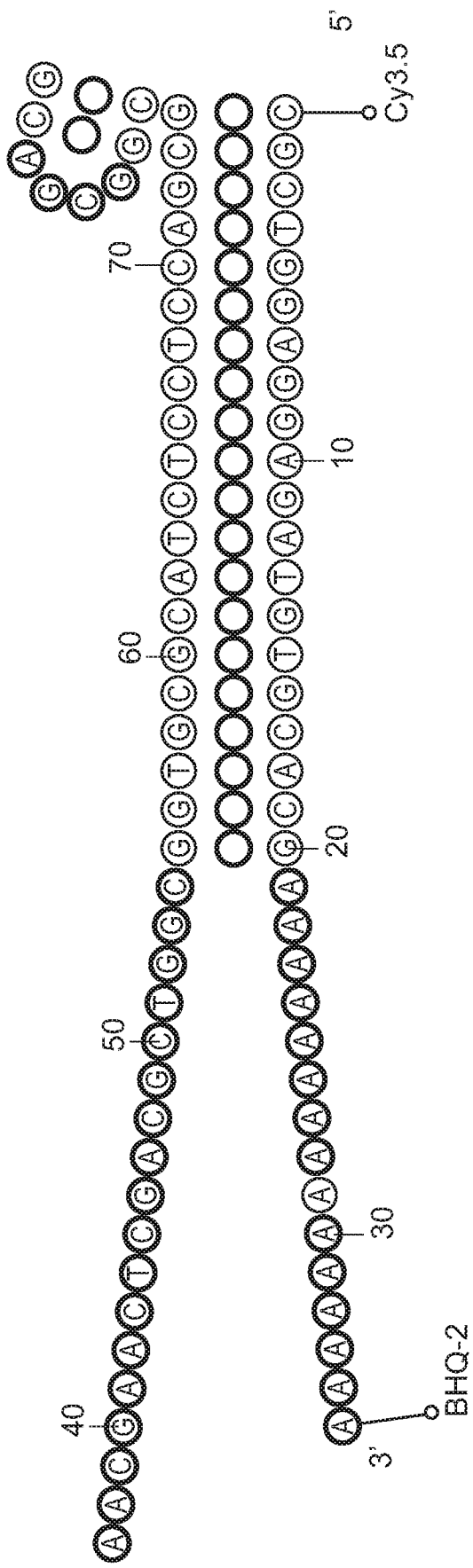
Figure 13:
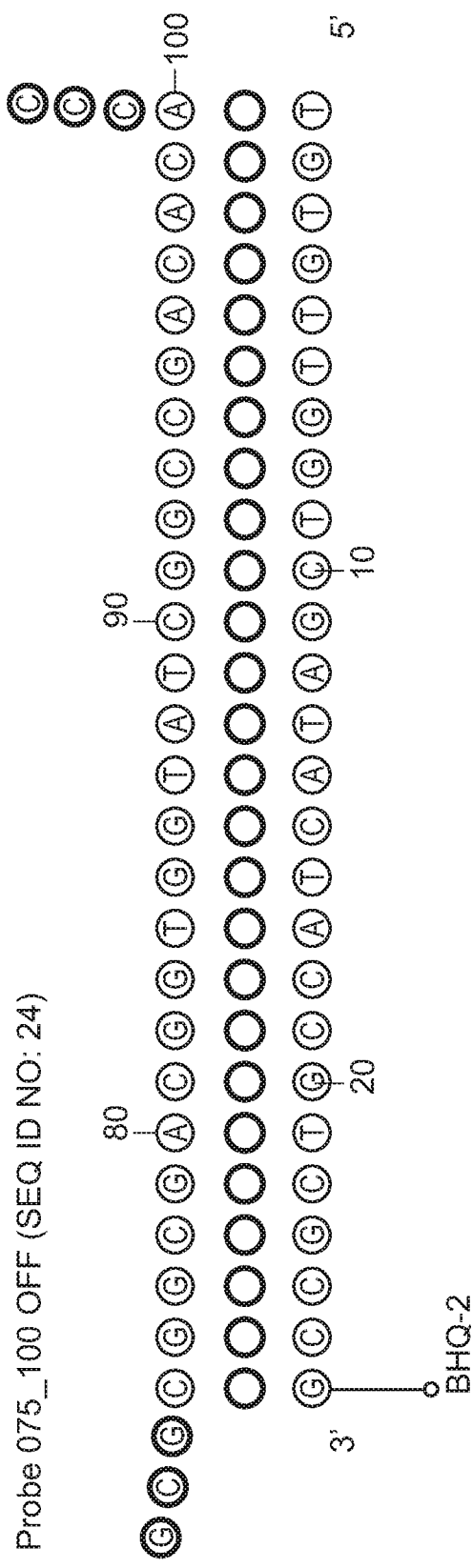
Figure 13:
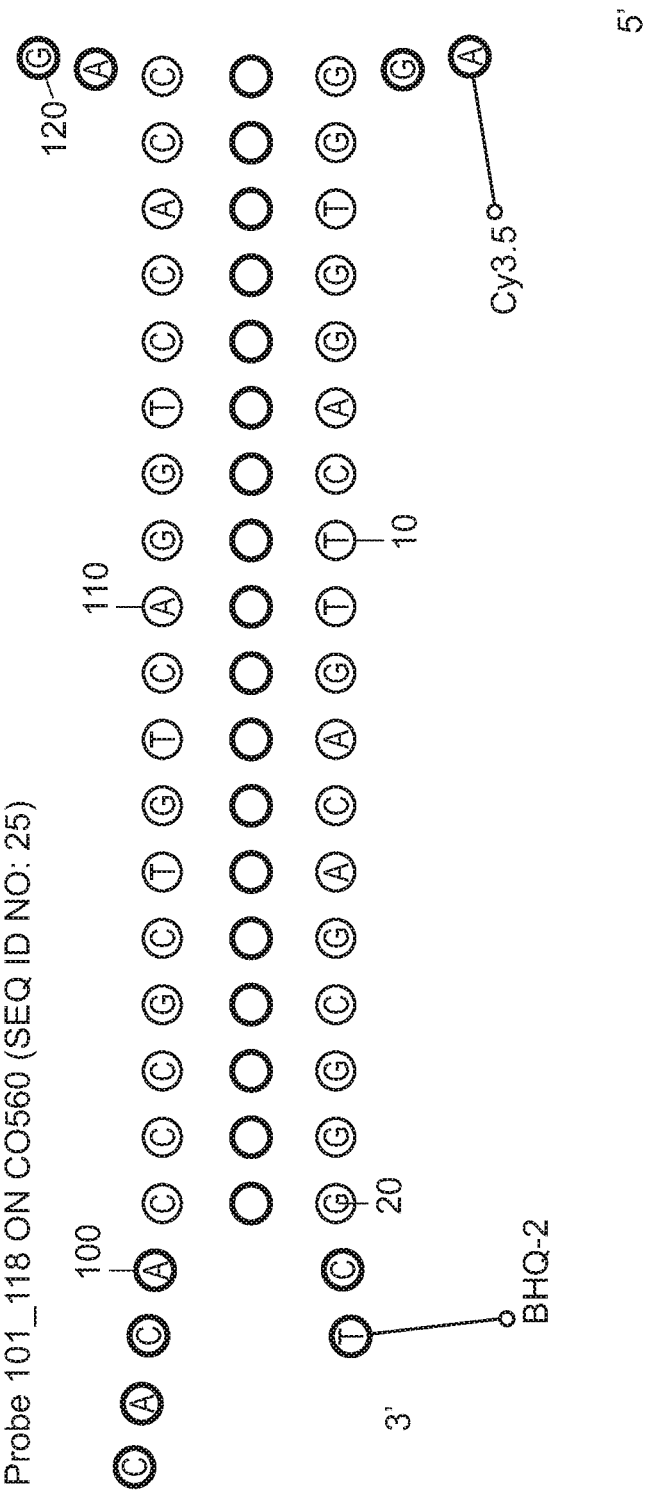
Figure 13:
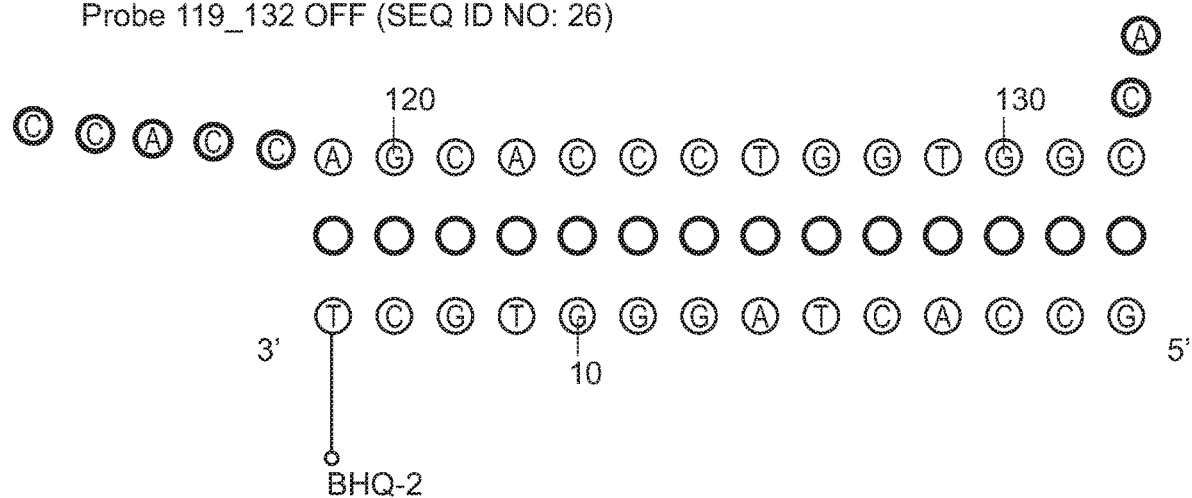
Figure 13:
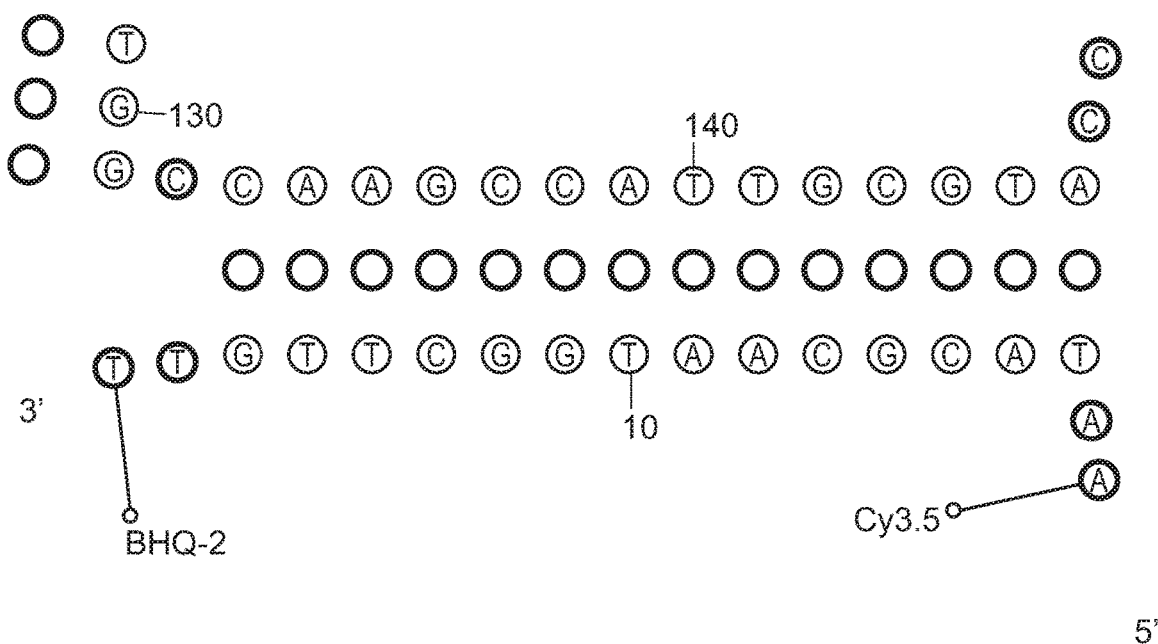
Figure 13:
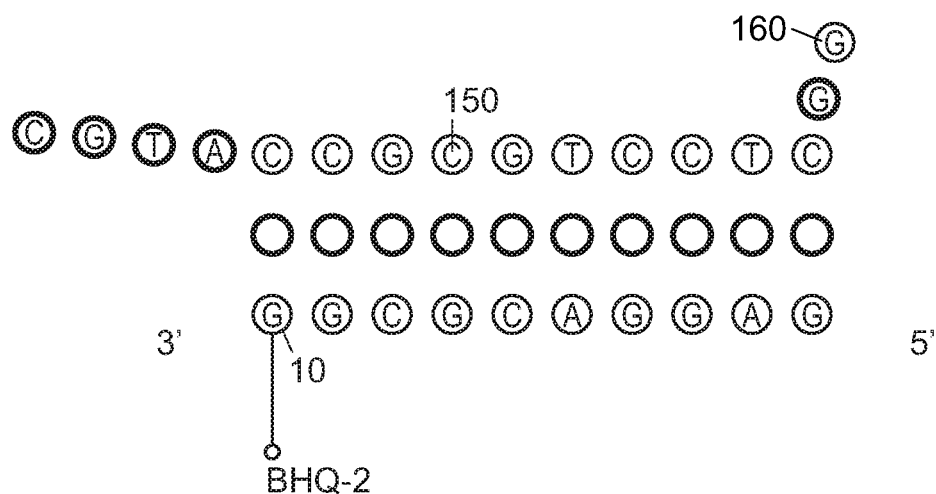
Figure 13:
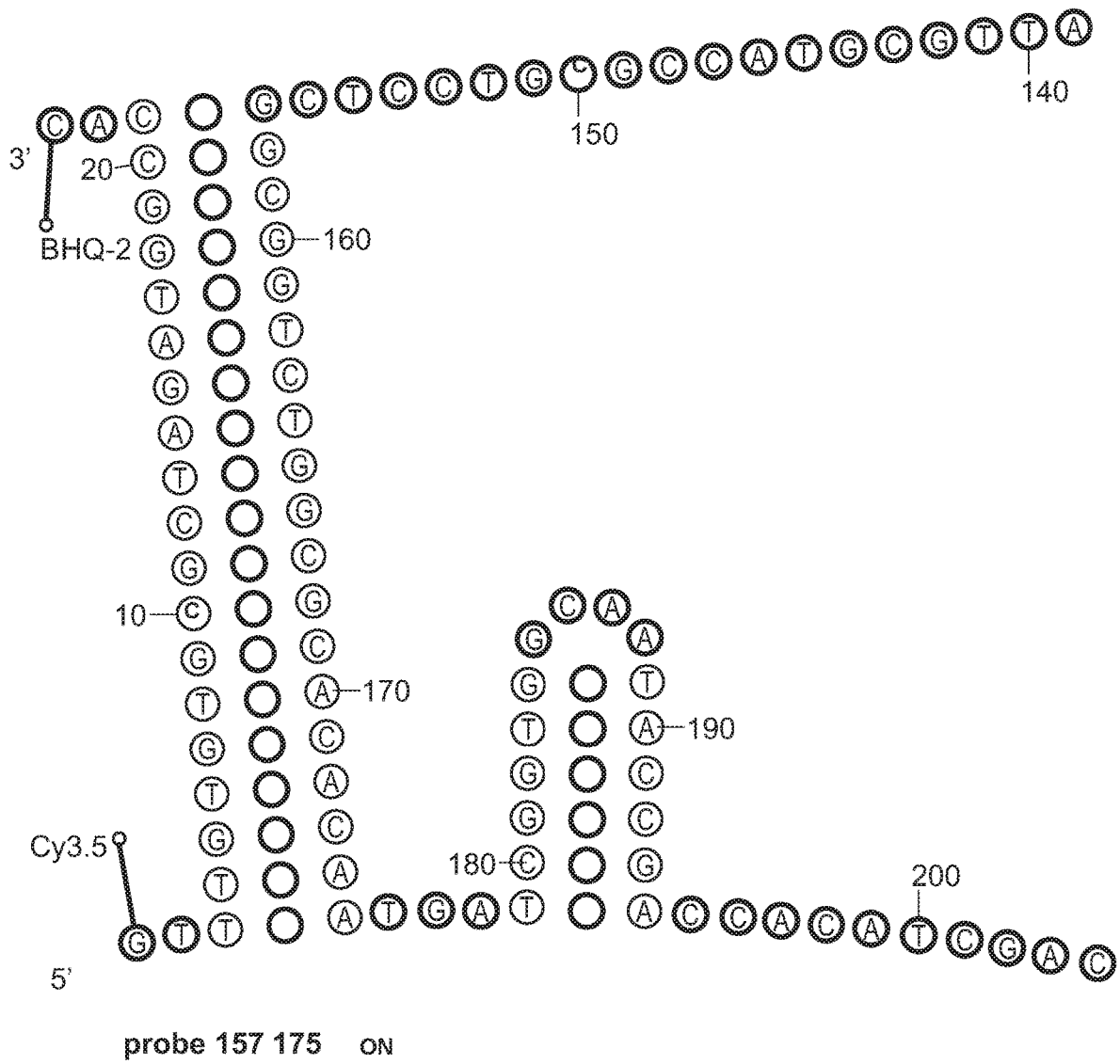
Figure 13:
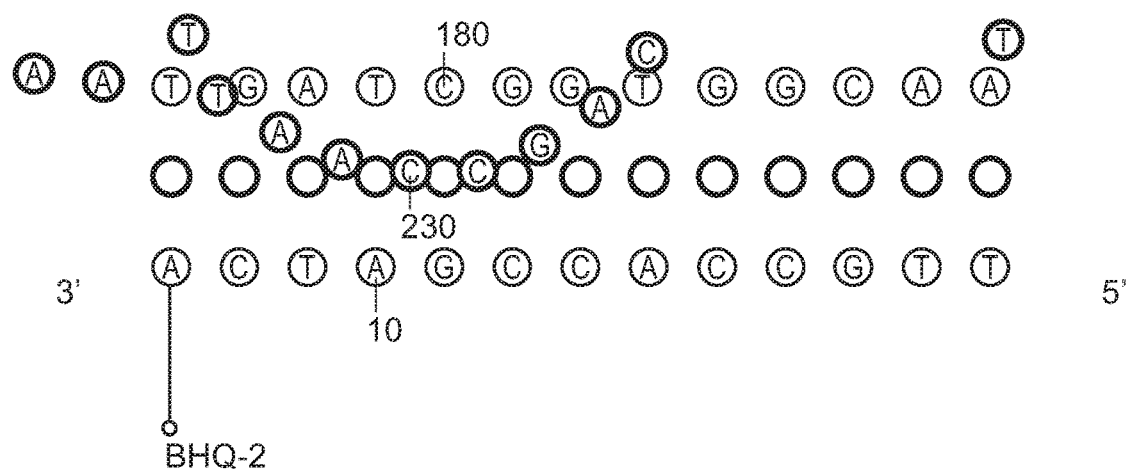
Figure 13:
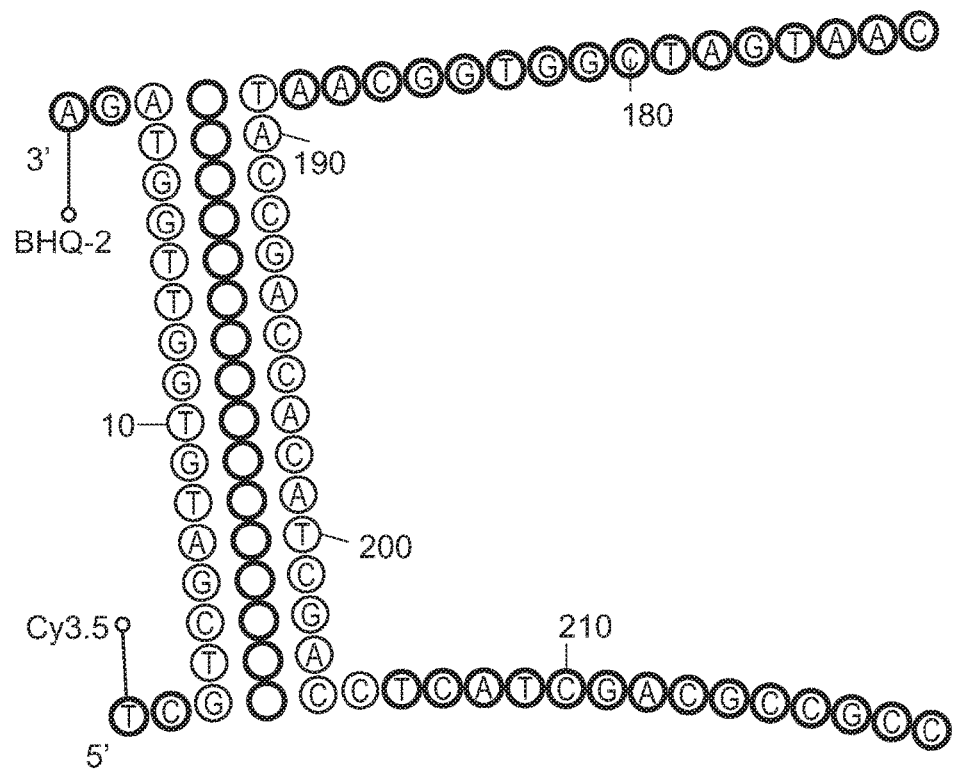
Figure 13:
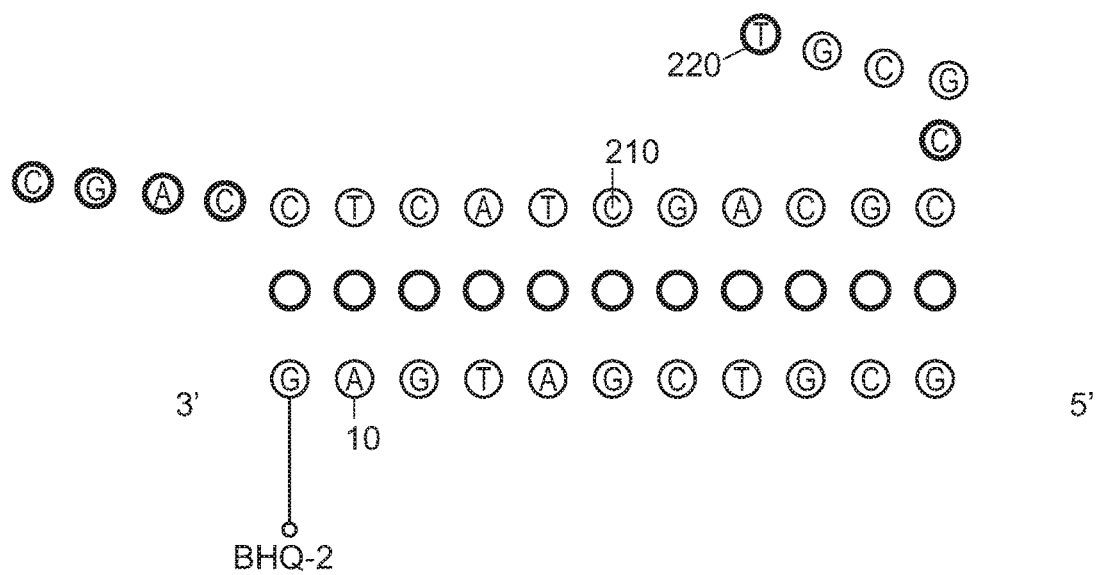
Figure 13:
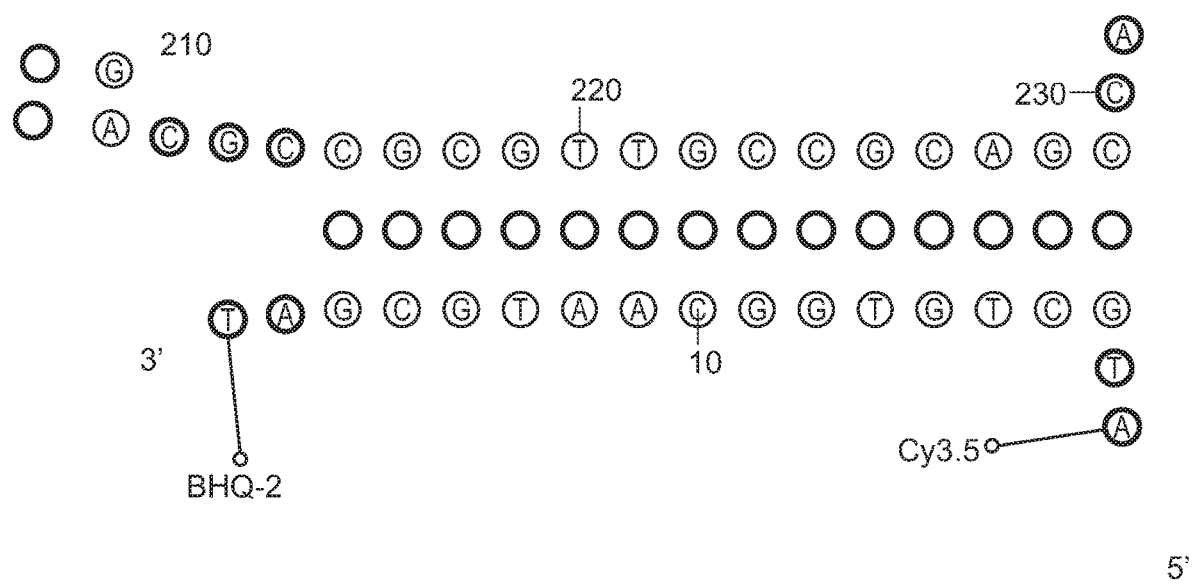
Figure 13:
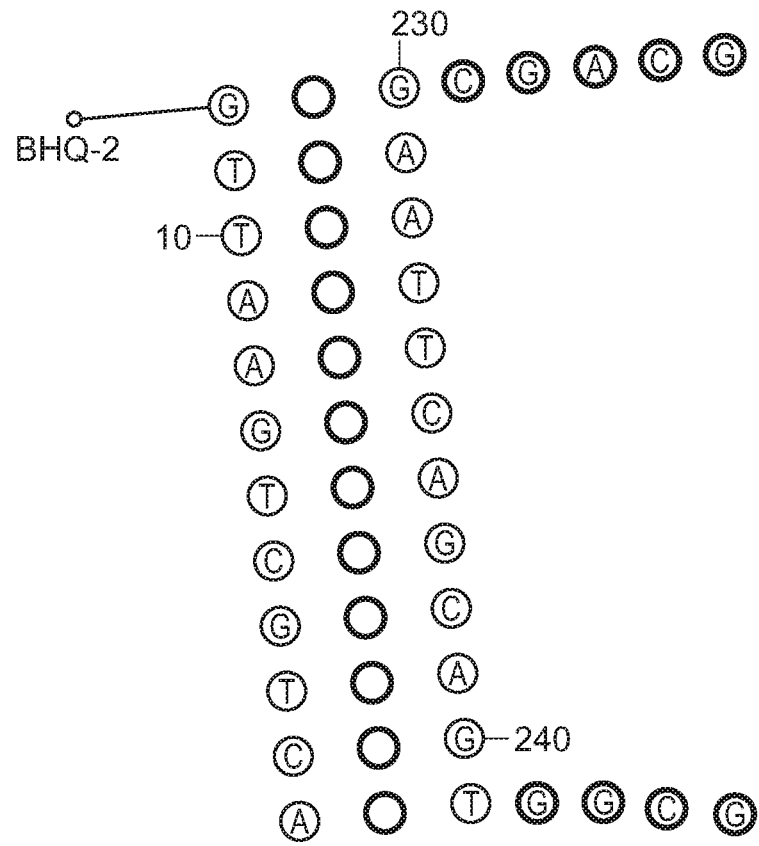
Figure 13:
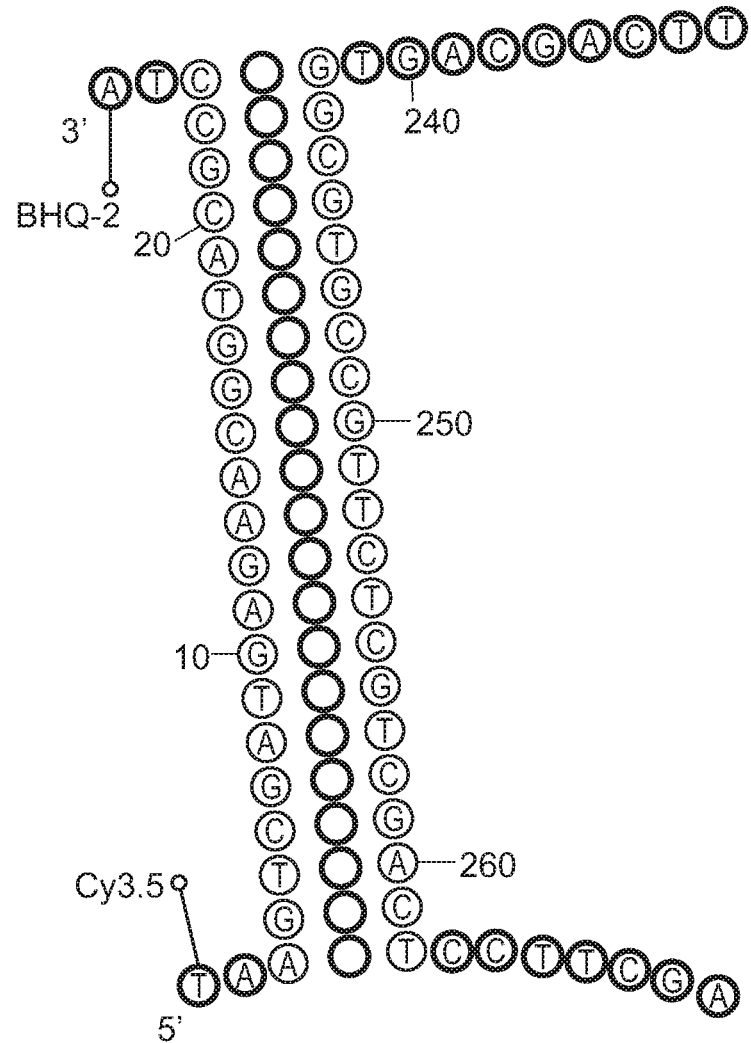
Figure 13:
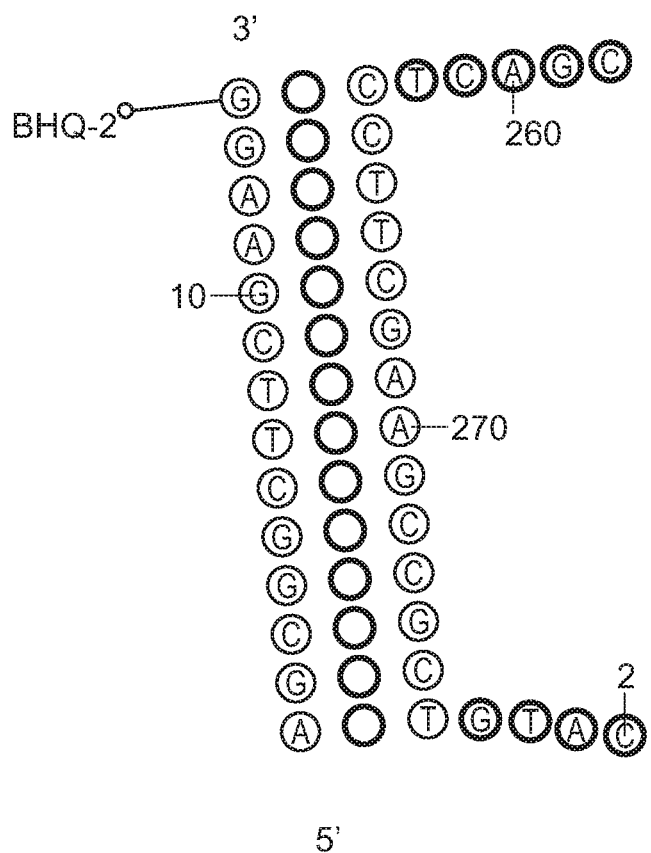
Figure 13:
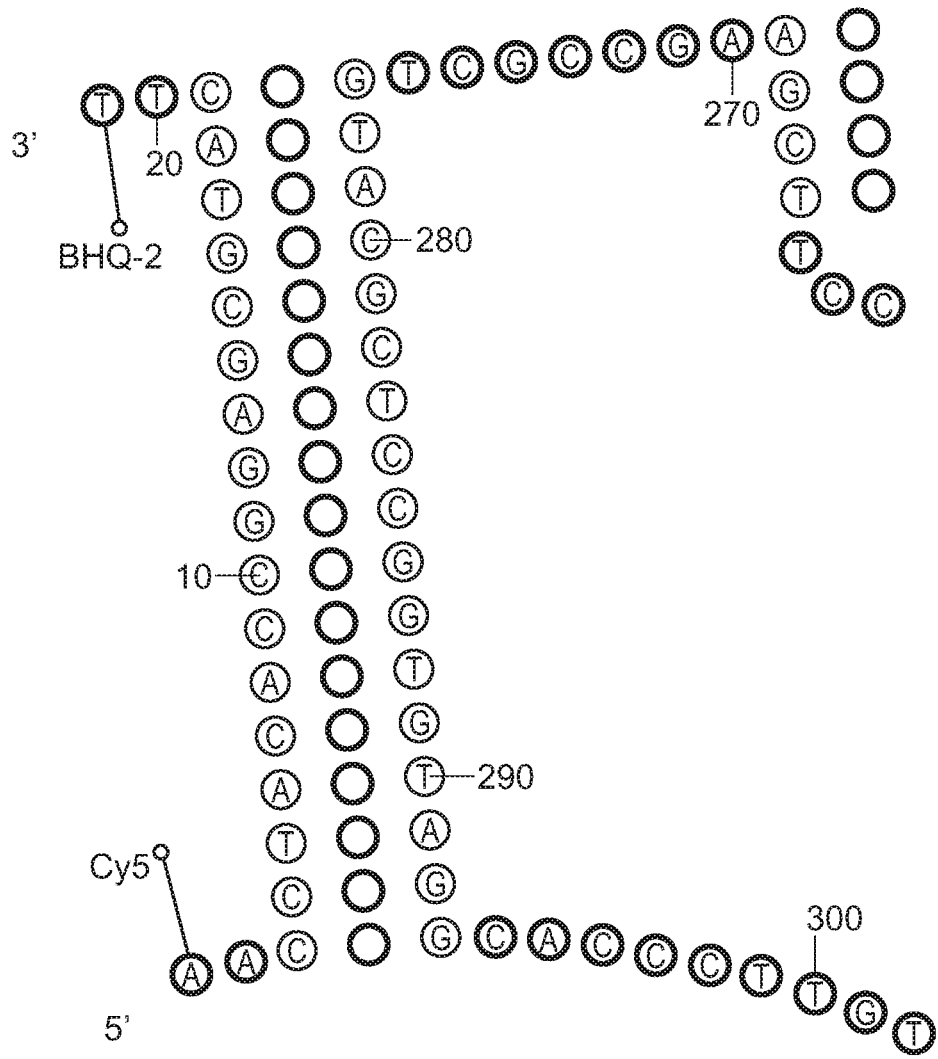
Figure 13:
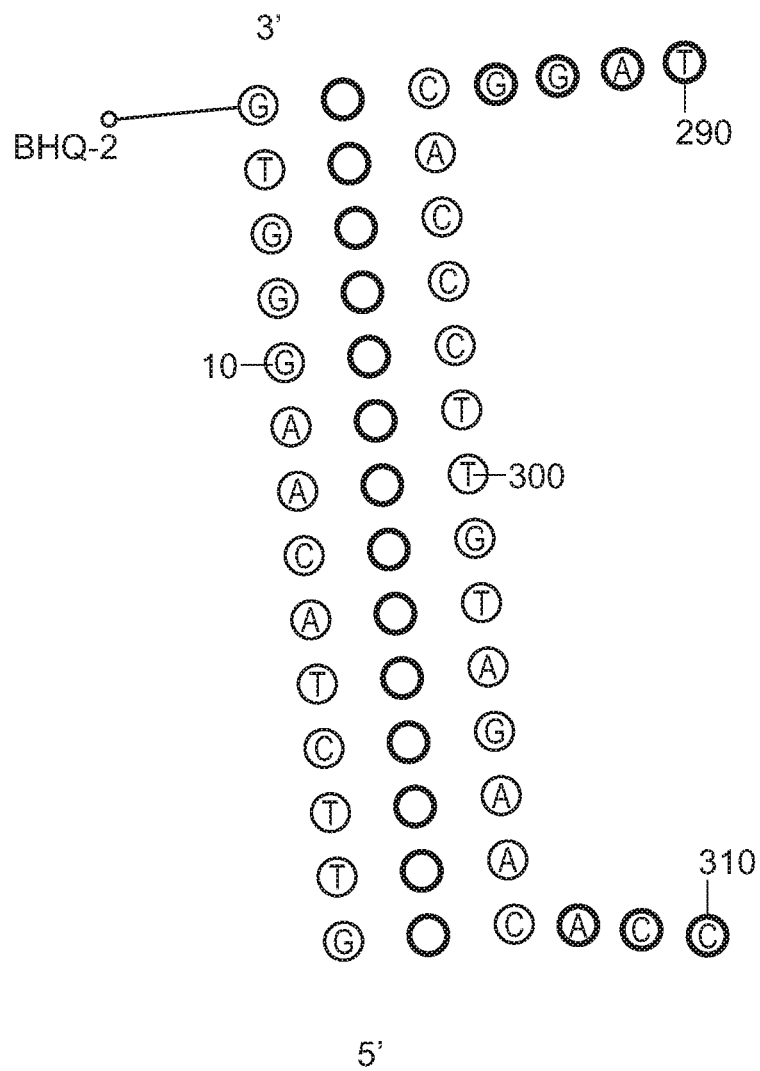
Figure 13:
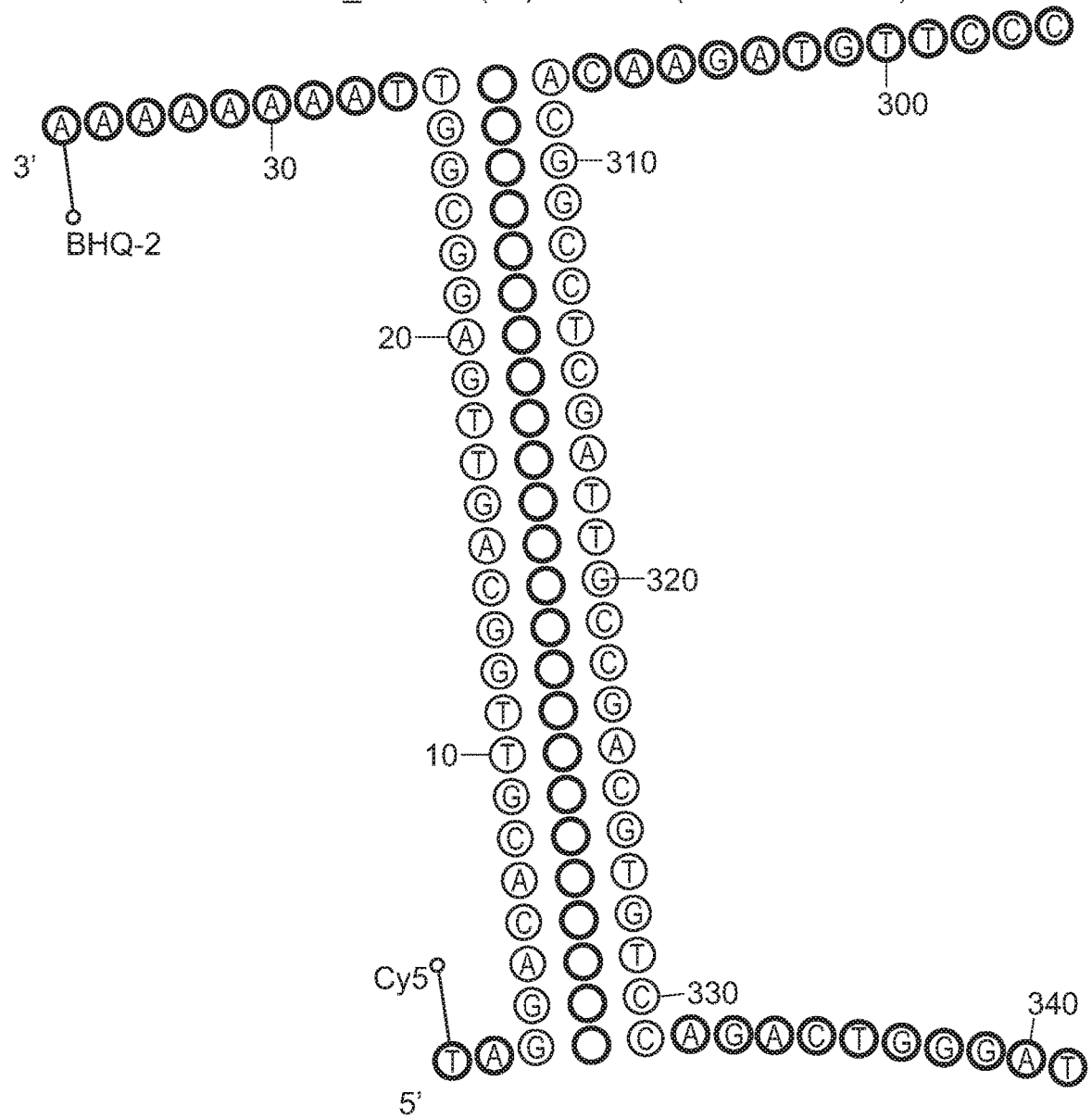
Figure 13:
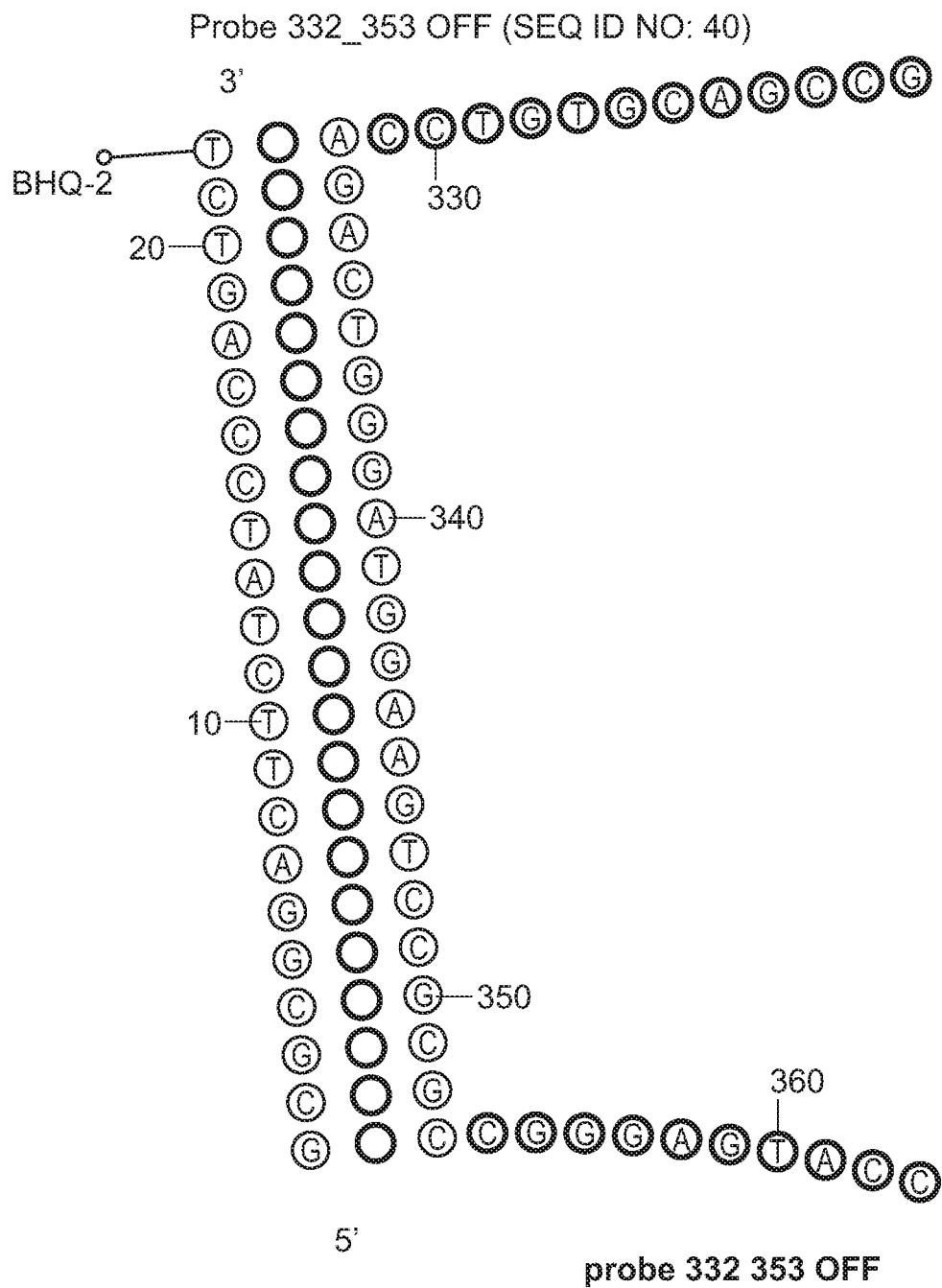
Figure 13:
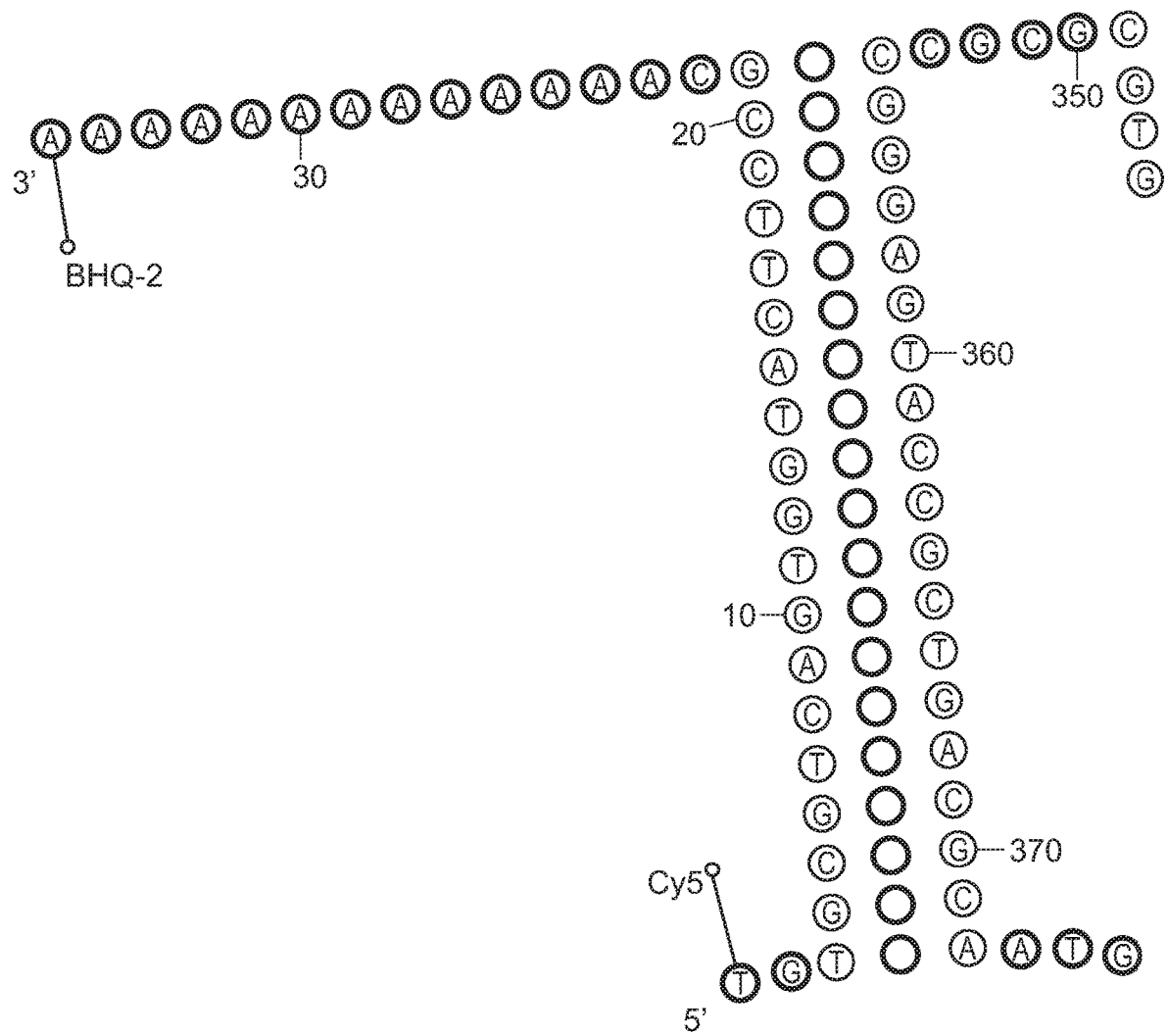
Figure 13:
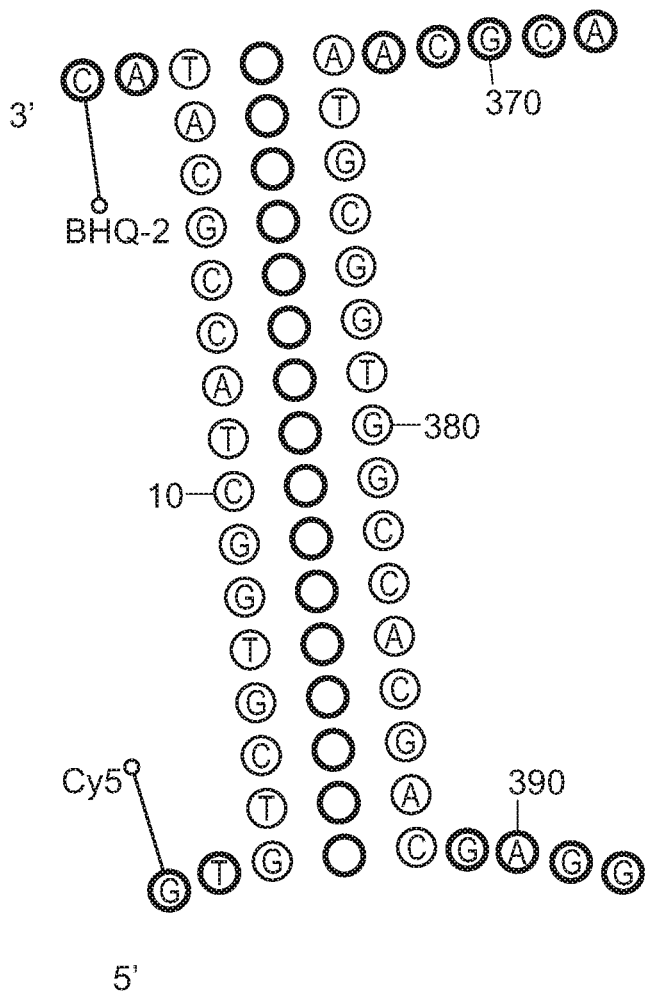
Figure 13:
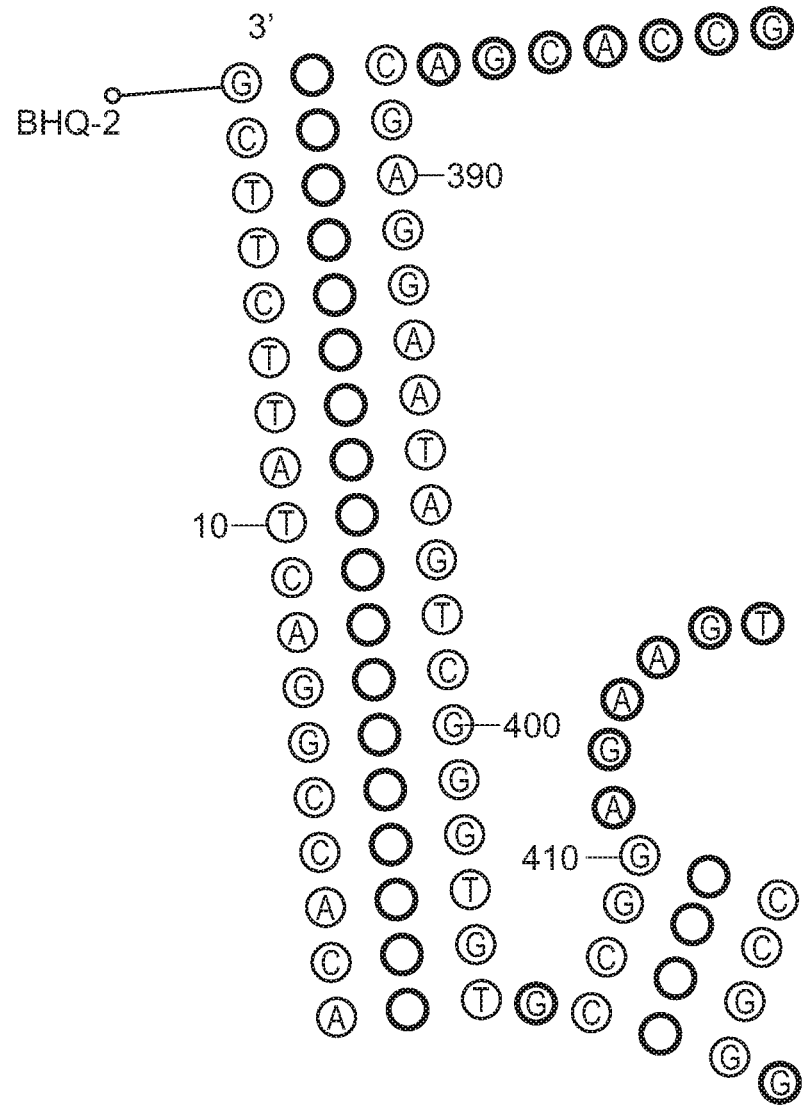
Figure 13:
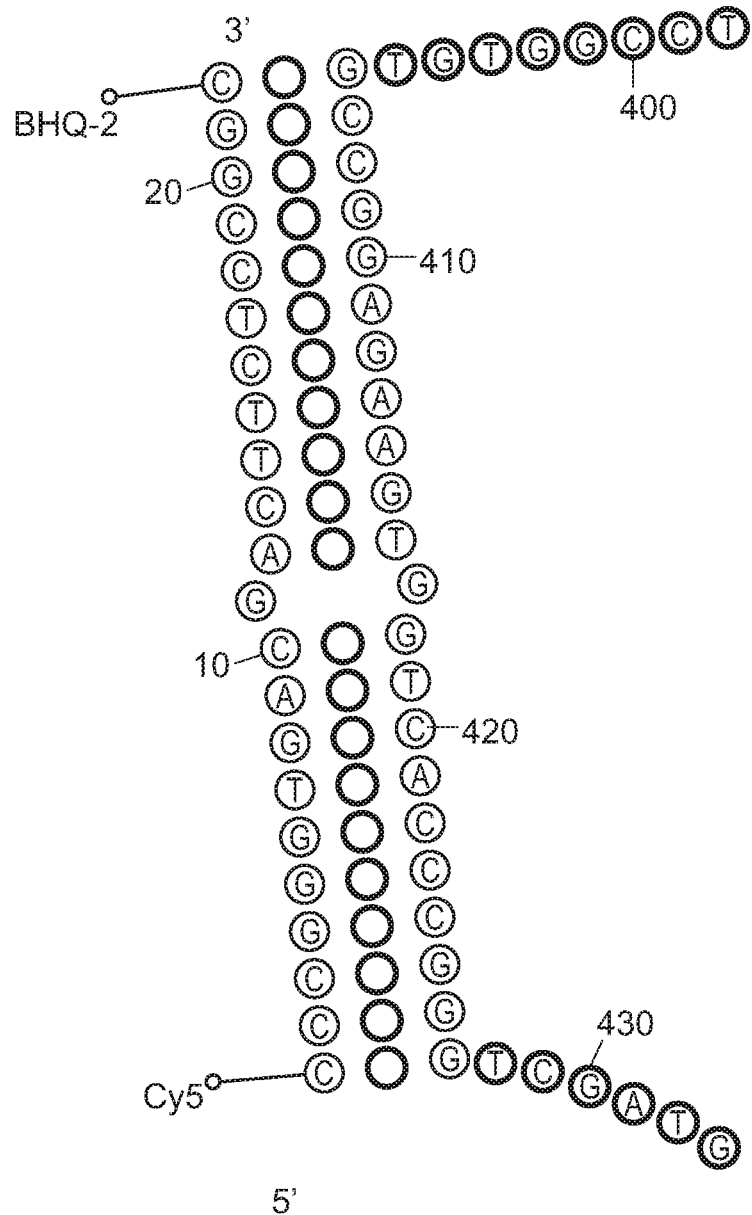
Figure 13:
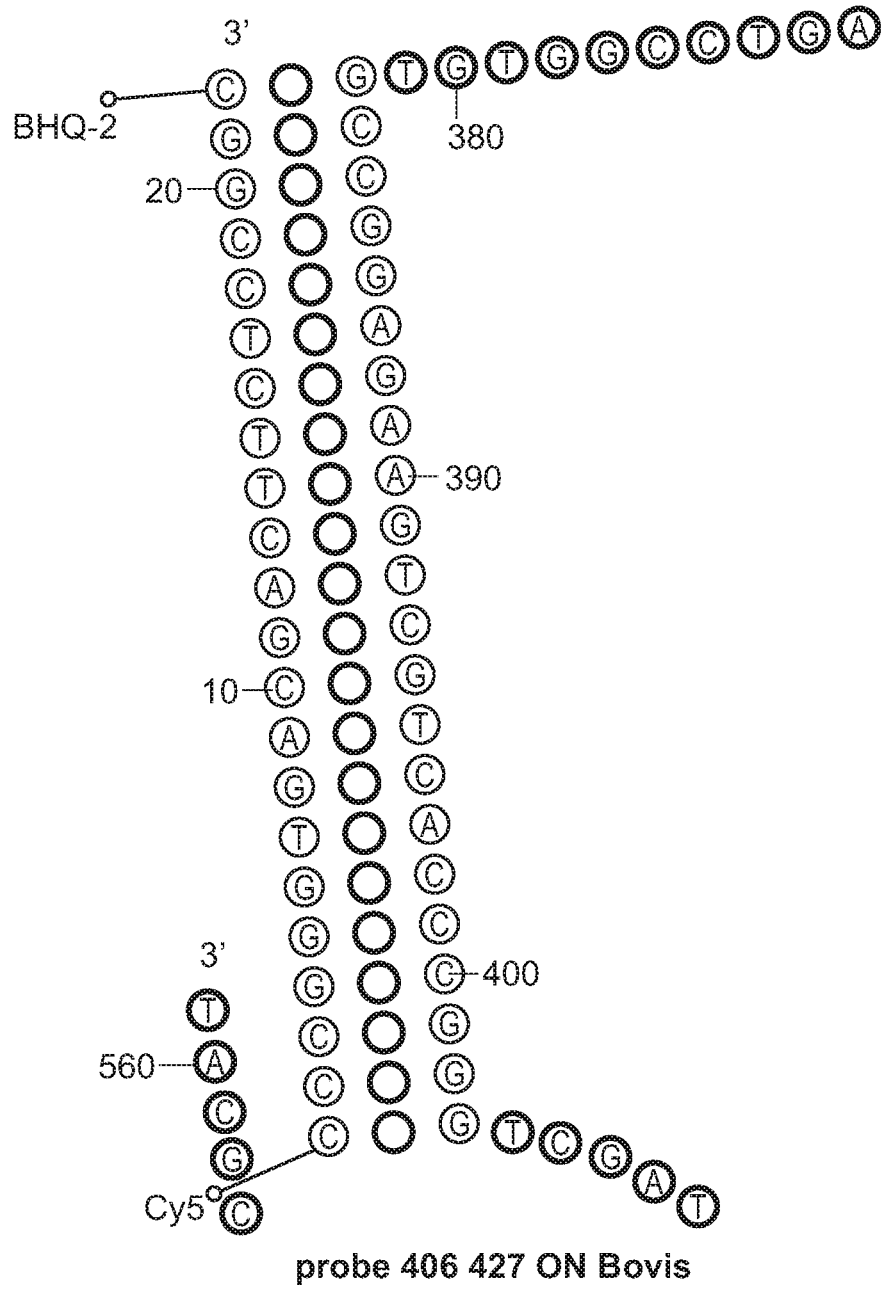
Figure 13:
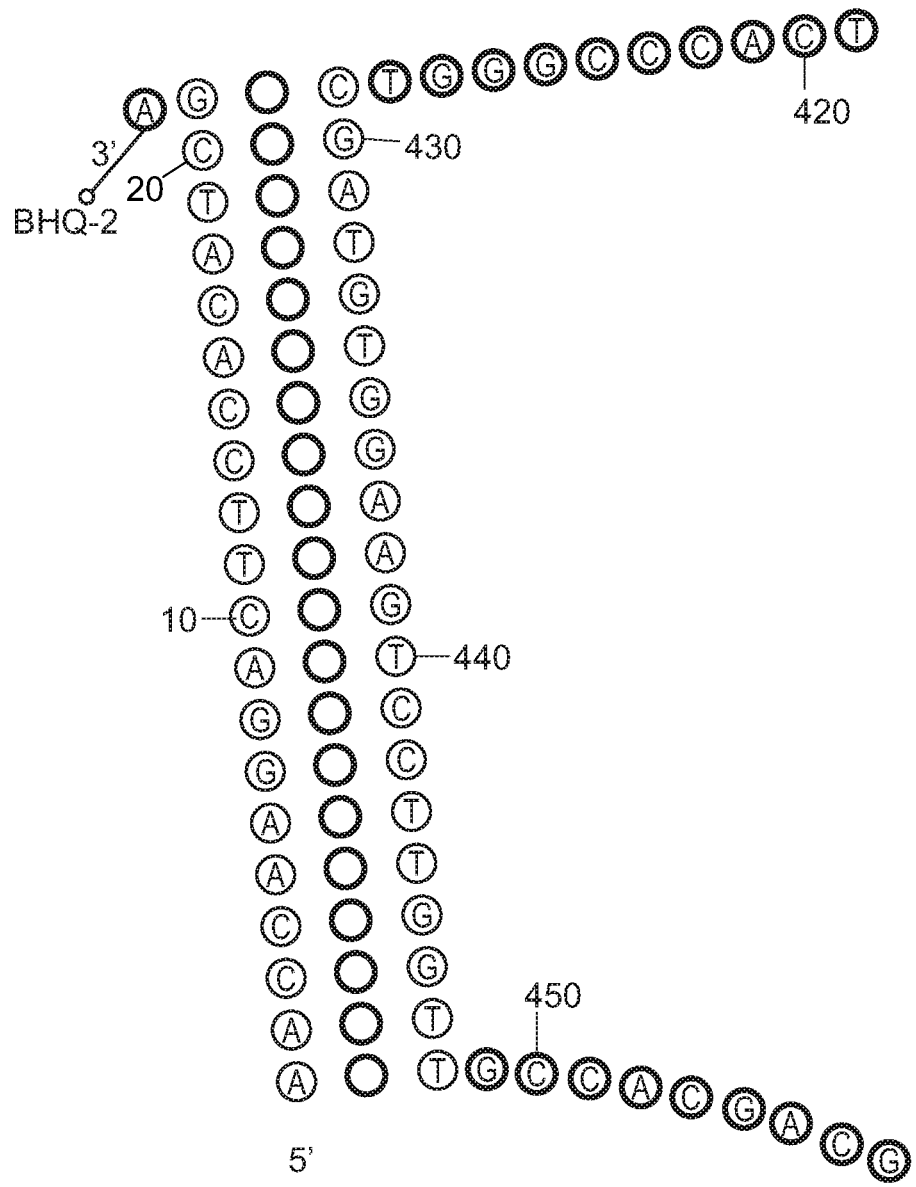
Figure 13:
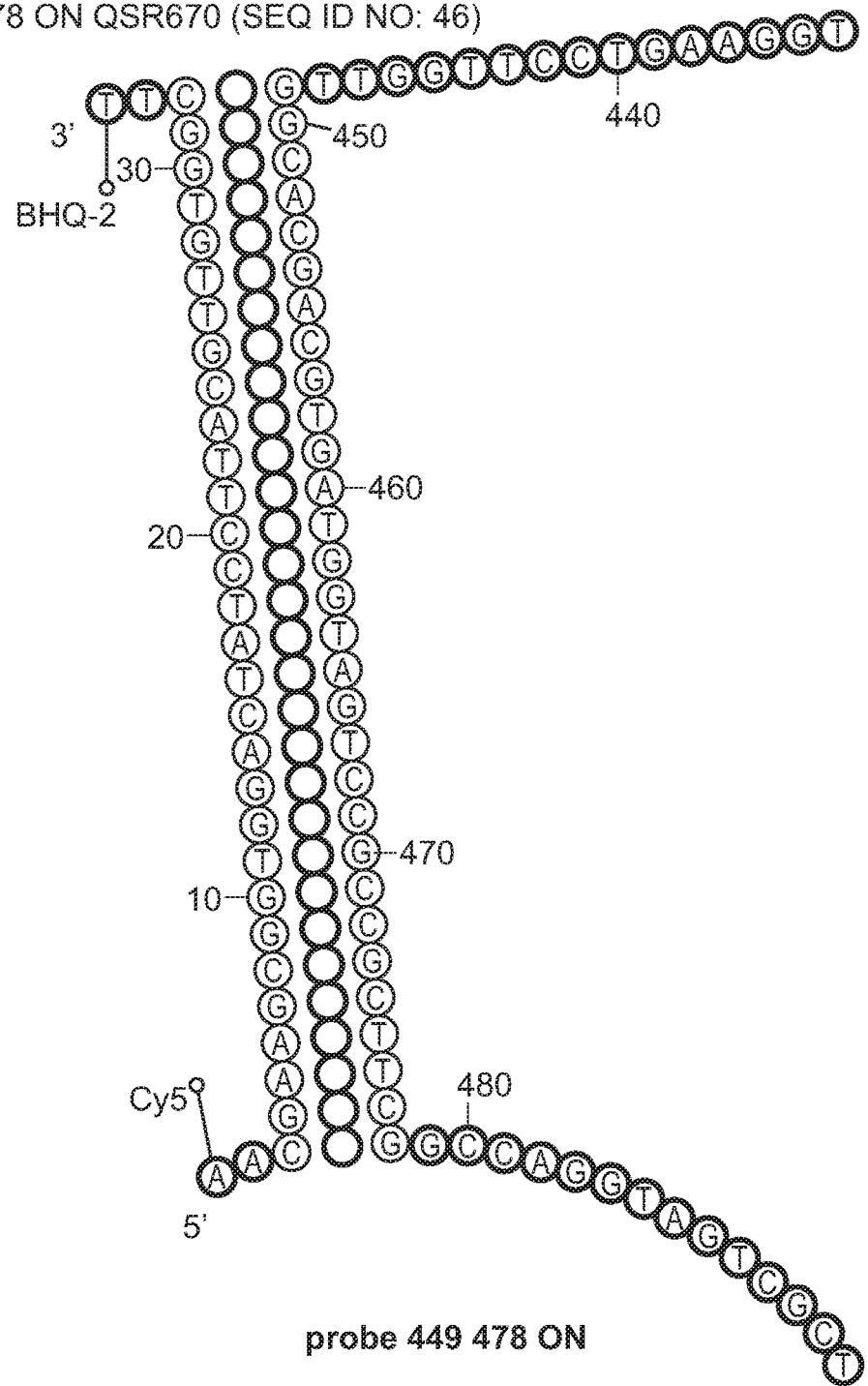
Figure 13:
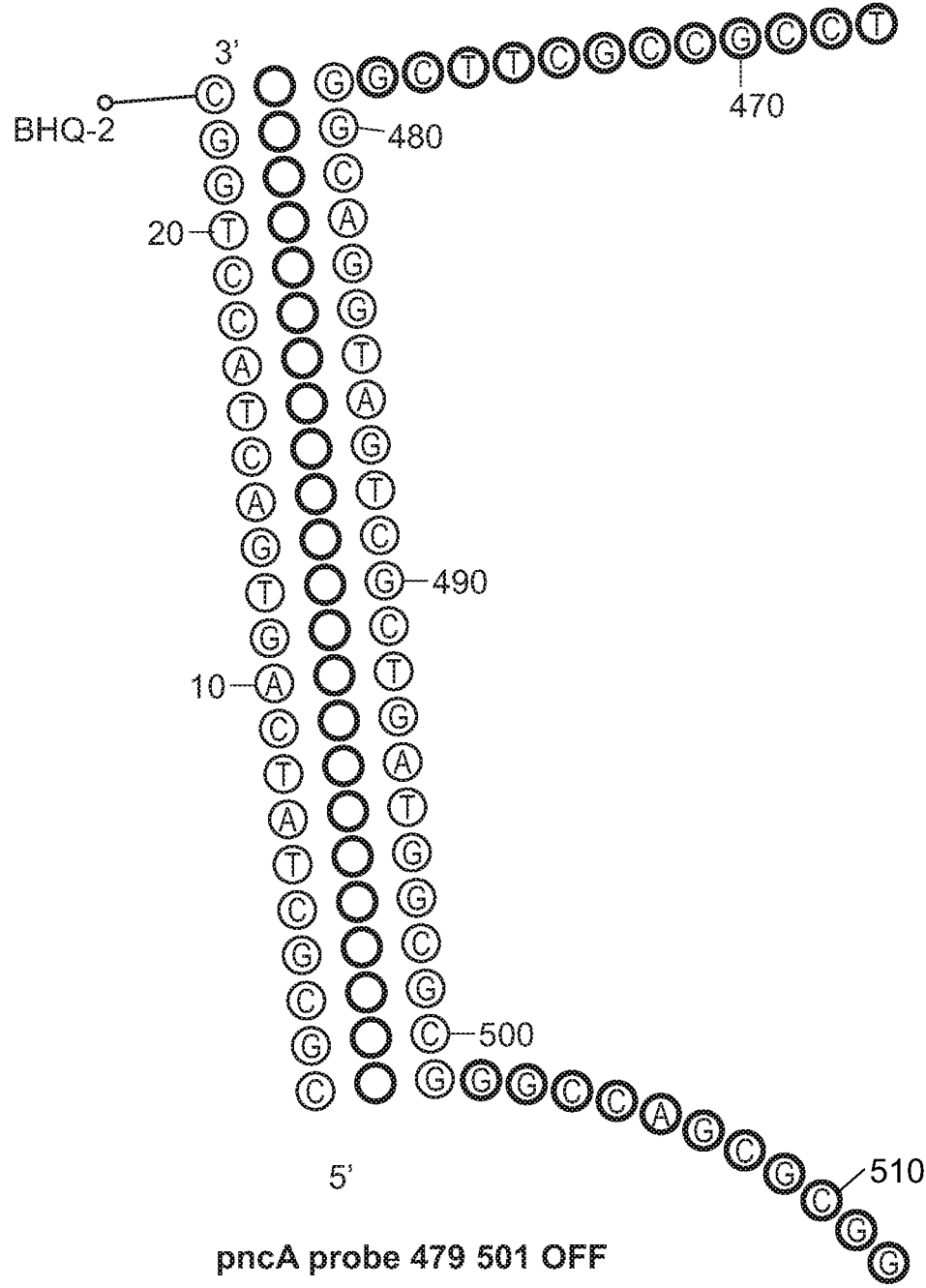
Figure 13:
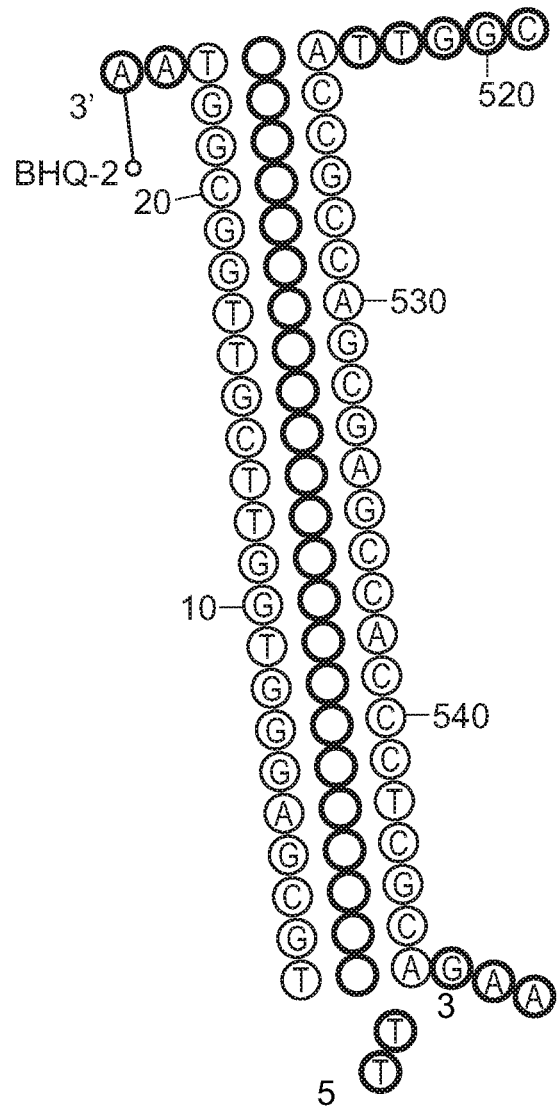
Figure 13:
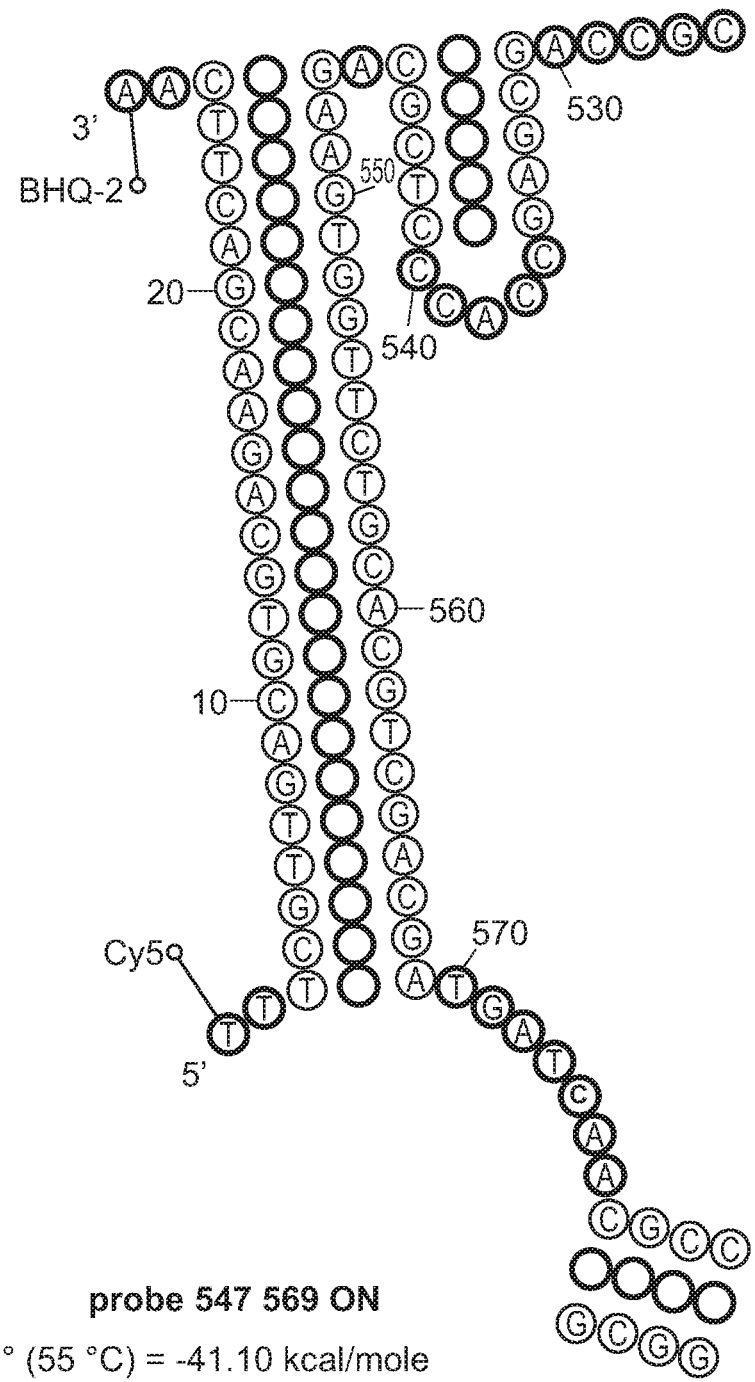
Figure 13:
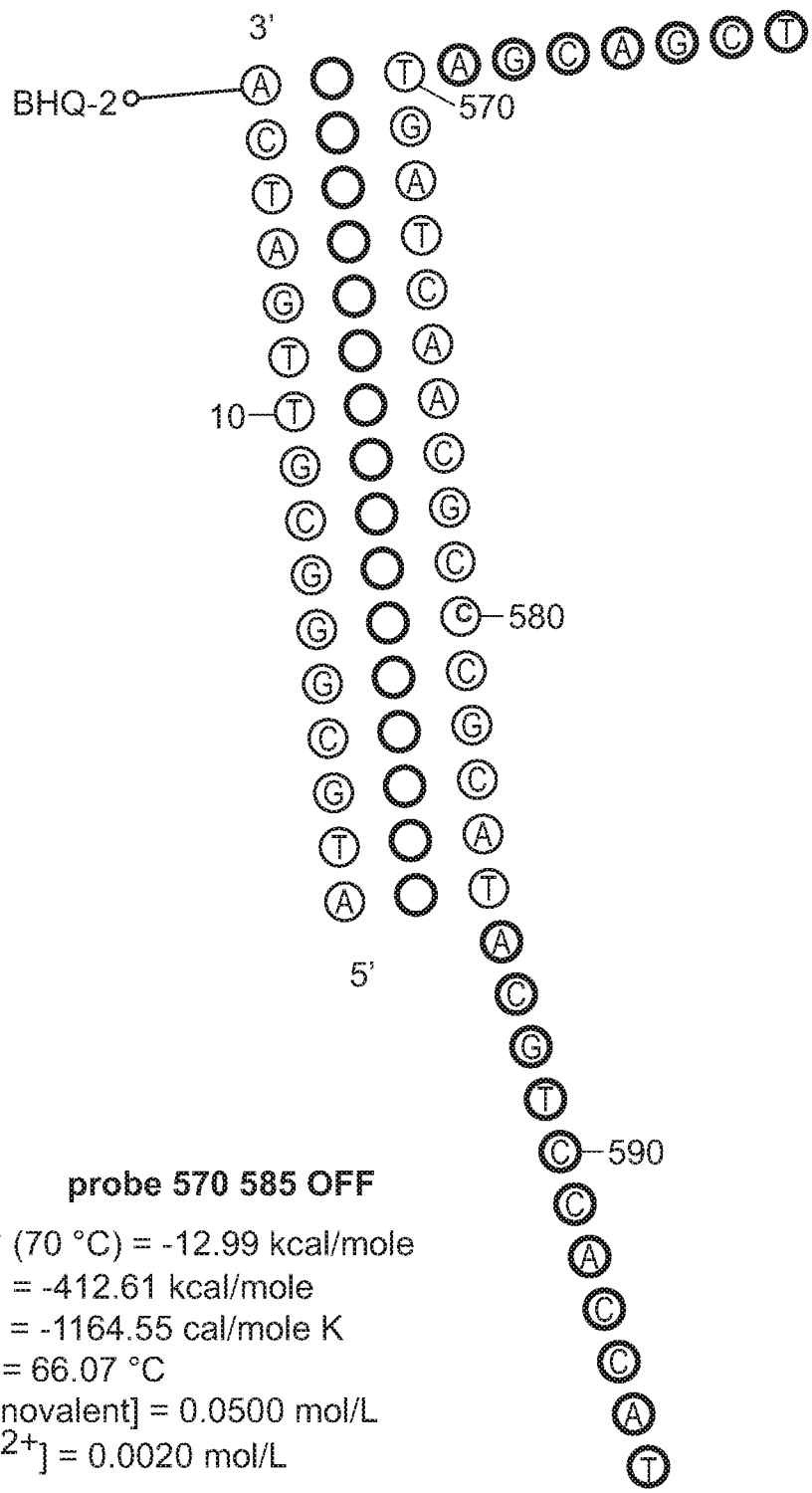

At the end of 60 cycles the probe target hybridizations were analyzed by melt curve analysis using the first derivative for each fluor separately for the temperatures between 25° C. to 95° C. Results are presented in FIGS. 6-11 as the first derivative for the fluorescence signals of all probes for the genes inhA promoter, katG, rpoB, plus the $1^{st}$ internal control and the $2^{nd}$ internal control all in the same colored fluorophore, Quasar 670, as a function of the temperature. FIG. 6 shows the signals of the $1^{st}$ and $2^{nd}$ internal controls in the absence of added *M. tuberculosis* DNA. FIGS. 7-11 reactions were initiated with approximately 1000 copies of genomic DNA of different strains of *M. tuberculosis*.

Example 3

Multiplex Detection of Drug Resistance in Three Different Genes for Strains of *M. Tuberculosis*

A tetraplex LATE PCR assay was used to detect drug resistance in the three genes inhA promoter (promoter region), katG, and rpoB, plus an amplifiable 1st internal control and a non-amplifiable 2nd internal control. Results are shown in FIGS. 24-27. In FIG. 24, the lines 190 are the drug sensitive strain H37Rv for all three genes while line 191 is resistant strain for katG only (S315T, a serine located at amino acid position 315 changed to a tyrosine). For FIG. 25, sensitive strain is line 200 while inhA promoter resistant only strain, line 201 contained a single nucleotide change (T/C) at minus 8 position in the promoter region. For FIG. 26, line 210 is the sensitive strain while line 211 contains an rpoB mutation only (D516V, an aspartic acid to valine). For FIG. 27, line 220 is the sensitive strain, while line 221 contains a double rpoB mutation only (D516A, aspartic acid to alanine and H526N, histidine to asparagine).

LATE PCR amplifications were carried out in a 25 µl volume in a reaction mixture containing 1×PCR buffer (Invitrogen, Carlsbad, Calif.), 3 mM MgCl2, 300 nM dNTPs, 600 nM of the PrimeSafe 1, 50 nM limiting primer and 1000 nM excess primer for each primer set, 2.0 units of Taq DNA Polymerase (Invitrogen, Carlsbad, Calif.), 50 nM of On Probe and 150 nM of Off Probe for all probes except for rpoB Probe 5_On (25 nM), rpoB Probe 5_On_G (75 nM). For each strain tested approximately 1000 genomes equivalents were used and amplification reactions were run in duplicate. The thermal profile for the amplification reaction was as follows: 97° C./5 s-75° C./45 s for 60 cycles, followed by 10 min at 75° C. This is followed by a melt starting at 25° C. with 1° C. increments at 20 s intervals to 98° C. At the end of 60 cycles the probe target hybridizations were analyzed by melt curve analysis using the first derivative for each fluorophore separately for the temperatures between 25° C. to 95° C. Results are presented in FIGS. 24-27 as the first derivative for the fluorescence signals of all probes for the genes inhA promoter, katG, rpoB, plus the 1st internal control and the 2nd internal control all in the same colored fluorophore, Quasar 670, as a function of the temperature.

Example 3

Figure 29:
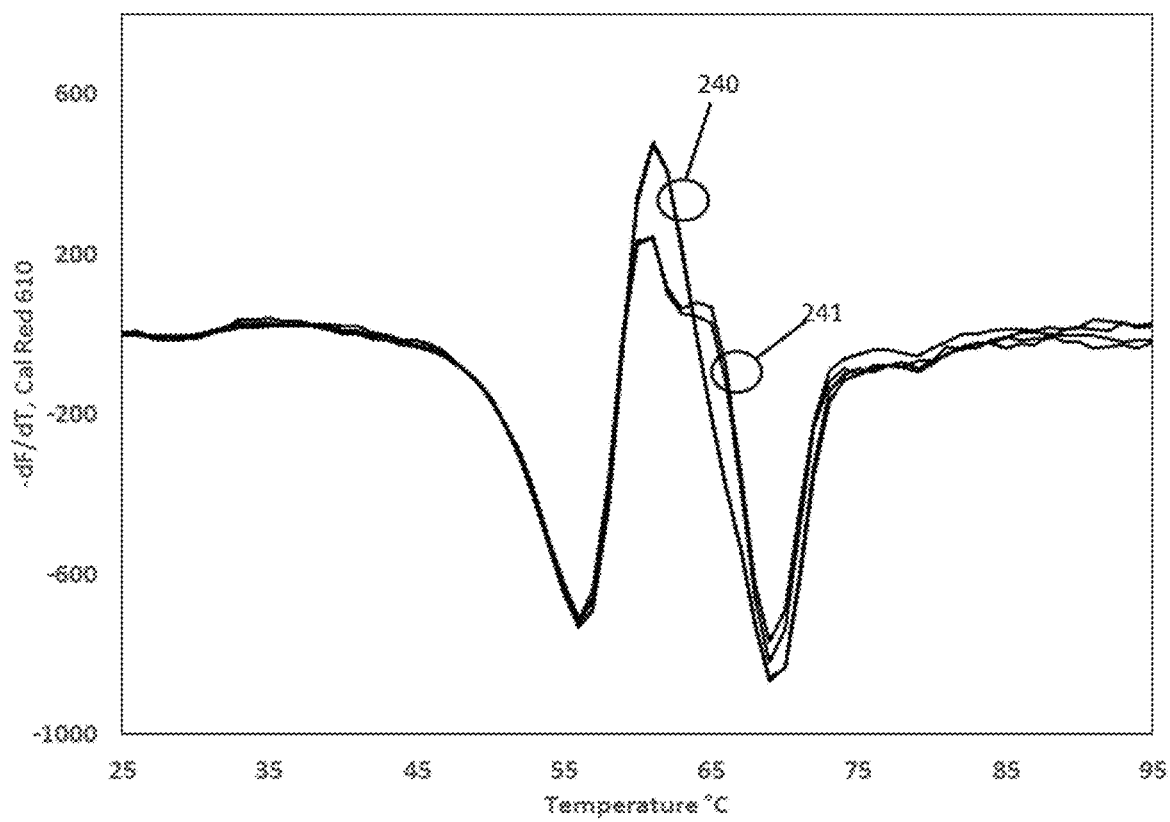
FIG. 29 shows exemplary temperature-dependent fluorescence data from a single tube, two-color, pncA assay, with panel (A) showing Cal Red 610 and panel (B) showing Quasar 670.
Figure 29:
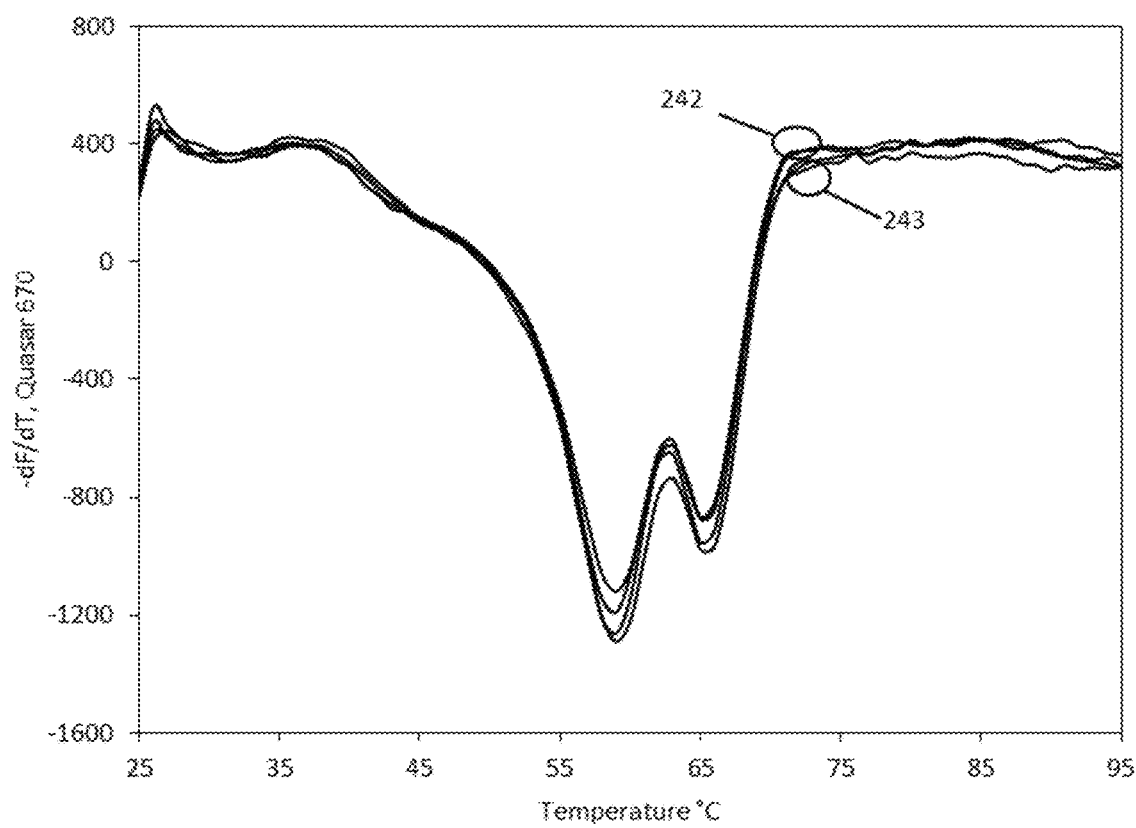

Mutation Detection Assay Using 2 Colors in Different Strains of *M. Tuberculosis* for the Pyrazinamide Gene A monoplex LATE PCR assay (Design I) was used to detect mutational differences from the sensitive strain in the pyrazinamide gene. The 561 base pair amplicon includes the entire coding sequence of the pncA gene. It is coated with 31 Lights-On probes and Lights-Off probes in two fluorescent colors (Cal Red 610 and Quasar 670). Probe pairs in a single color are linearly positioned on approximately on half of the target sequence, resulting in analysis of the target sequence in two separate fluorescent segments. Characteristic fluorescent signatures (first derivatives) of a normal wild-type (PZA sensitive) target and a few of the many possible non-wild-type (PZA resistant) sequences are shown in FIGS. 28-29.

FIGS. 28A and 28B show the results in Cal Red 610 and Quasar 670 fluorescence respectively, where lines 230 and 232 are sensitive strain H37Rv while line 231 and 233 are the mutational strain containing a single base change guanine(G) at position three to a cytosine(C) for the pyrazinamide gene. In FIG. 28A both signatures are the same indicating no mutation within this portion of the gene. While the signatures in FIG. 28B are clearly different showing the presence of a mutation. FIGS. 29A and 29B show the results of a comparison of the same sensitive strain but with a different mutational strain that contained an insertion of a thymidine (T) between nucleotide position 321 and 322. FIG. 29A, shows the results in Cal Red 610 where line 240 is sensitive strain H37Rv while line 241 is the mutational strain which is plainly different from the fluorescent signature of the sensitive strain showing the presence of a mutation. The Quasar 670 results are shown in FIG. 29B, line 242 is sensitive strain and line 243 is the mutational strain and there is no difference between the fluorescent signatures in this portion of the gene.

LATE PCR amplifications were carried out in a 25 ul volume consisting of 1×PCR buffer (Invitrogen, Carlsbad, Calif.), 3 mM MgCl2, 300 nM dNTPs, 600 nM of the Primesafe 1, 50 nM limiting primer and 1000 nM excess primer, 1.5 units of Taq DNA Polymerase (Invitrogen, Carlsbad, Calif.), 50 nM of each On probe and 150 nM of each Off probe. For each strain tested approximately 1000 genomes equivalents were used and amplification reactions were run. The thermal profile for the amplification reaction was as follows: 97° C./10 s-75° C./45 s for 60 cycles, followed by 10 min at 75° C., followed by 10 min at 25° C. This is followed by a melt starting at 25° C. with 1° C. increments at 20 s intervals to 98° C. At the end of 60 cycles the probe target hybridizations were analyzed by melt curve analysis using the first derivative for each fluor separately for the temperatures between 25° C. to 95° C. Results are presented in FIGS. 28-29 as the first derivative for the fluorescence signals of all probes as a function of the temperature.

Example 4

Figure 30:
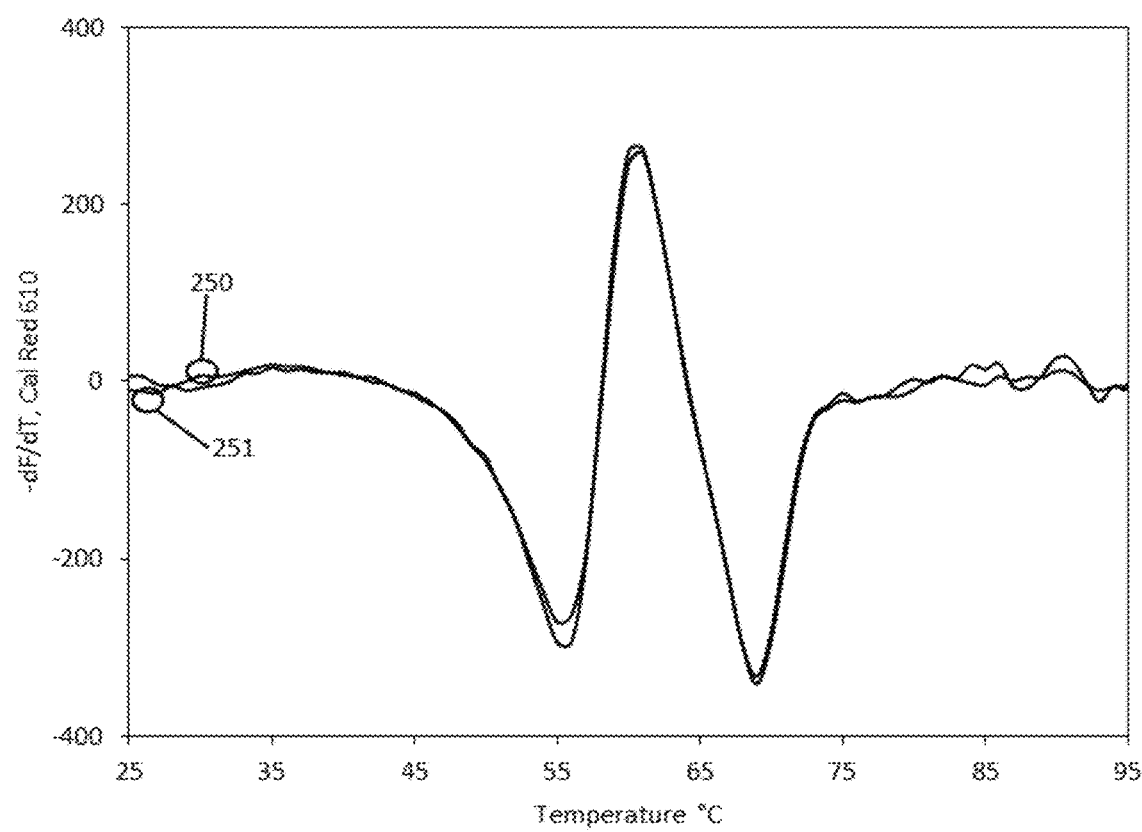
FIG. 30 shows exemplary temperature-dependent fluorescence data from a single tube, two-color Design I pncA assay, with panel (A) showing Cal Red 610 and panel (B) showing Quasar 670.
Figure 30:
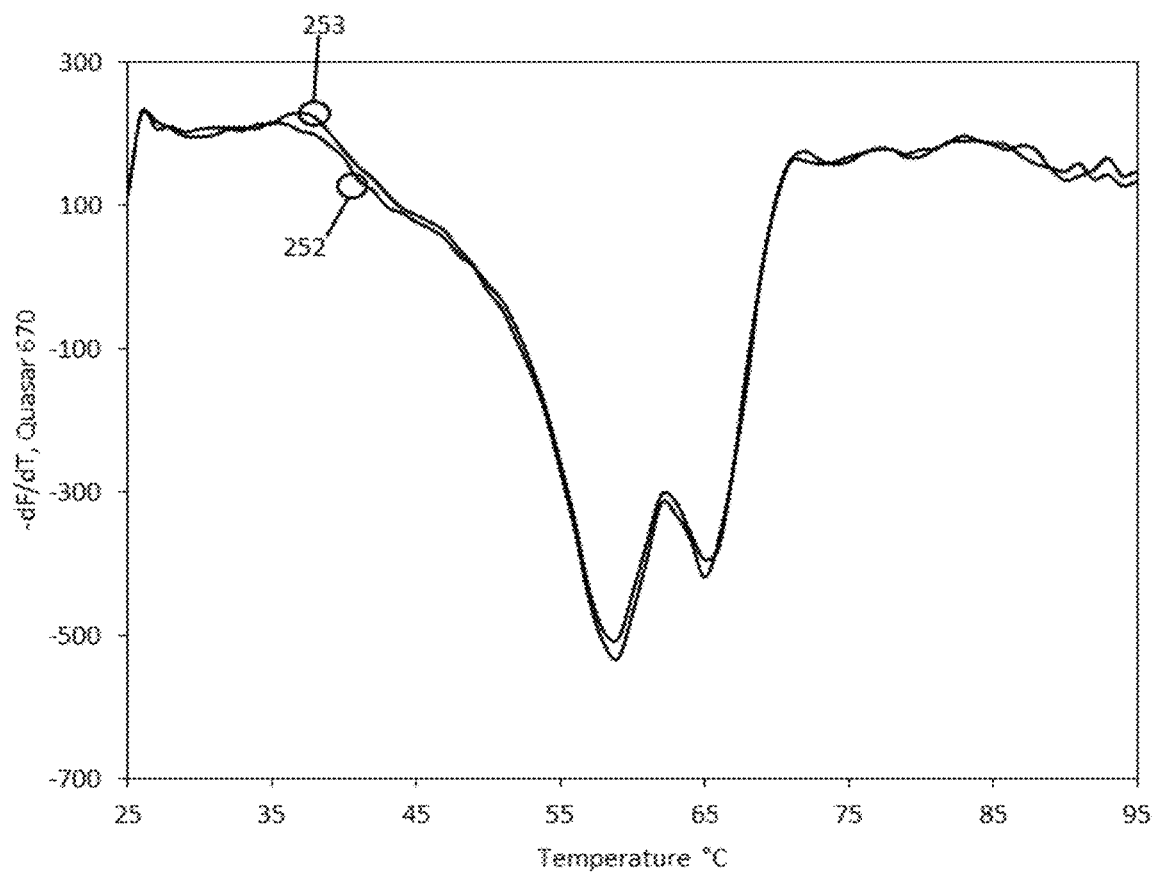
Figure 31:
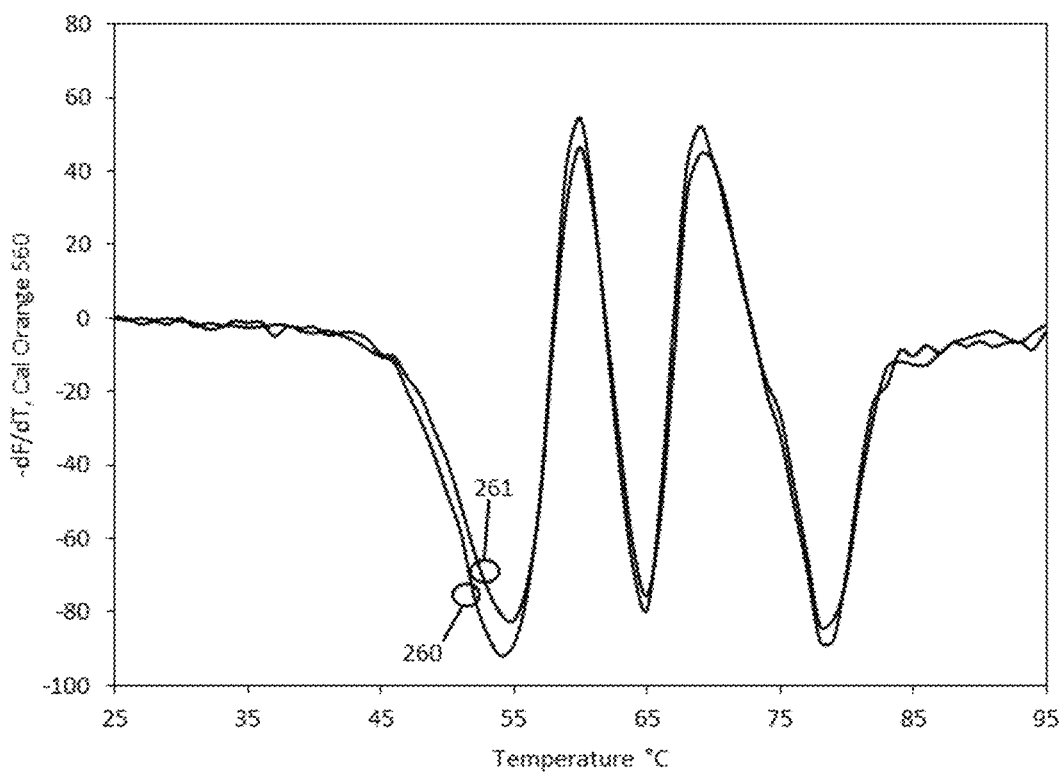
FIG. 31 shows exemplary temperature-dependent fluorescence data from a single tube, three-color Design II pncA assay, with panel (A) showing Cal Orange 560, panel (B) showing Quasar 670 and panel (C) showing Cal Red 610.
Figure 31:
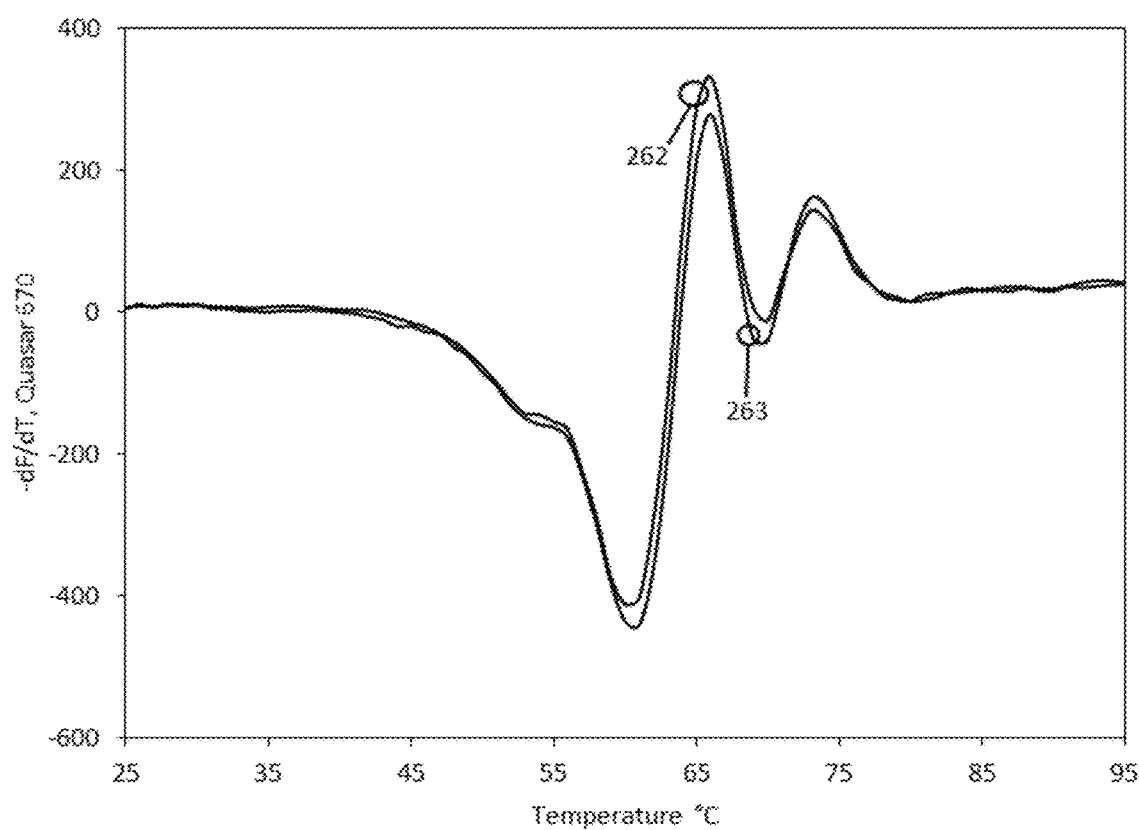
Figure 31:
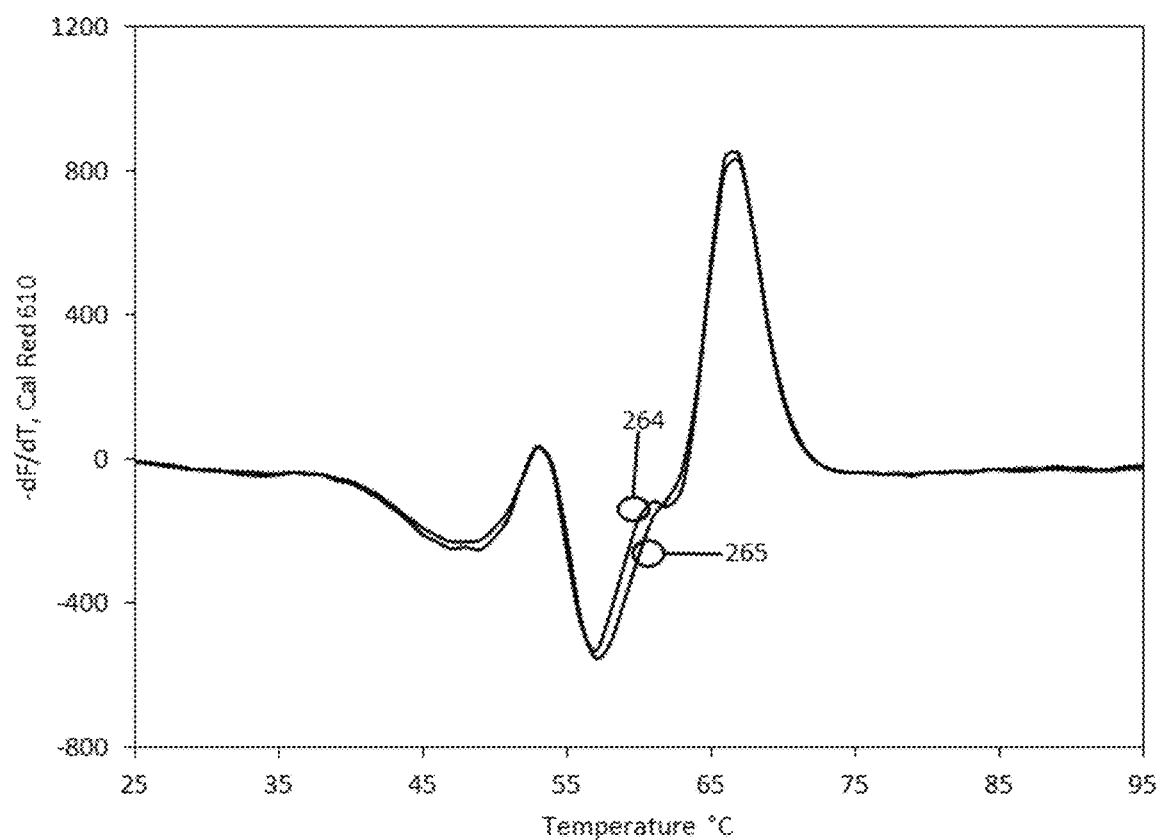
Figure 32:
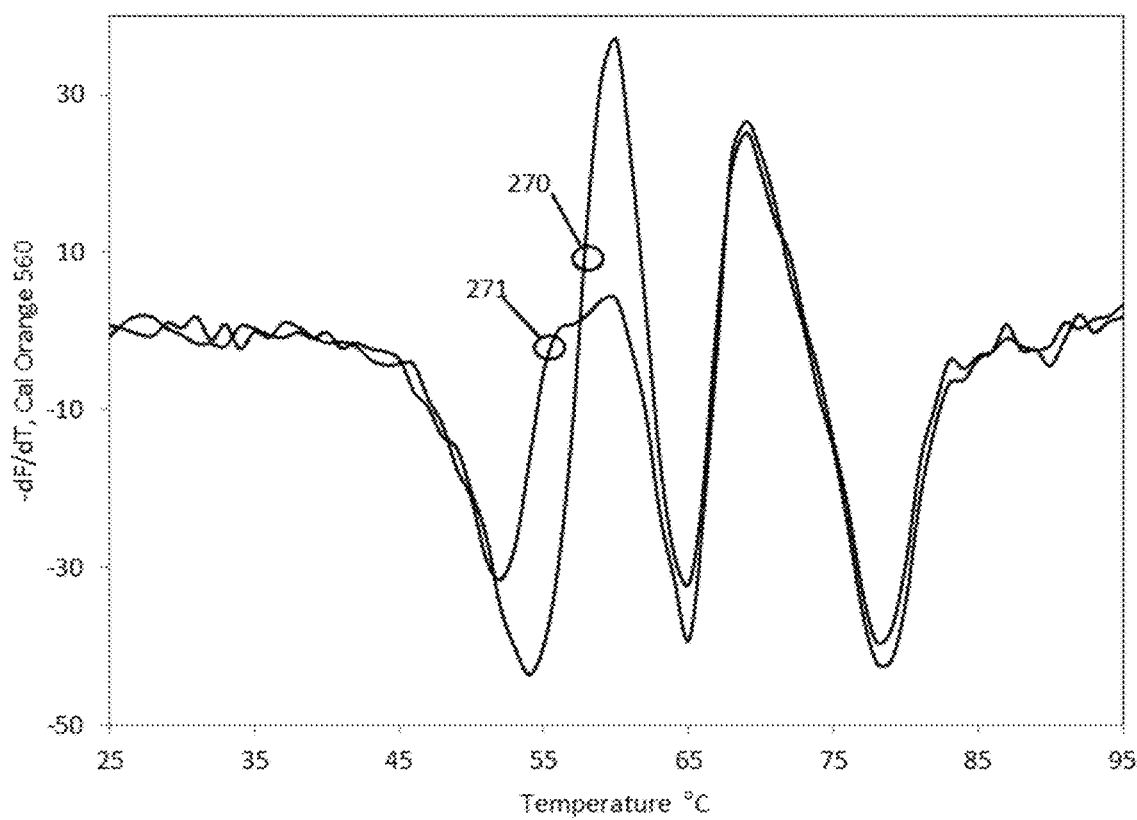
FIG. 32 shows exemplary temperature-dependent fluorescence data from a single tube, three-color Design II pncA assay, with panel (A) showing Cal Orange 560, panel (B) showing Quasar 670 and panel (C) showing Cal Red 610.
Figure 32:
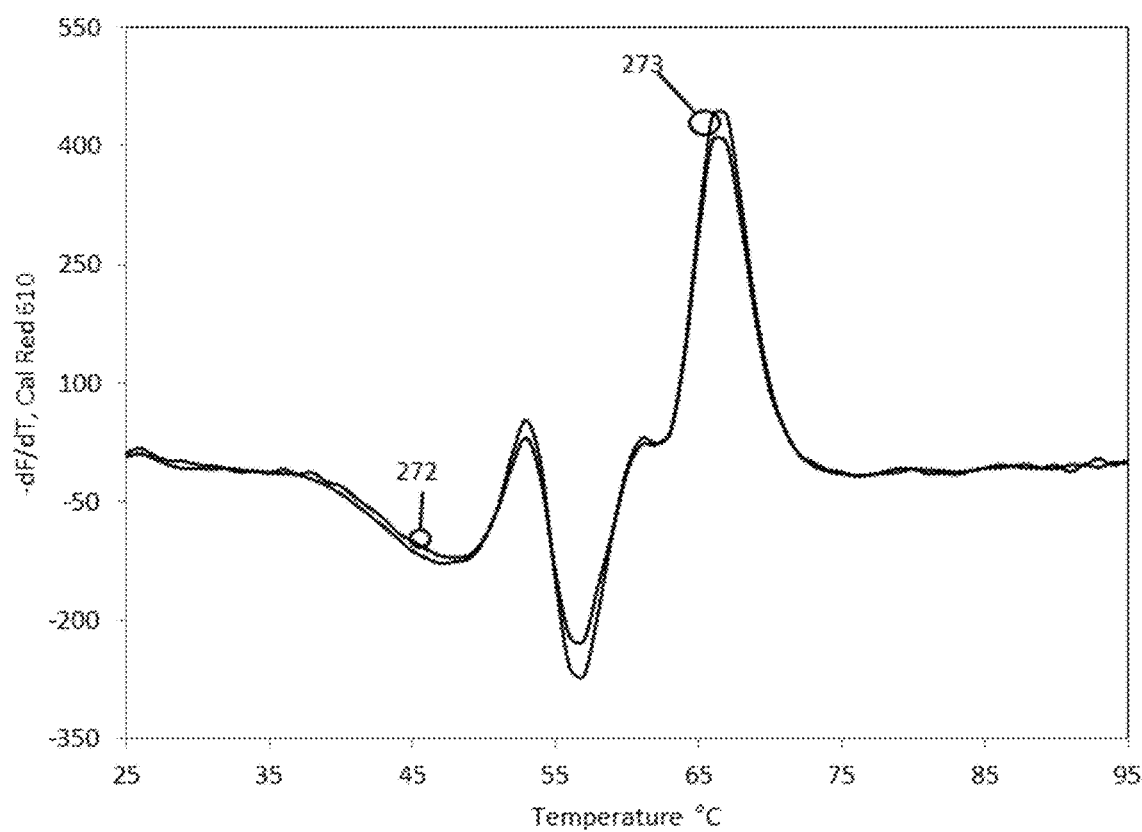
Figure 32:
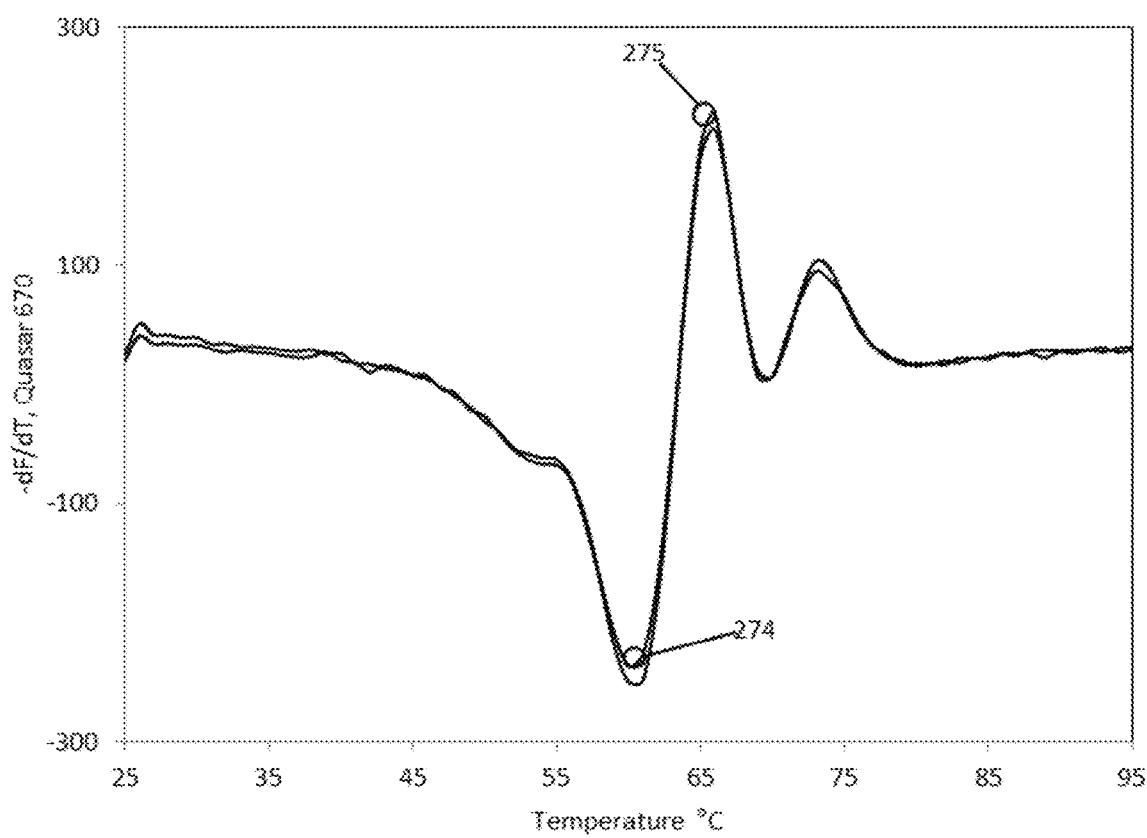
Figure 33:
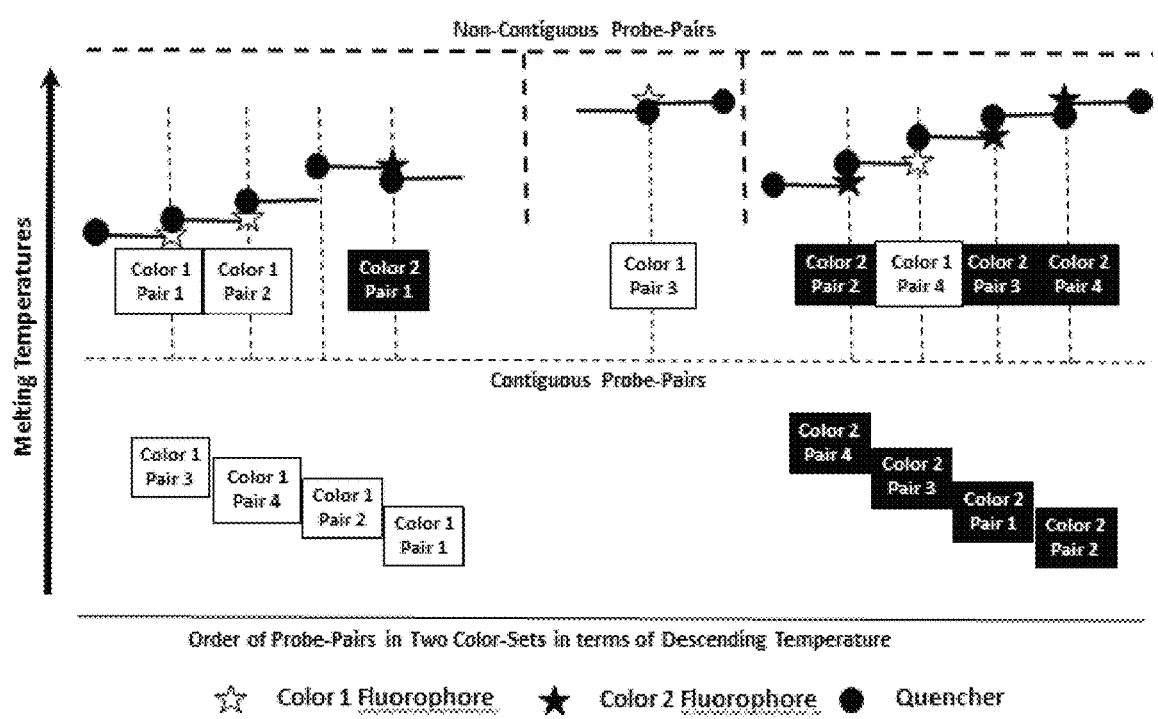
FIG. 33 has two panels. Panel (A) depicts a schematic of an exemplary Design II hybridizing probe set. Panel (B) depicts the alteration of probe hybridization Tm's by changes in target sequence.
Figure 33:
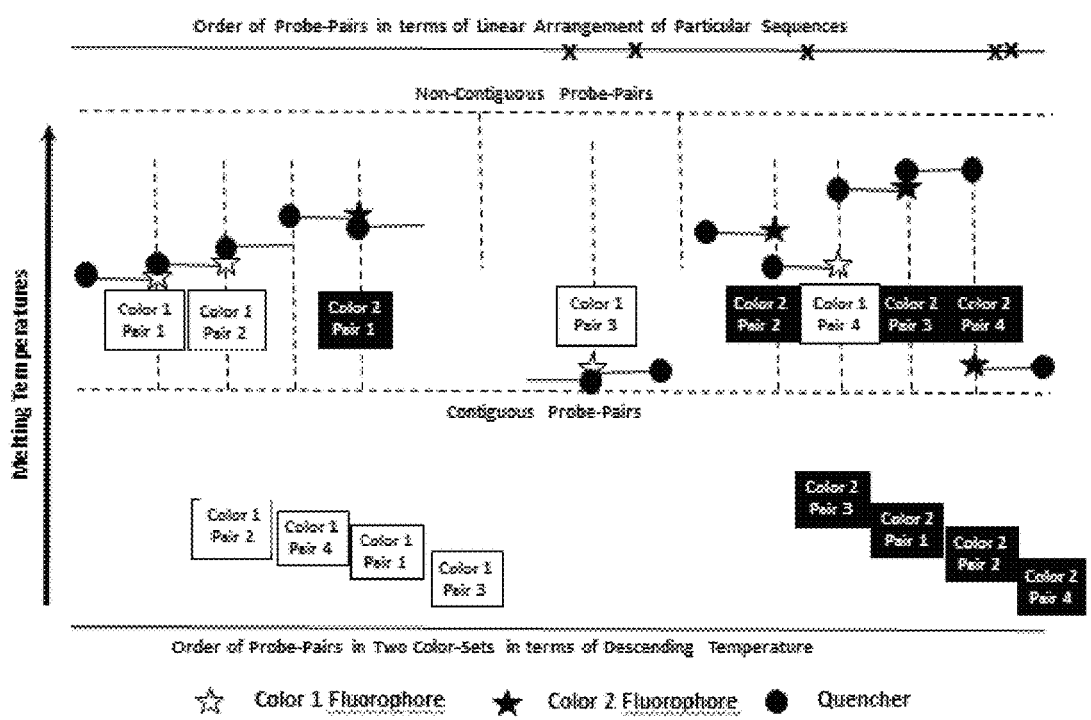

Mutation Detection Assay Using 3 Colors in Different Strains of *M. Tuberculosis* for the Pyrazinamide Gene A monoplex LATE PCR assay was used to detect mutational differences from the sensitive strain in the pncA gene and a portion of the 5' promoter region upstream. In this case the total target length was 685 nucleotides. The amplicon was coated with 35 Lights-On and Lights-Off probes in three fluorescent colors (Cal Orange 560, Cal Red 610 and Quasar 670). The results are shown in FIGS. 30-32 in comparison to those obtained with the two color assay. FIGS. 30A and 30B show the results of the two color assay (see example 3) in which a mutational strain (a single base change at nucleotide position 307, a thymidine (T) to a cytosine (C)) did not show a difference in fluorescent signatures from the sensitive strain in either color. FIGS. 30A and 30B shows the results of the 2 color assay in Cal Red 610 and Quasar 670 respectively, for the sensitive strain (lines 250 and 252) and the mutational strain (lines 251 and 253). Because of the failure of the two color assay to resolve this mutational difference, the 3 color assay was used on these same strains with the results shown in FIGS. 31A-C. The results for two of the colors (Cal Orange 560, FIG. 26A and Quasar 670, FIG. 31B) show identical fluorescent signatures while the third color (Cal Red 610, FIG. 31C) has two distinct signature, thus showing the presence of the mutation. In FIG. 31A, which shows the Cal Orange 560 results line 260 is the sensitive strain while line 261 is the mutational strain. The results in Quasar 670 are in FIG. 31B with line 262 (sensitive strain), line 263 (mutational strain). The clear difference in signatures is shown in FIG. 31C, Cal Red 610 where line 264 is the sensitive strain and line 265 the mutational strain thus the 3 color assay was able to distinguish this mutational strain while the 2 color assay did not. Additional results from this 3 color assay are shown in FIGS. 32A-C. FIGS. 32A-C compares the results of a mutational strain that contained a single base pair deletion of a guanine (G) nucleotide at position twenty two with the sensitive strand. FIG. 32A, the Cal Orange 560 where line 271 is the mutational strain showed a strong alteration of the fluorescent signature as compared to the sensitive strain (line 270) indicating the presence of a mutation. The results of the other fluors Cal Red 610 (FIG. 32B) and Quasar 670 (FIG. 32C) shown nearly identical fluorescent signatures for both strains (sensitive strain, lines 272 and 274 and mutational strains, lines 273 and 275).

LATE PCR amplifications were carried out in a 25 µl volume consisting of 1×PCR buffer (Invitrogen, Carlsbad, Calif.), 3 mM MgCl2, 300 nM dNTPs, 600 nM of the Primesafe 1, 50 nM limiting primer and 1000 nM excess primer, 1.5 units of Taq DNA Polymerase (Invitrogen, Carlsbad, Calif.), 50 nM of each On probe and 150 nM of each Off probe and 25 nM internal control On strand with 75 nM of internal Off strand. For each strain tested approximately 1000 genomes equivalents were used and amplification reactions were run. The thermal profile for the amplification reaction was as follows: 97° C./7 s-75° C./45 s for 60 cycles, followed by 10 min at 75° C., followed by 10 min at 25° C. This is followed by a melt starting at 25° C. with 1° C. increments at 20 s intervals to 98° C. At the end of 60 cycles the probe target hybridizations were analyzed by melt curve analysis using the first derivative for each fluor separately for the temperatures between 25° C. to 95° C. Results are presented in FIGS. 30-32 as the first derivative for the fluorescence signals of all probes plus the internal controls as a function of the temperature.

Sequences

Primers (SEQ ID NO: 1)
rpoB limiting primer
CTCCAGCCAGGCACGCTCACGTGACAGACCG (SEQ ID NO: 2)
rpoB excess primer
ACGTGGAGGCGATCACACCGCAGACGTT (SEQ ID NO: 3)
katG limiting primer
AGCGCCCACTCGTAGCCGTACAGGATCTCGAGGAAAC (SEQ ID NO: 4)
katG excess primer
TCTTGGGCTGGAAGAGCTCGTATGGCAC (SEQ ID NO: 5)
inhA promotor limiting primer
TTCCGGTAACCAGGACTGAACGGGATACGAATGGGGGTTTGG (SEQ ID NO: 6)
inhA promotor excess primer
TCGCAGCCACGTTACGCTCGTGGACATAC (SEQ ID NO: 7)
pncA limiting primer
AACTGCCCGGCCAGTCGCCCGAACGTATGGTGGACGT (SEQ ID NO: 8)
pncA excess primer
GTTCATCCCGGTTCGGCGGTGCCA (SEQ ID NO: 9)
Internal control limiting primer
TTCGGCGCACAAAGTGTCTCTGGCTGTTGT (SEQ ID NO: 10)
Internal control excess primer
GGCACGATGCTCCCACATTGCGACTTC Probes
rpoB_Probe1_OFF
(SEQ ID NO: 11)
BHQ2-CTGGTTGGTGCAGAAG-C3 Spacer rpoB_Probe_1a_OFF
(SEQ ID NO: 100)
BHQ2-CTGGTTGGTGCTGAAG-C3 Spacer rpoB_Probe2_ON
(SEQ ID NO: 12)
BHQ2-TCAGGTCCATGAATTGGCTCAGA-QSR670 rpoB_Probe3_OFF
(SEQ ID NO: 13)
BHQ2-CAGCGGGTTGTT-C3 Spacer rpoB_Probe4_ON
(SEQ ID NO: 14)
BHQ2-ATGCGCTTGTGGATCAACCCCGAT-QSR670 rpoB_Probe4a_ON
(SEQ ID NO: 101)
BHQ2-ATGCGCTTGTTGGTCAACCCCGAT-QSR670 rpoB_Probe5_ON
(SEQ ID NO: 15)
QSR670-AAGCCCCAGCGCCGACAGTCGTT-BHQ2 rpoB_Probe5a_ON
(SEQ ID NO: 102)
QSR670-AAGCCCCAGCGCCGTCAGTCGTT-BHQ2 rpoB_Probe6_OFF
(SEQ ID NO: 16)
ACAGACCGCCGG-BHQ2 katG_ON
(SEQ ID NO: 17)
QSR670-ACTCGCGTCCTTACCCAAAAAAAAAAAAAA-BHQ2 katG_OFF
(SEQ ID NO: 18)
ATGTCGGTGGTGA-BHQ2 inhA promotor_ON
(SEQ ID NO: 19)
BHQ2-AAAAAAAAAAAAAAAGGCAGTCATCCCGTT-QSR670 inhA promotor_OFF
(SEQ ID NO: 20)
BHQ2-TTACAGCCTATCGCCTCGC-C3 pncA_probe_025_040_ON
(SEQ ID NO: 21)
CR610-TCGGTTTGCAGCTCCTGAGA-BHQ2 pncA_probe_041_054_OFF
(SEQ ID NO: 22)
GCCAGCGTCGAGTT-BHQ2 pncA_probe_055_074_ON
(SEQ ID NO: 23)
CR610-CGCTGGAGGAGATGTGCACCAAAAAAAAAAAAAA-BHQ2 pncA_probe_075_100_OFF
(SEQ ID NO: 24)
TGTGTTGGTCGATACTACCGTCGCCG-BHQ2 pncA_probe_101_118_ON
(SEQ ID NO: 25)
CR610-AGGGTGGACTTGACAGCGGGCT-BHQ2 pncA_probe_119_132_OFF
(SEQ ID NO: 26)
GCCACTAGGGTGCT-BHQ2 pncA_probe_133_146_ON
(SEQ ID NO: 27)
CR610-AATACGCAATGGCTTGTT-BHQ2 pncA_probe_147_156_OFF
(SEQ ID NO: 28)
GAGGACGCGG-BHQ2 pncA_probe_157_175_ON
(SEQ ID NO: 29)
CR610-GTTTGTGTGCGCTAGATGGCCAC-BHQ2 pncA_probe_176_188_OFF
(SEQ ID NO: 30)
TTGCCACCGATCA-BHQ2 pncA_probe_189_204_ON
(SEQ ID NO: 31)
CR610-TCGTCGATGTGGTTGGTAGA-BHQ2 pncA_probe_205_215_OFF
(SEQ ID NO: 32)
GCGTCGATGAG-BHQ2 pncA_probe_216_229_ON
(SEQ ID NO: 33)
CR610-ATGCTGTGGCAATGCGAT-BHQ2 pncA_probe_230_241_OFF
(SEQ ID NO: 34)
ACTGCTGAATTG-BHQ2 pncA_probe_242_262_ON
(SEQ ID NO: 35)
CR610-TAAGTCGATGAGAACGGTACGCCTA-BHQ2 pncA_probe_263_276_OFF
(SEQ ID NO: 36)
AGCGGCTTCGAAGG-BHQ2 pncA_probe_277_293_ON
(SEQ ID NO: 37)
QSR670-AACCTACACCGGAGCGTACTT-BHQ2 pncA_probe_294_307_OFF
(SEQ ID NO: 38)
GTTCTACAAGGGTG-BHQ2 pncA_probe_308_331_ON
(SEQ ID NO: 39)
QSR670-TAGGACACGTTGGCAGTTGAGGCGGTTAAAAAAAA-BHQ2 pncA_probe_332_353_OFF
(SEQ ID NO: 40)
GCGCGGACTTCTATCCCAGTCT-BHQ2 pncA_probe_354_372_ON
(SEQ ID NO: 41)
QSR670-TGTGCGTCAGTGGTACTTCCGCAAAAAAAAAAAA-BHQ2 pncA_probe_373_388_ON
(SEQ ID NO: 42)
QSR670-GTGTCGTGGCTACCGCATAC-BHQ2 pncA_probe_389_405_OFF
(SEQ ID NO: 43)
ACACCGGACTATTCTTCG-BHQ2 pncA_probe_406_427_ON_Bovis
(SEQ ID NO: 44)
QSR670-CCCGGGTGACGACTTCTCCGGC-BHQ2 pncA_probe_428_448_OFF
(SEQ ID NO: 45)
AACCAAGGACTTCCACATCGA-BHQ2 pncA_probe_449_478_ON
(SEQ ID NO: 46)
QSR670-AACGAAGCGGTGGACTATCGTTACGTTGTGGCTT-BHQ2 pncA_probe_479_501_OFF_2
(SEQ ID NO: 47)
CGCGCTATCAGTGACTACCTGGC-BHQ2 pncA_probe_502_521_ON
(SEQ ID NO: 48)
QSR670-CCGGTGGTGTTGTGCTGGCCAAAAAAAAAAAAAA-BHQ2 pncA_probe_522_546_OFF
(SEQ ID NO: 143)
TGTGAGGGTGGTTCGTTGGCGGTAA-BHQ2 pncA_probe_547_569_ON
(SEQ ID NO: 50)
QSR670-TTTCGTTGACGTGCAGAACGACTTCAA-BHQ2 pncA_probe_570_585_OFF
(SEQ ID NO: 51)
ATGCGGGCGTTGATCA-BHQ2

1st Internal Control ON
(SEQ ID NO: 52)
QSR670-ATTCTATTATTTATTTTCAT-BHQ2

1st Internal Control OFF
(SEQ ID NO: 53)
ATCATTATTTACTA-BHQ2

Internal markers
2nd Internal Control ON
(SEQ ID NO: 54)
QSR670-CAGCTGCACTGGGAAGGGTGCAGTCTGACC-C3

2nd Internal Control OFF
(SEQ ID NO: 55)
GGTCAGACTGCACCCTTCCCAGTGCAGCTG-BHQ2

Primesafe II
Primesafe Sense
(SEQ ID NO: 56)
Dabcyl-GGATCAGATTAGCACTGATGTA-Dabcyl Primesafe Antisense
(SEQ ID NO: 57)
Dabcyl-TACATCAGTGCTAATCTGATCC-Dabcyl Primesafe PS1
(SEQ ID NO: 60)
Dabcyl-GAATAATATAGCCCCCCCCCCCCCCCCCCCCCTATATTATT
C-Dabcyl -continued pncA Design II probes
pncA-designII_196-215 (SEQ ID NO: 65)
QSR670-AACGCCGCGCTGGAGGAGATGCTT-BHQ2 pncA-designII_216-230 (SEQ ID NO: 66)
GGCCGATACCACCGT-BHQ2 pncA-designII_406-425 (SEQ ID NO: 67)
QSR670-ACCATCGGAGCGTACAGCGGCTGT-BHQ2 pncA-designII_426-440 (SEQ ID NO: 68)
CTACAAGGGTGCCTA-BHQ2 pncA-designII_161-180 (SEQ ID NO: 69)
QSR670-ACAGTTGGTTTGCAGCTCCTGAGT-BHQ2 pncA-designII_181-195 (SEQ ID NO: 70)
GCACTGCCGGCGTCG-BHQ2 pncA-designII_546-565 (SEQ ID NO: 71)
QSR670-AAGACCCGGGTGATCACTTCTCTT-BHQ2 pncA-designII_566-580 (SEQ ID NO: 72)
AAGGACTTCCACATC-BHQ2 pncA-designII_616-635 (SEQ ID NO: 73)
QSR670-AACGCTATCAGTGACTACCTGGTT-BHQ2 pncA-designII_636-650 (SEQ ID NO: 74)
CGCTGCGTTGGCTCG-BHQ2 pncA-designII_441-460 (SEQ ID NO: 75)
QSR670-AATCGGCAATTGAGTCGGTGTTTT-BHQ2 pncA-designII_461-475 (SEQ ID NO: 76)
CAGTCTGGACGCG-BHQ2 pncA-designII_266-285 (SEQ ID NO: 77)
CO560-TAGCGGTACGCAATGGCTTGGCCTA-BHQ1 pncA-designII_286-300 (SEQ ID NO: 78)
AGACGGCCGAGGAC-BHQ1 pncA-designII_581-600 (SEQ ID NO: 79)
CO560-ACACCATCACGTCGTGGCAACCGT-BHQ1 pncA-designII_601-615 (SEQ ID NO: 80)
CCGGAGCGGCGGGCT-BHQ1 pncA-designII_476-495 (SEQ ID NO: 81)
CO560-ACCTCTCGGCGTGGACTTCTATCCGT-BHQ1 pncA-designII_496-510 (SEQ ID NO: 82)
ATTGCGTTAGCGGTA-BHQ1 pncA-designII_685-705 (SEQ ID NO: 83)
CO560-TTTCGTTGACGTGCAGAATGACAA-BHQ1 pncA-designII_706-720 (SEQ ID NO: 84)
TGCGGGTGTTGGTCA-BHQ1 pncA-designII_371-390 (SEQ ID NO: 85)
CO560-AAAGAATGGTACGTCACTGCTGTT-BHQ1 pncA-designII_391-405 (SEQ ID NO: 86)
TCGGAGGAGTTGACG-BHQ1 pncA-designII_511-530 (SEQ ID NO: 87)
CR610-ACTTCCTCGTCGTGGCCATCGCGT-BHQ2 pncA-designII_531-345 (SEQ ID NO: 88)
CGGCACACTGGACTA-BHQ2 pncA-designII_336-355 (SEQ ID NO: 89)
CR610-AGCGCGGCGTCGATGAGGTTGACT-BHQ2 pncA-designII_356-370 (SEQ ID NO: 90)
AATTGGCTGCGGTAA-BHQ2 pncA-designII_651-670 (SEQ ID NO: 91)
CR610-AATCGCTGGCGGTAACTGGTGGTT-BHQ2 pncA-designII_671-685 (SEQ ID NO: 92)
TTCTGCGAGGGTGGC-BHQ2 pncA-designII_301-320 (SEQ ID NO: 93)
CR610-AACATCGATCATTGTGTGCGCCTT-BHQ2 pncA-designII_321-335 (SEQ ID NO: 94)
TGTGGTCGGTATTGC-BHQ2 pncA-designII_231-250 (SEQ ID NO: 95)
CR610-AAGACTTGACAGCGGGTGTGTCTT-BHQ2 pncA-designII_251-265 (SEQ ID NO: 96)
ACTAGGGTGCTGGTG-BHQ2 pncA-designII_721-740 (SEQ ID NO: 97)
CR610-TTCCGAACGTATGGTGGATGTAAA-BHQ2 pncA-designII_741-755 (SEQ ID NO: 98)
TGCTTGGGCAGTTGC-BHQ2 pncA-designII_356-370_B (SEQ ID NO: 99)
AATTGGCTGTGGCGG-BHQ2

All publications and patents provided herein incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

What is claimed is:

1. A method for analyzing two different single-stranded nucleic acid target sequences in a sample, comprising:
   (a) providing detection regents comprising different probe-pairs, each of said different probe-pairs comprising:
      (i) a quencher probe labeled with a non-fluorescent quencher,
      (ii) a signaling probe labeled with a fluorescent dye and a non-fluorescent quencher, wherein the signaling probe is a self-quenching probe and the non-fluorescent quencher reduces a fluorescent signal from the fluorescent dye when the signaling probe is not hybridized to a single-stranded nucleic acid target sequence such that a background fluorescent signal is emitted from the signaling probe,
      wherein above background fluorescent signal is emitted from the signaling probe when the signaling probe is bound to the single-stranded nucleic acid target sequence but the quencher probe is not bound to the single-stranded nucleic acid target sequence,
      wherein the signaling probe and the quencher probe hybridize adjacently on the single-stranded nucleic acid target sequence such that the fluorescent signal from the signaling probe is quenched by the non-fluorescent quencher of the quencher probe when both the signaling probe and the quencher probe are specifically bound to the single-stranded nucleic acid target sequence;
      wherein the signaling probe of each of said different probe-pairs are labeled with an identical fluorescent dye;
   (b) contacting a sample comprising a first single-stranded nucleic acid target sequence and a second single-stranded nucleic acid target sequence, with said detection reagents in a single tube at a hybridization condition, forming a mixture such that, in the mixture, each of said different probe-pairs specifically hybridizes to its corresponding single-stranded nucleic acid target sequence, each of said different probe-pairs is adjacent each other on the its corresponding single-stranded nucleic acid target sequence and the fluorescent signal from the signaling probe from each of said different probe-pairs is quenched by the non-fluorescent quencher of its corresponding quencher probe from the same probe pair of said different probe-pairs, wherein the first single-stranded nucleic acid target sequence and the second single-stranded nucleic acid target sequence have different sequences, wherein the melting temperature of a hybridization complex formed by the signaling probe of each of said different probe-pairs and its corresponding single-stranded nucleic acid target sequence is higher than the melting temperature of a hybridization complex formed by the quencher probe of the same probe-pair containing the signaling probe from said different probe-pairs and the its corresponding single-stranded nucleic acid target sequence;
   (c) heating the mixture by gradually increasing the temperature of the mixture;
   (d) generating two different melting curves by analyzing the fluorescent signal from the signaling probe from one of said different probe-pairs specifically hybridizing the first single-stranded nucleic acid target sequence in the sample and the fluorescent signal from the signaling probe from another of said probe-pairs specifically hybridizing the second single-stranded nucleic acid target sequence in the sample as a function of temperature, thereby analyzing the two different single-stranded nucleic acid target sequences in the sample,
      wherein the first single-stranded nucleic acid target sequence and the second single-stranded nucleic acid target sequence in the sample are differentiated based on the two different melting curves,
      and wherein the first single-stranded nucleic acid target sequence and the second single-stranded nucleic acid target sequence are *Mycobacterium tuberculosis* nucleic acid sequences comprising portions of the kalG, rpoB, inhA promotor, and/or pncA genes.

2. The method of claim 1, wherein said signaling probe of each of said different probe-pairs is molecular beacon probe.

3. The method of claim 1, wherein said signaling probe of each of said different probe-pairs comprise a target binding region and a nonbinding region between the non-fluorescent quencher and the fluorescent dye.

4. The method of claim 1, wherein each of the different melting curves is compared to a known curve or a control curve.

5. The method of claim 1, wherein the presence of the first single-stranded nucleic acid target sequence and the second single-stranded nucleic acid target sequence are detected by said analyzing the fluorescent signal from the signaling probe from one of said probe-pairs specifically hybridizing the first single-stranded nucleic acid target sequence and the fluorescent signal from the signaling probe from another of said probe-pairs specifically hybridizing the second single-stranded nucleic acid target sequence in the sample as a function of temperature.

6. The method of claim 1, wherein the signaling probe or the quencher probe of the one of said different probe-pairs specifically hybridizing the first single-stranded nucleic acid target sequence has a melting temperature in the range of 10-75° C.

7. The method of claim 6, wherein the first single-stranded nucleic acid target sequence comprises a portion of the *Mycobacterium tuberculosis* inhA promotor gene.

8. The method of claim 7, wherein the signaling probe of the one of said different probe-pairs specifically hybridizing the firs single-stranded nucleic acid target sequence has at least 70% identity with SEQ ID NO: 19 and the quencher probe of the one of said different probe-pairs specifically hybridizing the first single-stranded nucleic acid target sequence has at least 70% identity with SEQ ID NO: 20.

9. The method of claim 1, wherein the signaling probe or the quencher probe of the another of said different probe-pairs specifically hybridizing the second single-stranded nucleic acid target sequence has a melting temperature in the range of 10-75° C.

10. A method for analyzing two different single-stranded nucleic acid target sequences in a sample, comprising:
 (a) providing detection regents comprising different probe-pairs, each of said probe-pairs comprising:
  (i) a quencher probe labeled with a non-fluorescent quencher,
  (ii) a signaling probe labeled with a fluorescent dye and a non-fluorescent quencher,
  wherein the signaling probe is a self-quenching probe and the non-fluorescent quencher reduces a fluorescent signal from the fluorescent dye when the signaling probe is not hybridized to a single-stranded nucleic acid target sequence such that a background fluorescent signal is emitted from the signaling probe,
  wherein above background fluorescent signal is emitted from the signaling probe when the signaling probe is bound to the single-stranded nucleic acid target sequence but the quencher probe is not bound to the single-stranded nucleic acid target sequence,
  wherein the signaling probe and the quencher probe hybridize adjacently on the single-stranded nucleic acid target sequence such that the fluorescent signal from the signaling probe is quenched by the non-fluorescent quencher of the quencher probe when both the signaling probe and the quencher probe are specifically bound to the single-stranded nucleic acid target sequence;
  wherein the signaling probe of each of said different probe-pairs are labeled with an identical fluorescent dye;
 (b) contacting a sample comprising a first single-stranded nucleic acid target sequence and a second single-stranded nucleic acid target sequence, with said detection reagents in a single tube at a high temperature, forming a mixture such that, in the mixture, each of the first single-stranded nucleic acid target sequence and the second single-stranded nucleic acid target sequence is not able to form a double stranded nucleic acid with its corresponding probe-pair from said different probe-pairs, wherein the first single-stranded nucleic acid target sequence and the second single-stranded nucleic acid target sequence have different sequences, wherein the melting temperature of a hybridization complex formed by the signaling probe of each of said different probe-pairs and its corresponding single-stranded nucleic acid target sequence is higher than the melting temperature of a hybridization complex formed by the quencher probe of the same probe-pair containing the signaling probe from said different probe-pairs and the its corresponding single-stranded nucleic acid target sequence;
 (c) cooling the mixture by gradually decreasing the temperature of the mixture;
 (d) generating two different annealing curves by analyzing the fluorescent signal from the signaling probe from one of said different probe-pairs specifically hybridizing the first single-stranded nucleic acid target sequence in the sample and the fluorescent signal from the signaling probe from another of said different probe-pairs specifically hybridizing the second single-stranded nucleic acid target sequence in the sample as a function of temperature, thereby analyzing the two different single-stranded nucleic acid target sequences in the sample,
  wherein the first single-stranded nucleic acid target sequence and the second single-stranded nucleic acid target sequence in the sample are differentiated based on the two different annealing curves,
  and wherein the first single-stranded nucleic acid target sequence and the second single-stranded nucleic acid target sequence are Mycobacterium tuberculosis nucleic acid sequences comprising portions of the kalG, rpoB, inhA promotor, and/or pncA genes.

\* \* \* \* \*

SEQUENCE LISTING

<160> NUMBER OF SEQ ID NOS: 143

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctccagccag gcacgctcac gtgacagacc g                                    31

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acgtggaggc gatcacaccg cagacgtt                                        28

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agcgcccact cgtagccgta caggatctcg aggaaac                              37

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcttgggctg gaagagctcg tatggcac                                        28

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttccggtaac caggactgaa cgggatacga atgggggttt gg                        42

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcgcagccac gttacgctcg tggacatac                                       29

```
<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aactgcccgg ccagtcgccc gaacgtatgg tggacgt                                 37

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gttcatcccg gttcggcggt gcca                                               24

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttcggcgcac aaagtgtctc tggctgttgt                                         30

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggcacgatgc tcccacattg cgacttc                                            27

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
ctggttggtg cagaag                                                        16

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
tcaggtccat gaattggctc aga                                                23
```

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
cagcgggttg tt                                                        12

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
atgcgcttgt ggatcaaccc cgat                                           24

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
aagccccagc gccgacagtc gtt                                            23

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
acagaccgcc gg                                                        12

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
actcgcgtcc ttacccaaaa aaaaaaaaaa                                     30

<210> SEQ ID NO 18
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
atgtcggtgg tga                                                       13

```
<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
aaaaaaaaaa aaaaaggcag tcatcccgtt                                          30

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
ttacagccta tcgcctcgc                                                      19

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
tcggtttgca gctcctgaga                                                     20

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
gccagcgtcg agtt                                                           14

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
cgctggagga gatgtgcacc aaaaaaaaaa aaaaa                                    35

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
tgtgttggtc gatactaccg tcgccg                                              26

<210> SEQ ID NO 25
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
agggtggact tgacagcggg ct                                              22

<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
gccactaggg tgct                                                       14

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
aatacgcaat ggcttgtt                                                   18

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
gaggacgcgg                                                            10

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
gtttgtgtgc gctagatggc cac                                             23

<210> SEQ ID NO 30
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
ttgccaccga tca                                                        13

<210> SEQ ID NO 31
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
tcgtcgatgt ggttggtaga                                              20

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
gcgtcgatga g                                                       11

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
atgctgtggc aatgcgat                                                18

<210> SEQ ID NO 34
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
actgctgaat tg                                                      12

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
taagtcgatg agaacggtac gccta                                        25

<210> SEQ ID NO 36
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
agcggcttcg aagg                                                    14

<210> SEQ ID NO 37
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 37
aacctacacc ggagcgtact t                                               21

<210> SEQ ID NO 38
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
gttctacaag ggtg                                                       14

<210> SEQ ID NO 39
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
taggacacgt tggcagttga ggcggttaaa aaaaa                                35

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
gcgcggactt ctatcccagt ct                                              22

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
tgtgcgtcag tggtacttcc gcaaaaaaaa aaaaa                                35

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
gtgtcgtggc taccgcatac                                                 20

<210> SEQ ID NO 43
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 43
acaccggact attcttcg                                                       18

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
cccgggtgac gacttctccg gc                                                  22

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
aaccaaggac ttccacatcg a                                                   21

<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
aacgaagcgg tggactatcg ttacgttgtg gctt                                     34

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
cgcgctatca gtgactacct ggc                                                 23

<210> SEQ ID NO 48
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
ccggtggtgt tgtgctggcc aaaaaaaaaa aaaaa                                    35

<210> SEQ ID NO 49
<211> LENGTH: 25
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 49
tgcgagggtg gttcgttggc ggtaa                                       25

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
tttcgttgac gtgcagaacg acttcaa                                     27

<210> SEQ ID NO 51
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
atgcgggcgt tgatca                                                 16

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
attctattat ttattttcat                                             20

<210> SEQ ID NO 53
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
atcattattt acta                                                   14

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
cagctgcact gggaagggtg cagtctgacc                                  30

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 55
ggtcagactg caccctccc agtgcagctg                                          30

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ggatcagatt agcactgatg ta                                                 22

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
tacatcagtg ctaatctgat cc                                                 22

<210> SEQ ID NO 58
<211> LENGTH: 500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
cttcacgtaa tacaagaacc agcgggggtt cggggcacac tcaccacgcg gggccggtgt        60
ggccctaagc gcagtcgaga cttgtcgggt agtgcgcctg gttctgagcg gtgtggagtg       120
ggtgcgccct acgtggggga ggcttcacga gcttccgagt tgcatctgtg agtgcgagct       180
taacgagcga gctgctccag tatgtggcat ggacacggtc cgcgccctca gaatgcgacg       240
gcaaaatgct cgcgagctgc ggtccgccgt accgatggta ccagataaga gacctgttag       300
gcaacctgtt caacggggca tgctctcaag tggatagact ccaccagtgc tggaggactc       360
ggcatgtctc ggaggtcgag gcatggcacg atgctcccct attgcgactt ccgggctcga       420
aggaaccgat gccaaaagca acagccagag acactttgtg cgccgactgc ctaggtctgg       480
tcagcaattc ccaatacagc                                                   500

<210> SEQ ID NO 59
<211> LENGTH: 400
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
cttcacgtaa tacaagaagc agcgggttcg ggagtgtcac agtgggttgc cgtgtgtaag        60
agtcgagact tgtcgggtag tcctggttgt gtggtcgaac gcattagctt gggtcaacga       120
gcttccgagt tgcatctgtg agtttaacga gagccagtat gtagcgtcag aatgcagaat       180
cagcaggcac gtgtccgccg tagatggtac cagataagag acctgttagg caacctgttc       240

```
aaaatactac tctggaggac tgagatggca cgatgctccc acattgcgac ttctgccctt    300
gatagttata ttgaaagtaa atagtagata gtagatgatg atataaacaa cagccagaga    360
cactttgtgc gccgactgcc tatcaaattc ccaatacagc                          400
```

<210> SEQ ID NO 60
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60

```
gaataatata gcccccccccc cccccccccc ccctatatt attc                      44
```

<210> SEQ ID NO 61
<211> LENGTH: 191
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
acgtggaggc gatcacaccg cagacgttga tcaacatccg gccggtggtc gccgcgatca    60
aggagttctt cggcaccagc cagctgagcc aattcatgga ccagaacaac ccgctgtcgg    120
ggttgaccca caagcgccga ctgtcggcgc tggggcccgg cggtctgtca cgtgagcgtg    180
ccgggctgga g                                                         191
```

<210> SEQ ID NO 62
<211> LENGTH: 139
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
gcttgggctg gaagagctcg tatggcaccg gaaccggtaa ggacgcgatc accagcggca    60
tcgaggtcgt atggacgaac accccgacga aatgggacaa cagtttcctc gagatcctgt    120
acggctacga gtgggagct                                                 139
```

<210> SEQ ID NO 63
<211> LENGTH: 139
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
tcgcagccac gttacgctcg tggacatacc gatttcggcc cggccgcggc gagacgatag    60
gttgtcgggg tgactgccac agccactgaa ggggccaaac ccccattcgt atcccgttca    120
gtcctggtta ccggaggaa                                                 139
```

<210> SEQ ID NO 64
<211> LENGTH: 110
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 64
ggcacgatgc tcccacattg cgacttctgc ccttgatagt tatattgaaa gtaaatagta    60
gatagtagat gatgatataa acaacagcca gagacacttt gtgcgccgaa              110

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
probe

<400> SEQUENCE: 65
aacgccgcgc tggaggagat gctt                                           24

<210> SEQ ID NO 66
<211> LENGTH: 15
<212> TYPE: DNA
<213> ORGANISM: Artificial Sequence
<220> FEATURE:
<223> OTHER INFORMATION: Description of Artificial Sequence: Synthetic
probe

<400> SEQUENCE: 66
ggccgatacc accgt                                                     15

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
probe

<400> SEQUENCE: 67
accatcggag cgtacagcgg ctgt                                           24

<210> SEQ ID NO 68
<211> LENGTH: 15
<212> TYPE: DNA
<213> ORGANISM: Artificial Sequence
<220> FEATURE:
<223> OTHER INFORMATION: Description of Artificial Sequence: Synthetic
probe

<400> SEQUENCE: 68
ctacaagggt gccta                                                     15

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
probe

<400> SEQUENCE: 69
acagttggtt tgcagctcct gagt                                           24

<210> SEQ ID NO 70
<211> LENGTH: 15
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 70
gcactgccgg cgtcg                                                    15

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
aagacccggg tgatcacttc tctt                                          24

<210> SEQ ID NO 72
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 72
aaggacttcc acatc                                                    15

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
aacgctatca gtgactacct ggtt                                          24

<210> SEQ ID NO 74
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
cgctgcgttg gctcg                                                    15

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75
aatcggcaat tgagtcggtg tttt                                          24

<210> SEQ ID NO 76
<211> LENGTH: 13
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 76
cagtctggac gcg                                                              13

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 77
tagcggtacg caatggcttg gccta                                                 25

<210> SEQ ID NO 78
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 78
agacggccga ggac                                                             14

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79
acaccatcac gtcgtggcaa ccgt                                                  24

<210> SEQ ID NO 80
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
ccggagcggc gggct                                                            15

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 81
acctctcggc gtggacttct atccgt                                                26

<210> SEQ ID NO 82
<211> LENGTH: 15
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 82
attgcgttag cggta                                                    15

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
tttcgttgac gtgcagaatg acaa                                          24

<210> SEQ ID NO 84
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
tgcgggtgtt ggtca                                                    15

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
aaagaatggt acgtcactgc tgtt                                          24

<210> SEQ ID NO 86
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 86
tcggaggagt tgacg                                                    15

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
acttcctcgt cgtggccatc gcgt                                          24

<210> SEQ ID NO 88
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 88
cggcacactg gacta                                                     15

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89
agcgcggcgt cgatgaggtt gact                                           24

<210> SEQ ID NO 90
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
aattggctgc ggtaa                                                     15

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 91
aatcgctggc ggtaactggt ggtt                                           24

<210> SEQ ID NO 92
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 92
ttctgcgagg gtggc                                                     15

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 93
aacatcgatc attgtgtgcg cctt                                           24

<210> SEQ ID NO 94
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 94
tgtggtcggt attgc                                                     15

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
aagacttgac agcgggtgtg tctt                                           24

<210> SEQ ID NO 96
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 96
actagggtgc tggtg                                                     15

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97
ttccgaacgt atggtggatg taaa                                           24

<210> SEQ ID NO 98
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98
tgcttgggca gttgc                                                     15

<210> SEQ ID NO 99
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99
aattggctgt ggcgg                                                     15

<210> SEQ ID NO 100
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100
```

```
ctggttggtg ctgaag                                                       16

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
atgcgcttgt tggtcaaccc cgat                                              24

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
aagccccagc gccgtcagtc gtt                                               23

<210> SEQ ID NO 103
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ggcacgatgc tcccacattg cgacttccgg gctcgaagga accgatgcca aaacaacagc       60
cagagacact ttgtgcgccg aa                                                82

<210> SEQ ID NO 104
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
ggcacgatgc tcccacattg cgacttctgg ccttgatagt tatattgaaa gtaaatagta      60
gatagtagat gatgatataa acaacagcca gagacacttt gtgcgccgaa                110

<210> SEQ ID NO 105
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ttcttcggca ccagccagc                                                    19

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 106
gttcttcggc accagccagc t                                              21

<210> SEQ ID NO 107
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ctgtcggggt tgacccacaa gcgccgact                                      29

<210> SEQ ID NO 108
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gctgtcgggg ttgacccaca agcgccg                                        27

<210> SEQ ID NO 109
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
agcgccgact gtcggcgctg gggccc                                         26

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
catcaggagc tgcaaaccaa                                                20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
aaccaactcg acgctggcgg                                                20

<210> SEQ ID NO 112
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
aaccaactcg acgctggcgg tgcgcatctc ctccagcgcg gcgacg        46

<210> SEQ ID NO 113
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gcgcggcgac ggtggtatcg gccgacacac cc        32

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
cacacccgct gtcaggtcca cca        23

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ccaccagcac cctggtggcc a        21

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
tggccaagcc attgcgtacc        20

<210> SEQ ID NO 117
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cgtaccgcgt cctcg        15

<210> SEQ ID NO 118
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
attgcgtacc gcgtcctcgg cggtctggcg cacacaatga tcggtgggaa taccgaccac    60
atcgac                                                               66

<210> SEQ ID NO 119
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
aatgatcggt ggcaa                                                     15

<210> SEQ ID NO 120
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
caatgatcgg tggcaatacc gaccacatcg acctcatcga cgccgc                   46

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cgacctcatc gacgccgcgt                                                20

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gacgccgcgt tgccgcagcc a                                              21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gcagccaatt cagcagtggc g                                              21

<210> SEQ ID NO 124
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ttcagcagtg gcgtgccgtt ctcgtcgact ccttcga                                    37

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
cgactccttc gaagccgctg tac                                                   23

<210> SEQ ID NO 126
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ccttcgaagc cgctgtacgc tccggtgtag gcacccttg                                  39

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
taggcaccct tgtagaacac c                                                     21

<210> SEQ ID NO 128
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
cccttgtaga acaccgcctc gattgccgac gtgtgcagac tgggat                          46

<210> SEQ ID NO 129
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ccgacgtgtc cagactggga tggaagtccg cgccgggagt ac                              42

<210> SEQ ID NO 130
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 130
cgcgccggga gtaccgctga cgcaatg                                        27

<210> SEQ ID NO 131
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
acgcaatgcg gtggccacga cgagg                                          25

<210> SEQ ID NO 132
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gccacgacga ggaatagtcc ggtgtgccgg agaagt                              36

<210> SEQ ID NO 133
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ccggtgtgcc ggagaagtgg tcacccgggt cgatg                               35

<210> SEQ ID NO 134
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
agtccggtgt gccggagaag tcgtcacccg ggtcgat                             37

<210> SEQ ID NO 135
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
tcacccgggt cgatgtggaa gtccttggtt gccacgacg                           39

<210> SEQ ID NO 136
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
```
tggaagtcct tggttgccac gacgtgatgg tagtccgccg cttcggccag gtagtcgct    59

<210> SEQ ID NO 137
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
tccgccgctt cggccaggta gtcgctgatg gcgcgggcca gcgcgg    46

<210> SEQ ID NO 138
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
cgcgggccag cgcggcgcca ccggtt    26

<210> SEQ ID NO 139
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ttgacgggcc gg    12

<210> SEQ ID NO 140
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
cggttaccgc cagcgagcca ccctcgcaga a    31

<210> SEQ ID NO 141
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
cgccagcgag ccaccctcgc agaagtcgtt ctgcacgtcg acgatgatca acgcc    55

<210> SEQ ID NO 142
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142

```
tcgacgatga tcaacgcccg catacgtcca ccat                          34

<210> SEQ ID NO 143
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 143
tgtgagggtg gttcgttggc ggtaa                                    25
```